(12) United States Patent
Duke-Cohan et al.

(10) Patent No.: US 6,933,132 B1
(45) Date of Patent: Aug. 23, 2005

(54) REGULATION OF IMMUNE RESPONSES BY ATTRACTIN

(75) Inventors: Jonathan S. Duke-Cohan, Newton Highlands, MA (US); Stuart F. Schlossman, Newton, MA (US)

(73) Assignee: Dana-Farber Cancer Institute Inc., Boston, MA (US)

( * ) Notice: Subject to any disclaimer, the term of this patent is extended or adjusted under 35 U.S.C. 154(b) by 0 days.

(21) Appl. No.: 09/787,097

(22) PCT Filed: Sep. 14, 1999

(86) PCT No.: PCT/US99/20948

§ 371 (c)(1),
(2), (4) Date: Jun. 27, 2001

(87) PCT Pub. No.: WO00/15651

PCT Pub. Date: Mar. 23, 2000

Related U.S. Application Data

(60) Provisional application No. 60/100,137, filed on Sep. 14, 1998.

(51) Int. Cl.[7] .......................... C07H 21/04; C12P 21/03; C12N 15/87; C12N 1/20; C12N 15/74
(52) U.S. Cl. ................... 435/69.1; 435/325; 435/252.3; 435/320.1; 435/455; 536/23.1
(58) Field of Search ................................ 435/69.1, 325, 435/252.3, 320.1, 455; 536/231

(56) References Cited

U.S. PATENT DOCUMENTS

| | | | |
|---|---|---|---|
| 4,997,764 A | | 3/1991 | Dalla Favera |
| 6,265,551 B1 | * | 7/2001 | Duke-Cohan et al. |
| 6,325,989 B1 | * | 12/2001 | Duke-Cohan et al. |

FOREIGN PATENT DOCUMENTS

| | | | | |
|---|---|---|---|---|
| WO | WO 00/57373 A | 2/2000 | ........... | C12N/15/12 |

OTHER PUBLICATIONS

Nagase et al, GenBank accession No. AB011120, Apr. 1998.*
Darnell et al. Molecular Cell Biology, New York: W H Freeman & Co; pp 248–255, 1986.*
Meinkoth J, Wahl G. Hybridization of nucleic acids immobilized on solid supports. Anal Biochem. 38(2):267–84, 1984.*
Nagase T, et al. Prediction of the coding sequences of unidentified human genes. IX. The complete sequences of 100 new cDNA clones from brain which can code for large proteins in vitro. DNA Res. 1998 Feb. 25;5(1):31–39.*
Skolnick et al. From genes to protein structure and function: novel applications of computational approaches in the genomic era. Trends Biotechnol. 18(1):34–9, 2000.*
Attwood TK. Genomics. The Babel of bioinformatics. Science. 290(5491):471–473, 2000.*
Metzler et al . Solution structure of human CTLA–4 and delineation of a CD80/CD86 binding site conserved in CD28. Nat Struc Biol. 4(7):527–531, 1997.*
Sambrook, J., Fritsch, EF, and Maniatis, T., in Molecular Cloning: A Laboratory Manual. Cold Spring Harbor Laboratory Press, NY, vol. 1, 2, 3 (1989), p. 11.7.*
Bernard et al., Biochemistry, 33:15204–15214 (1994).
Buc et al., Eur. J. Immunol., 20:611–615 (1990).
Callebaut et al., Science, 262:2045–2050 (1993).
Chikuma et al., Biol. Chem., 371:325–330 (1990).
Chobert et al., J. Biol. Chem., 265(4):2352–2357 (1990).
Dang et al., J. of Immunol., 144:4092–4100 (1990).
Wada et al., Proc. Nat. Acad. Sci. USA, 89:197–201 (1992).
Duke–Cohan et al., J. of Biol. Chem., 270(23):14107–14114 (1995).
Duke–Cohan et al., J. Immunol 156:1714–1721 (1996).
Darmoul et al., Ann. Hum. Genet., 54:191–197 (1990).
Fleischer, Immunology Today, 15(4):180–184 (1994).
Fox et al., J. Immunol., 133(3):1250–1256 (1984).
Fujita et al., Clinica Chimica Acta 88:15–20 (1978).
Hafler et al. Immunol., 137(2): 414–418 (1986).
Hama et al., Clinica Chimica Acta, 113:217–221 (1981).
Hegen et al., J. Immunol., 144(8):2908–2914 (1990).
Hino et al., Clin. Chem. 22(8):1256–1261 (1976).
Kameoka et al., Science 261:466–469 (1993).
Kasahara et al., Clinica Chimica Acta 139:295–302 (1984).
Kubota et al., Clin. Exp. Immunol., 96:292–296 (1994).
Kyouden et al., J. Biochem., 111:770–777 (1992).
Matsuda et al., Clinical Infectious Diseases 16:260–264 (1993).
Morimoto et al., J. Immunol., 143(11):3430–3439 (1989).
Morrison et al., J. Exp. Med. 177:1135–1143 (1993).
Niedzwicki et al., American J. of Hematology 37:152–155 (1991).
Schrader et al., J. of Biol. Chem., 254(23):11964–11968 (1979).
Scott et al., Leukemia Research 12(2):129–134 (1988).
Stancíková et al., Clin. Exp. Rheumatol., 30:381–385 (1992).
Tanaka et al., J. of Immunol., 149(2):481–486 (1992).
Tanaka et al., Proc. Natl., Acad. Sci. USA, 90:4586–4590 (1993).
Tanaka et al., Proc. Natl., Acad. Sci. USA, 91:3082–3086 (1994).
Torimoto et al., J. of Immunol., 147(8):2514–2517 (1991).
Torimoto et al., J. of Immunol., 29(2):183–192 (1992).
Ulmer et al., Scand. J. Immunol., 31:429–435 (1990).
Ungerer et al., Clin. Chem., 38(7):1322–1326 (1992).
Vanhoof et al., Eur. J. Clin. Chem. Clin. Biochem. 30:333–338 (1992).

(Continued)

*Primary Examiner*—Christina Chan
*Assistant Examiner*—Maher Haddad
(74) *Attorney, Agent, or Firm*—Fish & Richardson, P.C.

(57) ABSTRACT

The invention features attracting polypeptides and nucleic acids encoding them. The attractin polypeptides are useful for enhancing immune responses.

46 Claims, 22 Drawing Sheets

OTHER PUBLICATIONS

Duke–Cohan et al., (1998) "Attractin (DPPT–L), a member of the CUB family of cell adhesion and guidance proteins, is secreted by activated human T lymphocytes and modulates immune cell interactions" Proc. Natl. Acad. Sci. USA, 95(19):11336–11341.

Nagase et al. (1998) "Predication of the Coding Sequences of Unidentified Human Genes. IX. The Complete Sequences of 100 Now cDNA Clones From Brain Which Can Code For Large Proteins In Vitro" DNA Res. Univers. Acad. Press, JP, 5(5):31–39.

Tang et al., (2000) "Secreted and membrane attractin result from alternative splicing of the human ATRN gene" Proc. Natl. Acad. Sci. USA, 97(11):6025–6030.

Database EMBL—Apr. 10, 1998, O'Hara et al., "Homo sapiens mRNA for KIAA0548 protein, partial cds,", XP002294604. Database accession No. AB011120.

Copy of Supplementary Partial European Search Report dated Sep. 21, 2004 for Application No. 99949634.2–1521–US9920948.

* cited by examiner

```
  1  MVAAAAATEA RLRRRTAATA ALAGRSGGPH CVNGGRCNPG TGQCVCPAGW
 51  VGEQCQHCGG RFRLTGSSGF VTDGPGNYKY KTKCTWLIEG QPNRIMRLRF
101  NHFATECSWD HLYVYDGDSI YAPLVAAFSG LIVPERDGNE TVPEVVATSG
151  YALLHFFSDA AYNLTGFNIT YSFDMCPNNC SGRGECKISN SSETVECECS
201  ENWKGEACDI PHCTDNCGFP HRGICNSSDV RGCSCFSDWQ GPGCSVPVPA
251  NQSFWTREEY SNLKLPRASH KAVVNGNIMW VVGGYMFNHS DYNMVLAYDL
301  ASREWLPLNR SVNNVVVRYG HSLALYKDKI YMYGGKIDPT GNVTNELRVF
351  HIHNESWVLL TPKAKEQYAV VGHSAHIVTL KNGRVVMLVI FGHCPLYGYI
401  SNVQEYDLDK NTWSILHTQG ALVQGGYGHS SVYDHRTRAL YVHGGYKAFS
451  ANKYRLADDL YRYDVDTQMW TILKDSRFFR YLHTAVIVSG TMLVFGGNTH
501  NDTSMSHGAK CFSSDFMAYD IACDRWSVLP RPDLHHDVNR FGHSAVLHNS
551  TMYVFGGFNS LLLSDILVFT SEQCDAHRSE AACLAAGPGI RCVWNTGSSQ
601  CISWALATDE QEEKLKSECF SKRTLDHDRC DQHTDCYSCT ANTNDCHWCN
651  DHCVPRNHSC SEGQISIFRY ENCPKDNPMY YCNKKTSCRS CALDQNCQWE
701  PRNQECIALP ENICGIGWHL VGNSCLKITT AKENYDNAKL FCRNHNALLA
751  SLTTQKKVEF VLKQLRIMQS SQSMSKLTLT PWVGLRKINV SYWCWEDMSP
801  FTNSLLQWMP SEPSDAGFCG ILSEPSTRGL KAATCINPLN GSVCERPANH
851  SAKQCRTPCA LRTACGDCTS GSSECMWCSN MKQCVDSNAY VASFPFGQCM
901  EWYTMSTCPP ENCSGYCTCS HCLEQPGCGW CTDPSNTGKG KCIEGSYKGP
951  VKMPSQAPTG NFYPQPLLNS SMCLEDSRYN WSFIHCPACQ CNGHSKCINQ
1001 SICEKCENLT TGKHCETCIS GFYGDPTNGG KCQPCKCNGH ASLCNTNTGK
1051 CFCTTKGVKG DECQLCEVEN RYQGNPLRGT CYYTLLIDYQ FTFSLSQEDD
1101 RYYTAINFVA TPDEQNRDLD MFINASKNFN LNITWAASFS AGTQAGEEMP
1151 VVSKTNIKEY KDSFSNEKFD FRNHPNITFF VYVSNFTWPI KIQVQTEQ
```

FIG. 2

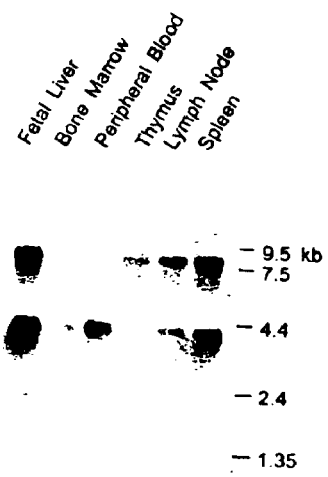
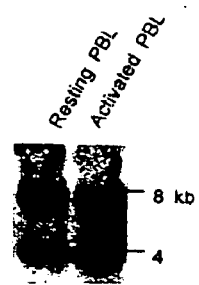
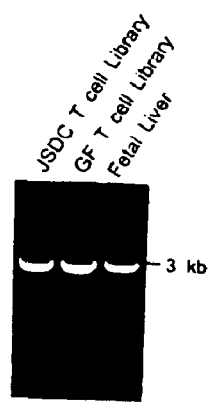
FIG. 3A  FIG. 3B  FIG. 3C
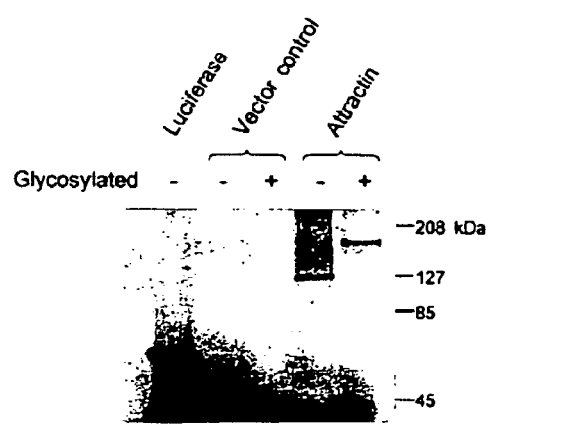
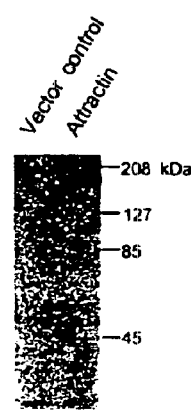
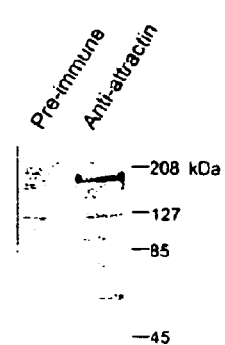
FIG. 6A  FIG. 6B  FIG. 6C

| | | | | | | | | | | | | | (SEQ ID NO:) |
|---|---|---|---|---|---|---|---|---|---|---|---|---|---|
| A | A | L | A | G | | G | S | G | | G | | P-H-C- | 21 |
| A | A | L | A | G | R | X | S | X | G | (GSA) | G-#- | | 22 |
| A | A | L | A | G | X | X | S | X | X | G | G-#- | | 23 |
| A | A | L | A | G | -(DE) | | S | G | (GS) | | P-#- | | 24 |

Attractin

Minimum serine protease

Prolyl oligo peptidase    -#-X-X-X-A-X-X-X-#-X(10)

Trypis

FIG. 4C

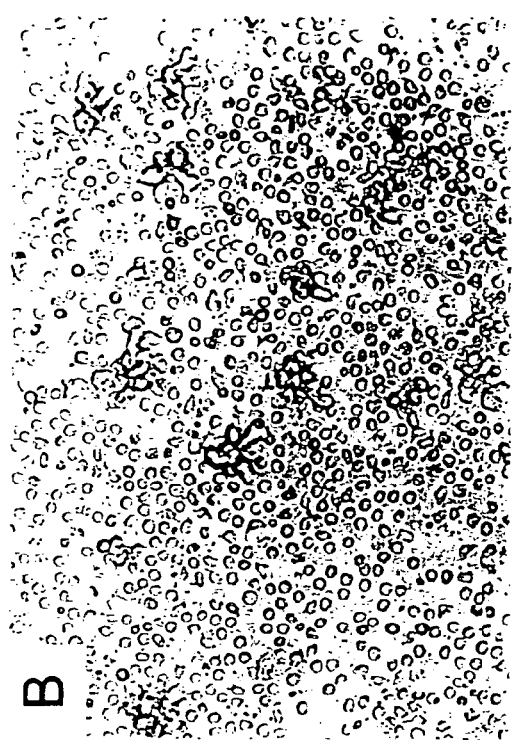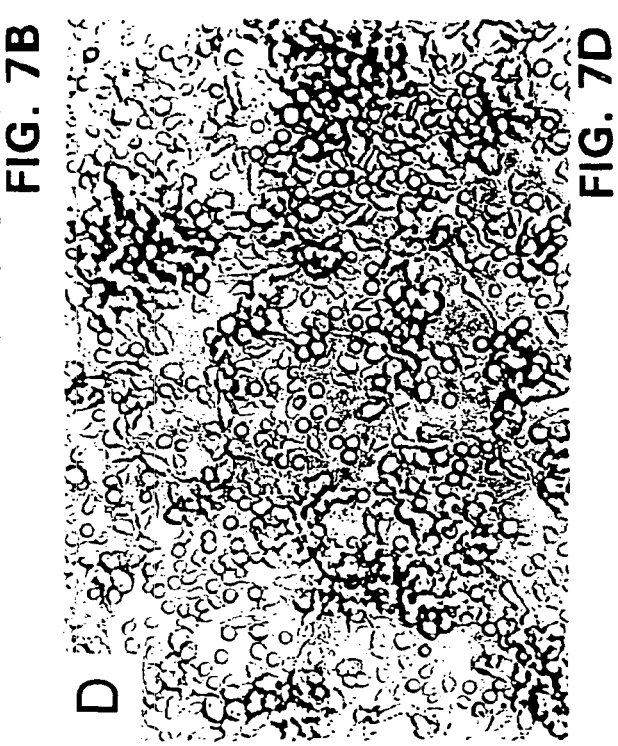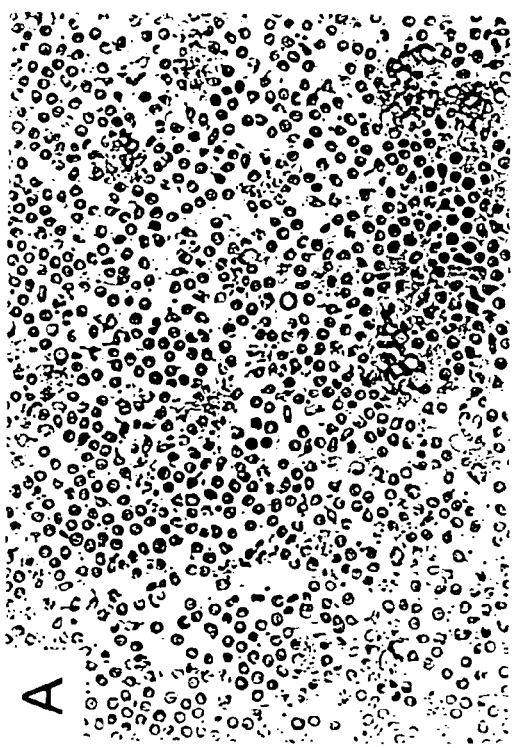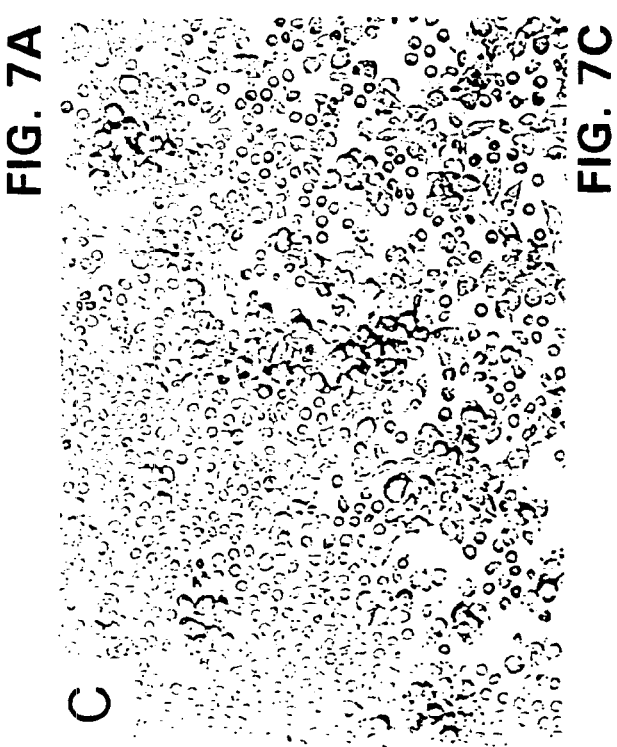

```
   1  ATGGTGGCCG CAGCGGCGGC AACTGAGGCA AGGCTGAGGA GGAGGACGGC
  51  GGCGACGGCA GCGCTCGCGG GCAGGAGCGG CGGGCCGCAC TGTGTCAACG
 101  GCGGTCGCTG CAACCCTGGC ACCGCCAGT GCGTCTGCCC CGCCGGCTGG
 151  GTGGGCGAGC AATGCCAGCA CTGCGGGGC CGCTTCAGAC TAACTGGATC
 201  TTCTGGGTTT GTGACAGATG GACCTGGAAA TTATAAATAC AAAACGAAGT
 251  GCACGTGGCT CATTGAAGGA CAGCCAAATA GAATAATGAG ACTTCGTTTC
 301  AATCATTTTG CTACAGAGTG TAGTTGGGAC CATTTATATG TTTATGATGG
 351  GGACTCAATT TATGCACCGC TAGTTGCTGC ATTTAGTGGC CTCATTGTTC
 401  CTGAGAGAGA TGGCAATGAG ACTGTCCCTG AGGTTGTTGC CACATCAGGT
 451  TATGCCTTGC TGCATTTTTT TAGTGATGCT GCTTATAATT TGACTGGATT
 501  TAATATTACT TACAGTTTTG ATATGTGTcC AAATAACTGC TCAGGcCGAG
 551  GAGAGTGTAA GATCAGTAAT AGCAGCGAAA CTGTTGAATG TGAATGTTCT
 601  GAAAACTGGA AAGGTGAAGC ATGTGACATT CCTCACTGTA CAGACAACTG
 651  TGGTTTTCCT CATCGAGGCA TCTGCAATTC AAGTGATGTC AGAGGATGCT
 701  CCTGCTTCTC AGACTGGCAG GGTCCTGGAT GTTCAGTTCC TGTACCAGCT
 751  AACCAGTCAT TTGGACTCG AGAGGAATAT TCTAACTTAA AGCTCCCCAG
 801  AGCATCTCAT AAAGCTGTGG TCAATGGAAA CATTATGTGG GTTGTTGGAG
 851  GATATATGTT CAACCACTCA GATTATAACA TGGTTCTAGC GTATGACCTT
 901  GCTTCTAGGG AGTGGCTTCC ACTAAACCGT TCTGTGAACA ATGTGGTTGT
 951  TAGATATGGT CATTCTTTGG CATTATACAA GGATAAAATT TACATGTATG
1001  GAGGAAAAAT TGATcCAACT GGGAATGTGA CCAATGAGTT GAGAGTTTTT
1051  CACATTCATA ATGAGTCATG GGTGTTGTTG ACCCCTAAGG CAAAGGAGCA
1101  GTATGCAGTG GTTGGGCACT CTGCACACAT TGTTACACTG AAGAATGGCC
1151  GAGTGGTCAT GCTGGTCATC TTTGGTCACT GCCCTCTCTA TGGATATATA
1201  AGCAATGTGC AGGAATATGA TTTGGATAAG AACACATGGA GTATATTACA
1251  CACCCAGGGT GCCCTTGTGC AAGGGGGTTA CGGCCATAGC AGTGTTTACG
1301  ACCATAGGAC CAGGGCCCTA TACGTTCATG GTGGCTACAA GGCTTTCAGT
```

FIG. 8A

1351 GCCAATAAGT ACCGGCTTGC AGATGATCTC TACCGATATG ATGTGGATAC
1401 CCAGATGTGG ACCATTCTTA AGGACAGCCG ATTTTTCCGT TACTTGCACA
1451 CAGCTGTGAT AGTGAGTGGA ACCATGCTGG TGTTTGGGGG AAACACACAC
1501 AATGACACAT CTATGAGCCA TGGCGCCAAA TGCTTCTCTT CAGATTTCAT
1551 GGCCTATGAC ATTGCCTGTG ACCGCTGGTC AGTGCTTCCC AGACCTGATc
1601 TCCACCATGA TGTCAACAGA TTTGGCCATT CAGCAGTCTT ACACAACAGC
1651 ACCATGTATG TGTTCGGTGG TTTCAATAGT CTCCTCCTCA GCGACATCCT
1701 GGTATTCACC TCGGAACAGT GTGATGCGCA TCGGAGTGAA GCCGCTTGTT
1751 TAGCAGCAGG ACCTGGTATT CGGTGTGTGT GGAACACAGG GTCGTCTCAG
1801 TGTATCTCGT GGGCGCTGGC AACTGATGAA CAAGAAGAAA AGTTAAAATC
1851 AGAATGTTTT TCCAAAAGAA CTCTTGACCA TGACAGATGT GACCAGCACA
1901 CAGATTGTTA CAGCTGtACA GCCAACACCA ATGACTGCCA CTGGTGCAAT
1951 GACCATTGTG TCCCCAGGAA CCACAGCTGC TCAGAAGGCC AGATCTCCAT
2001 TTTTAGGTAT GAGAATTGCC CCAAGGATAA CCCcATGTAC TACTGTAACA
2051 AGAAGACCAG CTGCAGGAGC TGTGCCCTGG ACCAGAACTG CCAGTGGGAG
2101 CCCCGGAATC AGGAGTGCAT TGCCCTGCCC GAAAATATCT GTGGCATTGG
2151 CTGGCATTTG GTTGGAAACT CATGTTTGAA AATTACTACT GCCAAGGAGA
2201 ATTATGACAA TGCTAAATTG TTCTGTAGGA ACCACAATGC CCTTTTGGCT
2251 TCTCTTACAA CCCAGAAGAA GGTAGAATTT GTCCTTAAGC AGCTGCGAAT
2301 AATGCAGTCA TCTCAGAGCA TGTCCAAGCT CACCTTAACC CCATGGGTCG
2351 GCCTTCGGAA GATCAATGTG TCCTACTGGT GCTGGGAAGA TATGTCCCCA
2401 TTTACAAATA GTTTACTACA GTGGATGCCG TCTGAGCCCA GTGATGCTGG
2451 ATTCTGTGGA ATTTTATCAG AACCCAGTAC TCGGGGACTG AAGGCTGCAA
2501 CCTGCATCAA CCCACTCAAT GGTAGTGTCT GTGAAAGGCC TGCAAACCAC
2551 AGTGCTAAGC AGTGCCGGAC ACCATGTGCC TTGAGGACAG CATGTGGAGA
2601 TTGCACCAGC GGCAGCTCTG AGTGCATGTG GTGCAGCAAC ATGAAGCAGT
2651 GTGTGGACTC CAATGCCTAT GTGGCCTCCT TCCCTTTTGG CCAGTGTATG

FIG. 8B

```
2701  GAATGGTATA CGATGAGCAC CTGCCCCCT GAAAATTGTT CAGGCTACTG
2751  TACCTGTAGT CATTGCTTGG AGCAACCAGG CTGTGGCTGG TGTACTGATC
2801  CCAGCAATAC TGGCAAAGGG AAATGCATAG AGGGTTCCTA TAAAGGACCA
2851  GTGAAGATGC CTTCGCAAGC CCCTACAGGA AATTTCTATC CACAGCCCT
2901  GCTCAATTCC AGCATGTGTC TAGAGGACAG CAGATACAAC TGGTCTTTCA
2951  TTCACTGTCC AGCTTGCCAA TGCAACGGCC ACAGTAAATG CATCAATCAG
3001  AGCATCTGTG AGAAGTGTGA GAACCTGACC ACAGGCAAGC ACTGCGAGAC
3051  CTGCATATCT GGCTTCTACG GTGATCCCAC CAATGGAGGG AAATGTCAGC
3101  CATGCAAGTG CAATGGGCAC GCGTCTCTGT GCAACACCAA CACGGGCAAG
3151  TGCTTCTGCA CCACCAAGGG CGTCAAGGGG GACGAGTGCC AGCTATGTGA
3201  GGTAGAAAAT CGATACCAAG GAAACCCTCT CAGAGGAACA TGTTATTATA
3251  CTCTTCTTAT TGACTATCAG TTCACCTTTA GTCTATCCCA GGAAGATGAT
3301  CGCTATTACA CAGCTATCAA TTTTGTGGCT ACTCCTGACG AACAAAACAG
3351  GGATTTGGAC ATGTTCATCA ATGCCTCCAA GAATTTCAAC CTCAACATCA
3401  CCTGGGCTGC CAGTTTCTCA GCTGGAACCC AGGCTGGAGA AGAGATGCCT
3451  GTTGTTTCAA AAACCAACAT TAAGGAGTAC AAAGATAGTT TCTCTAATGA
3501  GAAGTTTGAT TTCGCAACC ACCCAAATAT CACTTTCTTT GTTTATGTCA
3551  GTAATTTCAC CTGGCCCATC AAAATTCAGG TGCAAACTGA ACAATGA
```

FIG. 8C

| | | | | |
|---|---|---|---|---|
| 1 | MVAAAAATEA | RLRRRTAATA | ALAGRSGGPH | CVNGGRCNPG | TGQCVCPAGW |
| 51 | VGEQCQHCGG | RFRLTGSSGF | VTDGPGNYKY | KTKCTWLIEG | QPNRIMRLRF |
| 101 | NHFATECSWD | HLYVYDGDSI | YAPLVAAFSG | LIVPERDGNE | TVPEVVATSG |
| 151 | YALLHFFSDA | AYNLTGFNIT | YSFDMCPNNC | SGRGECKISN | SSDTVECECS |
| 201 | ENWKGEACDI | PHCTDNCGFP | HRGICNSSDV | RGCSCFSDWQ | GPGCSVPVPA |
| 251 | NQSFWTREEY | SNLKLPRASH | KAVVNGNIMW | VVGGYMFNHS | DYNMVLAYDL |
| 301 | ASREWLPLNR | SVNNVVVRYG | HSLALYKDKI | YMYGGKIDST | GNVTNELRVF |
| 351 | HIHNESWVLL | TPKAKEQYAV | VGHSAHIVTL | KNGRVVMLVI | FGHCPLYGYI |
| 401 | SNVQEYDLDK | NTWSILHTQG | ALVQGGYGHS | SVYDHRTRAL | YVHGGYKAFS |
| 451 | ANKYRLADDL | YRYDVDTQMW | TILKDSRFFR | YLHTAVIVSG | TMLVFGGNTH |
| 501 | NDTSMSHGAK | CFSSDFMAYD | IACDRWSVLP | RPDLHHDVNR | FGHSAVLHNS |
| 551 | TMYVFGGFNS | LLLSDILVFT | SEQCDAHRSE | AACLAAGPGI | RCVWNTGSSQ |
| 601 | CISWALATDE | QEEKLKSECF | SKRTLDHDRC | DQHTDCYSCT | ANTNDCHWCN |
| 651 | DHCVPRNHSC | SEGQISIFRY | ENCPKDNPMY | YCNKKTSCRS | CALDQNCQWE |
| 701 | PRNQECIALP | ENICGIGWHL | VGNSCLKITT | AKENYDNAKL | FCRNHNALLA |
| 751 | SLTTQKKVEF | VLKQLRIMQS | SQSMSKLTLT | PWVGLRKINV | SYWCWEDMSP |
| 801 | FTNSLLQWMP | SEPSDAGFCG | ILSEPSTRGL | KAATCINPLN | GSVCERPANH |
| 851 | SAKQCRTPCA | LRTACGDCTS | GSSECMWCSN | MKQCVDSNAY | VASFPFGQCM |
| 901 | EWYTMSTCPP | ENCSGYCTCS | HCLEQPGCGW | CTDPSNTGKG | KCIEGSYKGP |
| 951 | VKMPSQAPTG | NFYPQPLLNS | SMCLEDSRYN | WSFIHCPACQ | CNGHSKCINQ |
| 1001 | SICEKCENLT | TGKHCETCIS | GFYGDPTNGG | KCQPCKCNGH | ASLCNTNTGK |
| 1051 | CFCTTKGVKG | DECQLCEVEN | RYQGNPLRGT | CYYTLLIDYQ | FTFSLSQEDD |
| 1101 | RYYTAINFVA | TPDEQNRDLD | MFINASKNFN | LNITWAASFS | AGTQAGEEMP |
| 1151 | VVSKTNIKEY | KDSFSNEKFD | FRNHPNITFF | VYVSNFTWPI | KIQIAFSQHS |
| 1201 | NFMDLVQFFV | TFFSCFLSLL | LVAAVVWKIK | QSCWASRRRE | QLLREMQQMA |
| 1251 | SRPFASVNVA | LETDEEPPDL | IGGSIKTVPK | PIALEPCFGN | KAAVLSVFVR |
| 1301 | LPRGLGGIPP | PGQSGLAVAS | ALVDISQQMP | IVYKEKSGAV | RNRKQQPPAQ |
| 1351 | PGTCI | | | | |

FIG. 9

```
   1    atggtggccg cagccgcggc aactgaggca aggctgagga ggaggacggc
  51    ggcgacggca gcgctcgcgg gcaggagcgg cgggccgcac tgtgtcaacg
 101    gcggtcgctg caaccctggc accggccagt gcgtctgccc cgccggctgg
 151    gtgggcgagc aatgccagca ctgcggggcc cgcttcagac taactggatc
 201    ttctgggttt gtgacagatg gacctggaaa ttataaatac aaaacgaagt
 251    gcacgtggct cattgaagga cagccaaata gaataatgag acttcgtttc
 301    aatcattttg ctacagagtg tagttgggac catttatatg tttatgatgg
 351    ggactcaatt tatgcaccgc tagttgctgc atttagtggc tcattgttc
 401    ctgagagaga tggcaatgag actgtccctg aggttgttgc cacatcaggt
 451    tatgccttgc tgcattttt tagtgatgct gcttataatt tgactggatt
 501    taatattact tacagttttg atatgtgtcc aaataactgc tcaggccgag
 551    gagagtgtaa gatcagtaat agcagcgata ctgttgaatg tgaatgttct
 601    gaaaactgga aggtgaagc atgtgacatt cctcactgta cagacaactg
 651    tggttttcct catcgaggca tctgcaattc aagtgatgtc agaggatgct
 701    cctgcttctc agactggcag ggtcctggat gttcagttcc tgtaccagct
 751    aaccagtcat tttggactcg agaggaatat tctaacttaa agctccccag
 801    agcatctcat aaagctgtgg tcaatggaaa cattatgtgg gttgttggag
 851    gatatatgtt caaccactca gattataaca tggttctagc gtatgacctt
 901    gcttctaggg agtggcttcc actaaaccgt tctgtgaaca atgtggttgt
 951    tagatatggt cattctttgg cattatacaa ggataaaatt tacatgtatg
1001    gaggaaaaat tgattcaact gggaatgtga ccaatgagtt gagagttttt
1051    cacattcata atgagtcatg ggtgttgttg acccctaagg caaaggagca
1101    gtatgcagtg gttgggcact ctgcacacat tgttacactg aagaatggcc
1151    gagtggtcat gctggtcatc tttggtcact gccctctcta tggatatata
1201    agcaatgtgc aggaatatga tttggataag aacacatgga gtatattaca
1251    cacccagggt gcccttgtgc aaggggtta cggccatagc agtgtttacg
1301    accataggac cagggcccta tacgttcatg gtggctacaa ggctttcagt
1351    gccaataagt accggcttgc agatgatctc taccgatatg atgtggatac
1401    ccagatgtgg accattctta aggacagccg attttttccgt tacttgcaca
1451    cagctgtgat agtgagtgga accatgctgg tgtttggggg aaacacacac
1501    aatgacacat ctatgagcca tggcgccaaa tgcttctctt cagatttcat
1551    ggcctatgac attgcctgtg accgctggtc agtgcttccc agacctgatc
1601    tccaccatga tgtcaacaga tttggccatt cagcagtctt acacaacagc
1651    accatgtatg tgttcggtgg tttcaatagt ctcctcctca gcgacatcct
1701    ggtattcacc tcggaacagt gtgatgcgca tcggagtgaa gccgcttgtt
1751    tagcagcagg acctggtatt cggtgtgtgt ggaacacagg gtcgtctcag
1801    tgtatctcgt gggcgctggc aactgatgaa caagaagaaa agttaaaatc
1851    agaatgtttt tccaaaagaa ctcttgacca tgacagatgt gaccagcaca
1901    cagattgtta cagctgcaca gccaacacca atgactgcca ctggtgcaat
1951    gaccattgtg tccccaggaa ccacagctgc tcagaaggcc agatctccat
2001    ttttaggtat gagaattgcc caaggataa ccctatgtac tactgtaaca
2051    agaagaccag ctgcaggagc tgtgccctgg accagaactg ccagtgggag
2101    ccccggaatc aggagtgcat tgccctgccc gaaaatatct gtggcattgg
2151    ctggcatttg gttggaaact catgtttgaa aattactact gccaaggaga
2201    attatgacaa tgctaaattg ttctgtagga accacaatgc ccttttggct
2251    tctcttacaa cccagaagaa ggtagaattt gtccttaagc agctgcgaat
2301    aatgcagtca tctcagagca tgtccaagct caccttaacc ccatgggtcg
2351    gccttcggaa gatcaatgtg tcctactggt gctgggaaga tatgtcccca
2401    tttacaaaata gtttactaca gtggatgccg tctgagccca gtgatgctgg
2451    attctgtgga attttatcag aacccagtac tcggggactg aaggctgcaa
2501    cctgcatcaa cccactcaat ggtagtgtct gtgaaaggcc tgcaaaccac
2551    agtgctaagc agtgccggac accatgtgcc tgaggacag catgtggaga
2601    ttgcaccagc ggcagctctg agtgcatgtg gtgcagcaac atgaagcagt
```

FIG. 10A

```
2651  gtgtggactc caatgcctat gtggcctcct tcccttttgg ccagtgtatg
2701  gaatggtata cgatgagcac ctgccccct gaaaattgtt caggctactg
2751  tacctgtagt cattgcttgg agcaaccagg ctgtggctgg tgtactgatc
2801  ccagcaatac tggcaaaggg aaatgcatag agggttccta taaaggacca
2851  gtgaagatgc cttcgcaagc ccctacagga aatttctatc cacagcccct
2901  gctcaattcc agcatgtgtc tagaggacag cagatacaac tggtctttca
2951  ttcactgtcc agcttgccaa tgcaacggcc acagtaaatg catcaatcag
3001  agcatctgtg agaagtgtga gaacctgacc acaggcaagc actgcgagac
3051  ctgcatatct ggcttctacg gtgatccac caatggaggg aaatgtcagc
3101  catgcaagtg caatgggcac ccgtctctgt gcaacaccaa cacgggcaag
3151  tgcttctgca ccaccaaggg cgtcaagggg gacgagtgcc agctatgtga
3201  ggtagaaaat cgataccaag gaaaccctct cagaggaaca tgttattata
3251  ctcttcttat tgactatcag ttcacccttta gtctatccca ggaagatgat
3301  cgctattaca cagctatcaa ttttgtggct actcctgacg aacaaaacag
3351  ggatttggac atgttcatca atgcctccaa gaatttcaac ctcaacatca
3401  cctgggctgc cagtttctca gctggaaccc aggctggaga agagatgcct
3451  gttgtttcaa aaaccaacat taaggagtac aaagatagtt tctctaatga
3501  gaagtttgat tttcgcaacc acccaaatat cactttcttt gtttatgtca
3551  gtaatttcac ctggcccatc aaaattcaga ttgccttctc tcagcacagc
3601  aattttatgg acctggtaca gttcttcgtg actttcttca gttgtttcct
3651  ctctttgctc ctggtggctg ctgtggtttg gaagatcaaa caaagttgtt
3701  gggcctccag acgtagagag caacttcttc gagagatgca acagatggcc
3751  agccgtccct tgcctctgt aaatgtcgcc ttggaaacag atgaggagcc
3801  tcctgatctt attggggga gtataaagac tgttcccaaa cccattgcac
3851  tggagccgtg ttttggcaac aaagccgctg tcctctctgt gtttgtgagg
3901  ctccctcgag gcctgggtgg catccctcct cctgggcagt caggtcttgc
3951  tgtggccagc gccctggtgg acatttctca gcagatgccg atagtgtaca
4001  aggagaagtc aggagccgtg agaaaccgga agcagcagcc ccctgcacag
4051  cctgggacct gcatctga
```

FIG. 10B

MVAAAAATEARLRRRTAATAALAGRSGGPHWDWDVTRAGRPGLGAGLRLPRLLSPPLR
PRLLLLLLLLPPPLLLLLLPCEAEAAAAAAVSGSAAAEAKECDRPCVNGGRCNPGTG
QCVCPAGWVGEQCQHCGGRFRLTGSSGFVTDGPGNYKYKTKCTWLIEGQPNRIMRLRF
NHFATECSWDHLYVYDGDSIYAPLVRAFSGLIVPERDGNETVPEVVATSGYALLHFFS
DAAYNLTGFNITYSFDMCPNNCSGRGECKISNSSETVECECSENWKGEACDIPHCTDN
CGFPHRGICNSSDVRGCSCFSDWQGFGCSVPVPANQSFWTREEYSNLKLPRASHKAVV
NGNIMWVVGGYMFNHSDYNMVLAYDLASREWLPLNRSVNNVVVRYGHSLALYKDKIYM
YGGKIDPTGNVTNELRVFHIHNESWVLLTPKAKEQYAVVGHSAHIVTLKNGRVVMLVI
FGHCPLYGYISNVQEYDLDKNTWSILHTQGALVQGGYGHSSVYDHRTRALYVHGGYKA
FSANKYRLADDLYRYDVDTQMWTILHDSRFFRYLHTAVIVSGTMLVFGGNTHNDTSMS
HGAKCFSSDFMAYDIACDRWSVLPRFDLHHDVNRFGHSAVLHNSTMYVFGGFNSLLLS
DILVFTSEQCDAHRSEAACLAAGPGIRCVWNTGSSQCISWALAIDEQEEKLKSECFSK
RTLDHDRCDQHTDCYSCTANTNDCHWCNDHCVPRNHSCSEGQISIFRYENCPKDNPMY
YCNKKTSCRSCALDQNCQWEPRNQECIALPENICGIGWHLVGNSCLKITTAKENYDNA
KLFCRNHNALLASLTTQKKVEFVLKQLRIMQSSQSMSKLTLTPWVGLRKINVSYWCWE
DMSPFTNSLLQWMPSEPSDAGFCGILSEPSTRGLKAATCINPLNGSVCERPANHSAKQ
CRTPCALRTACGDCTSGSSECMWCSNMKQCVDSNAYVASFPFGQCMEWYTMSTCPPEN
CSGYCTCSHCLEQPGCGWCTDPSNTGKGKCIEGSYKGPVKMPSQAPTGNFYPQPLLNS
SMCLEDSRYNWSFIHCPACQCNGHSKCINQSICEKCENLTTGKHCETCISGFYGDPTN
GGKCQPCKCNGHASLCNTNTGKCFCTTKGVKGDECQLCEVENRYQGNPLRGTCYYTLL
IDYQFTFSLSQEDDRYYTAINFVATPDEQNRDLDMFINASKNFNLNITWAASFSAGTQ
AGEEMPVVSKTNIKEYKDSFSNEKFDFRNHPNITFFVYVSNFTWPIKIQVQTEQ

FIG. 11

```
   1  atggtggccg cagcggcggc aactgaggca aggctgagga ggaggacggc ggcgacggca
  61  gcgctcgcgg gcaggagcgg cgggccgcac tgggactggg acgtgaccag ggctgggagg
 121  ccggggctgg gggccgggct gcgcctcccg cggctgctgt ctccaccgct gcggccacgg
 181  ctgctgctgc tgctgttgtt gctcccgccg ccgctgttgc tgctgctgct gccctgtgag
 241  gccgaggccg cggcggcggc ggcggcggtg tcgggctcag ccgcagccga ggccaaggaa
 301  tgtgaccggc cctgtgtcaa cggcggtcgc tgcaaccctg gcaccggcca gtgcgtctgc
 361  cccgccggct gggtgggcga gcaatgccag cactgcgggg gccgcttcag actaactgga
 421  tcttctgggt ttgtgacaga tggacctgga aattataaat acaaaacgaa gtgcacgtgg
 481  ctcattgaag gacagccaaa tagaataatg agacttcgtt tcaatcattt tgctacagag
 541  tgtagttggg accatttata tgtttatgat ggggactcaa tttatgcacc gctagttgct
 601  gcatttagtg gcctcattgt tcctgagaga gatggcaatg agactgtccc tgaggttgtt
 661  gccacatcag gttatgcctt gctgcatttt tttagtgatg ctgcttataa tttgactgga
 721  tttaatatta cttacagttt tgatatgtgt ccaaataact gctcaggccg aggagagtgt
 781  aagatcagta atagcagcga aactgttgaa tgtgaatgtt ctgaaaactg gaaaggtgaa
 841  gcatgtgaca ttcctcactg tacagacaac tgtggttttc ctcatcgagg catctgcaat
 901  tcaagtgatg tcagaggatg ctcctgcttc tcagactggc agggtcctgg atgttcagtt
 961  cctgtaccag ctaaccagtc attttggact cgagaggaat attctaactt aaagctcccc
1021  agagcatctc ataaagctgt ggtcaatgga aacattatgt gggttgttgg aggatatatg
1081  ttcaaccact cagattataa catggttcta gcgtatgacc ttgcttctag ggagtggctt
1141  ccactaaacc gttctgtgaa caatgtggtt gttagatatg tcattctttt ggcattatac
1201  aaggataaaa tttacatgta tggaggaaaa attgatccaa ctgggaatgt gaccaatgag
1261  ttgagagttt ttcacattca taatgagtca tgggtgttgt tgaccctaa ggcaaggag
1321  cagtatgcag tggttgggca ctctgcacac attgttacac tgaagaatgg ccgagtggtc
1381  atgctggtca tctttggtca ctgccctctc tatggatata taagcaatgt gcaggaatat
1441  gatttggata agaacacatg gagtatatta cacacccagg gtgcccttgt gcaaggggt
1501  tacggccata gcagtgttta cgaccatagg accagggccc tatacgttca tggtggctac
1561  aaggctttca gtgccaataa gtaccggctc gcagatgatc tctaccgata tgatgtggat
1621  acccagatgt ggaccattct taaggacagc cgatttttcc gttacttgca cacagctgtg
1681  atagtgagtg gaaccatgct ggtgtttggg ggaaacacac acaatgacac atctatgagc
1741  catggcgcca aatgcttctc ttcagatttc atggcctatg acattgcctg tgaccgctgg
1801  tcagtgcttc ccagacctga tctccaccat gatgtcaaca gatttggcca ttcagcagtc
1861  ttacacaaca gcaccatgta tgtgttcggt ggtttcaata gtctcctcct cagcgacatc
1921  ctggtattca cctcggaaca gtgtgatgcg catcggagtg aagccgcttg tttagcagca
1981  ggaccTggta ttcggtgtgt gtggaacaca gggtcgtctc agtgtatctc gtgggcgctg
2041  gcaactgatg aacaagaaga aagttaaaa tcagaatgtt tttccaaaag aactcttgac
2101  catgacagat gtgaccagca cacagattgt tacagctgta cagccaacac caatgactgc
2161  cactggtgca atgaccattg tgtccccagg aaccacagct gctcagaagg ccagatctcc
2221  attttttaggt atgagaattg ccccaaggat aacccatgt actactgtaa caagaagacc
2281  agctgcagga gctgtgccct ggaccagaac tgccagtggg agccccggaa tcaggagtgc
2341  attgccctgc ccgaaaatat ctgtggcatt ggctggcatt tggttggaaa ctcatgtttg
2401  aaaattacta ctgccaagga gaattatgaa aatgctaaat tgttctgtag gaaccacaat
2461  gcccttttgg ctctctctac aacccagaag aaggtagaat ttgtccttaa gcagctgcga
2521  ataatgcagt catctcagag catgtccaag ctcaccttaa cccatggt cggccttcgg
2581  aagatcaatg tgtcctactg gtgctgggaa gatatgtccc catttacaaa tagtttacta
2641  cagtggatgc cgtctgagcc cagtgatgct ggattctgtg aatttttatc agaacccagt
2701  actcggggac tgaaggctgc aacctgcatc aacccactca atggtagtgt ctgtgaaagg
2761  cctgcaaacc acagtgctaa gcagtgccgg acaccatgtg ccttgaggac agcatgtgga
2821  gattgcacca gcggcagctc tgagtgcatg tggtgcagca acatgaagca gtgtgtggac
2881  tccaatgcct atgtggcctc cttcccttt ggccagtgta tggaatggta tgatgagc
2941  acctgcccc ctgaaaattg ttcaggctac tgtacctgta gtcattgctt ggagcaacca
3001  ggctgtggct ggtgtactga tcccagcaat actggcaaag gaaatgcat agagggttcc
3061  tataaaggac cagtgaagat gccttgcaa gccctacag gaaatttcta tccacagccc
3121  ctgctcaatt ccagcatgtg tctagaggac agcagataca actggtcttt cattcactgt
3181  ccagcttgcc aatgcaacgg ccacagtaaa tgcatcaatc agagcatctg tgagaagtgt
3241  gagaacctga ccacaggcaa gcactgcgag acctgcatat ctggcttcta cggtgatccc
3301  accaatggag ggaaatgtca gccatgaag tgcaatgggc acgcgtctct gtgcaacacc
3361  aacacgggca agtgcttctg caccaccaag ggcgtcaagg gggacgagtg ccagctatgt
3421  gaggtagaaa atcgatacca aggaaacccc ctcagaggaa catgttatta tactcttctt
3481  attgactatc agttcacctt tagtctatcc caggaagatg atcgctatta cacagctatc
3541  aattttgtgg ctactccctga cgaacaaaac agggatttgg acatgttcat caatgcctcc
3601  aagaatttca acctcaacat cacctgggct gccagttttct cagctggaac ccaggctgga
3661  gaagagatgc ctgttgttc aaaaaccaac attaaggagt acaagagatag tttctctaat
3721  gagaagtttg attttcgcaa ccacccaaat atcactttct ttgtttatgt cagtaatttc
3781  acctggccca tcaaaattca ggtgcaaact gaacaatga
```

FIG. 12

```
   1  MVAAAAATEA  RLRRRTAATA  ALAGRSGGPH  WDWDVTRAGR  PGLGAGLRLP
  51  RLLSPPLRPR  LLLLLLLLPP  PLLLLLLPCE  AEAAAAAAAV  SGSAAAEAKE
 101  CDRPCVNGGR  CNPGTGQCVC  PAGWVGEQCQ  HCGGRFRLTG  SSGFVTDGPG
 151  NYKYKTKCTW  LIEGQPNRIM  RLRFNHFATE  CSWDHLYVYD  GDSIYAPLVA
 201  AFSGLIVPER  DGNETVPEVV  ATSGYALLHF  FSDAAYNLTG  FNITYSFDMC
 251  PNNCSGRGEC  KISNSSETVE  CECSENWKGE  ACDIPHCTDN  CGFPHRGICN
 301  SSDVRGCSCF  SDWQGPGCSV  PVPANQSFWT  REEYSNLKLP  RASHKAVVNG
 351  NIMWVVGGYM  FNHSDYNMVL  AYDLASREWL  PLNRSVNNVV  VRYGHSLALY
 401  KDKIYMYGGK  IDPTGNVTNE  LRVFHIHNES  WVLLTPKAKE  QYAVVGHSAH
 451  IVTLKNGRVV  MLVIFGHCPL  YGYISNVQEY  DLDKNTWSIL  HTQGALVQGG
 501  YGHSSVYDHR  TRALYVHGGY  KAFSANKYRL  ADDLYRYDVD  TQMWTILKDS
 551  RFFRYLHTAV  IVSGTMLVFG  GNTHNDTSMS  HGAKCFSSDF  MAYDIACDRW
 601  SVLPRPDLHH  DVNRFGHSAV  LHNSTMYVFG  GFNSLLLSDI  LVFTSEQCDA
 651  HRSEAACLAA  GPGIRCVWNT  GSSQCISWAL  ATDEQEEKLK  SECFSKRTLD
 701  HDRCDQHTDC  YSCTANTNDC  HWCNDHCVPR  NHSCSEGQIS  IFRYENCPKD
 751  NPMYYCNKKT  SCRSCALDQN  CQWEPRNQEC  IALPENICGI  GWHLVGNSCL
 801  KITTAKENYD  NAKLFCRNHN  ALLASLTTQK  KVEFVLKQLR  IMQSSQSMSK
 851  LTLTPWVGLR  KINVSYWCWE  DMSPFTNSLL  QWMPSEPSDA  GFCGILSEPS
 901  TRGLKAATCI  NPLNGSVCER  PANHSAKQCR  TPCALRTACG  DCTSGSSECM
 951  WCSNMKQCVD  SNAYVASFPF  GQCMEWYTMS  TCPPENCSGY  CTCSHCLEQP
1001  GCGWCTDPSN  TGKGKCIEGS  YKGPVKMPSQ  APTGNFYPQP  LLNSSMCLED
1051  SRYNWSFIHC  PACQCNGHSK  CINQSICEKC  ENLTTGKHCE  TCISGFYGDP
1101  TNGGKCQPCK  CNGHASLCNT  NTGKCFCTTK  GVKGDECQLC  EVENRYQGNP
1151  LRGTCYYTLL  IDYQFTFSLS  QEDDRYYTAI  NFVATPDEQN  RDLDMFINAS
1201  KNFNLNITWA  ASFSAGTQAG  EEMPVVSKTN  IKEYKDSFSN  EKFDFRNHPN
1251  ITFFVYVSNF  TWPIKIQIAF  SQHSNFMDLV  QFFVTFFSCF  LSLLLVAAVV
1301  WKIKQSCWAS  RRREQLLREM  QQMASRPFAS  VNVALETDEE  PPDLIGGSIK
1351  TVPKPIALEP  CFGNKAAVLS  VFVRLPRGLG  GIPPPGQSGL  AVASALVDIS
1401  QQMPIVYKEK  SGAVRNRKQQ  PPAQPGTCI
```

FIG. 13

```
   1  atggtggccg cagcggcggc aactgaggca aggctgagga ggaggacggc
  51  ggcgacggca gcgctcgcgg gcaggagcgg cgggccgcac tgggactggg
 101  acgtgaccag ggctggagg ccggggctgg gggccgggct gcgcctcccg
 151  cggctgctgt ctccaccgct gcggccacgg ctgctgctgc tgctgttgtt
 201  gctcccgccg ccgctgttgc tgctgctgct gccctgtgag gccgaggccg
 251  cggcggcggc ggcggcggtg tcgggctcag ccgcagccga ggccaaggaa
 301  tgtgaccggc cctgtgtcaa cggcggtcgc tgcaaccctg gcaccggcca
 351  gtgcgtctgc cccgccggct gggtgggcga gcaatgccag cactgcgggg
 401  gccgcttcag actaactgga tcttctgggt tgtgacaga tggacctgga
 451  aattataaat acaaaacgaa gtgcacgtgg ctcattgaag gacagccaaa
 501  tagaataatg agacttcgtt tcaatcattt gctacagag tgtagttggg
 551  accatttata tgtttatgat ggggactcaa tttatgcacc gctagttgct
 601  gcatttagtg gcctcattgt tcctgagaga gatggcaatg agactgtccc
 651  tgaggttgtt gccacatcag gttatgcctt gctgcatttt tttagtgatg
 701  ctgcttataa tttgactgga tttaatatta cttacagttt tgatatgtgt
 751  ccaaataact gctcaggccg aggagagtgt aagatcagta atagcagcga
 801  aactgttgaa tgtgaatgtt ctgaaaactg gaaaggtgaa gcatgtgaca
 851  ttcctcactg tacagacaac tgtggttttc ctcatcgagg catctgcaat
 901  tcaagtgatg tcaggatg ctcctgcttc tcagactggc agggtcctgg
 951  atgttcagtt cctgtaccag ctaaccagtc attttggact cgagaggaat
1001  attctaactt aaagctcccc agagcatctc ataaagctgt ggtcaatgga
1051  aacattatgt gggttgttgg aggatatatg ttcaaccact cagattataa
1101  catggttcta gcgtatgacc ttgcttctag ggagtggctt ccactaaacc
1151  gttctgtgaa caatgtggtt gttagatatg gtcattcttt ggcattatac
1201  aaggataaaa tttacatgta tggaggaaaa attgatccaa ctgggaatgt
1251  gaccaatgag ttgagagttt tcacattca taatgagtca tgggtgttgt
1301  tgaccctaa ggcaaggag cagtatgcag tggttgggca ctctgcacac
1351  attgttacac tgaagaatgg ccgagtggtc atgctggtca tctttggtca
1401  ctgccctctc tatggatata taagcaatgt gcaggaatat gatttggata
1451  agaacacatg gagtatatta cacacccagg gtgcccttgt gcaaggggt
1501  tacggccata gcagtgttta cgaccatagg accagggccc tatacgttca
1551  tggtggctac aaggctttca gtgccaataa gtaccggctt gcagatgatc
1601  tctaccgata tgatgtggat acccagatgt ggaccattct taaggacagc
1651  cgattttttcc gttacttgca cacagctgtg atagtgagtg aaccatgct
1701  ggtgtttggg ggaaacacac acaatgacac atctatgagc catggcgcca
1751  aatgcttctc ttcagatttc atggcctatg acattgcctg tgaccgctgg
1801  tcagtgcttc ccagacctga tctccaccat gatgtcaaca gatttggcca
1851  ttcagcagtc ttacacaaca gcaccatgta tgttcggt ggtttcaata
1901  gtctcctcct cagcgacatc ctggtattca cctcggaaca gtgtgatgcg
1951  catcggagtg aagccgcttg tttagcagca ggacctggta ttcggtgtgt
2001  gtggaacaca gggtcgtctc agtgtatctc gtgggcgctg gcaactgatg
2051  aacaagaaga aaagttaaaa tcagaatgtt tttccaaaag aactcttgac
2101  catgacagat gtgaccagca cacagattgt tacagctgta cagccaacac
2151  caatgactgc cactggtgca atgaccattg tgtccccagg aaccacagct
2201  gctcagaagg ccagatctcc atttttaggt atgagaattg ccccaaggat
2251  aaccccatgt actactgtaa caagaagacc agctgcagga gctgtgccct
2301  ggaccagaac tgccagtggg agccccggaa tcaggagtgc attgccctgc
2351  ccgaaaatat ctgtggcatt ggctggcatt tggttggaaa ctcatgtttg
2401  aaaattacta ctgccaagga gaattatgac aatgctaaat tgttctgtag
2451  gaaccacaat gccctttgg cttctcttac aacccagaag aaggtagaat
2501  ttgtccttaa gcagctgcga ataatgcagt catctcagag catgtccaag
2551  ctcacccttaa ccccatgggt cggccttcgg aagatcaatg tgtcctactg
2601  gtgctgggaa gatatgtccc catttacaaa tagtttacta cagtggatgc
```

FIG. 14A

```
2651  cgtctgagcc cagtgatgct ggattctgtg gaatttatc agaacccagt
2701  actcggggac tgaaggctgc aacctgcatc aacccactca atggtagtgt
2751  ctgtgaaagg cctgcaaacc acagtgctaa gcagtgccgg acaccatgtg
2801  ccttgaggac agcatgtgga gattgcacca gcggcagctc tgagtgcatg
2851  tggtgcagca acatgaagca gtgtgtggac tccaatgcct atgtggcctc
2901  cttccctttt ggccagtgta tggaatggta tacgatgagc acctgccccc
2951  ctgaaaattg ttcaggctac tgtacctgta gtcattgctt ggagcaacca
3001  ggctgtggct ggtgtactga tcccagcaat actggcaaag gaaatgcat
3051  agagggttcc tataaaggac cagtgaagat gccttcgcaa gccctacag
3101  gaaatttcta tccacagccc ctgctcaatt ccagcatgtg tctagaggac
3151  agcagataca actggtcttt cattcactgt ccagcttccc aatgcaacgg
3201  ccacagtaaa tgcatcaatc agagcatctg tgagaagtgt gagaacctga
3251  ccacaggcaa gcactgcgag acctgcatat ctggcttcta cggtgatccc
3301  accaatggag ggaaatgtca gccatgcaag tgcaatgggc acgcgtctct
3351  gtgcaacacc aacacgggca agtgcttctg caccaccaag ggcgtcaagg
3401  gggacgagtg ccagctatgt gaggtagaaa atcgatacca aggaaaccct
3451  ctcagaggaa catgttatta tactcttctt attgactatc agttcacctt
3501  tagtctatcc caggaagatg atcgctatta cacagctatc aatttgtgg
3551  ctactcctga cgaacaaaac agggatttgg acatgttcat caatgcctcc
3601  aagaatttca acctcaacat caccctgggct gccagtttct cagctggaac
3651  ccaggctgga gaagagatgc ctgttgtttc aaaaaccaac attaaggagt
3701  acaaagatag tttctctaat gagaagtttg attttcgcaa ccacccaaat
3751  atcactttct ttgtttatgt cagtaattc acctggccca tcaaaattca
3801  gattgccttc tctcagcaca gcaatttat ggacctggta cagttcttcg
3851  tgactttctt cagttgtttc ctctcttgc tcctggtggc tgctgtggtt
3901  tggaagatca aacaaagttg ttgggcctcc agacgtagag agcaacttct
3951  tcgagagatg caacagatgg ccagccgtcc ctttgcctct gtaaatgtcg
4001  ccttggaaac agatgaggag cctcctgatc ttattggggg gagtataaag
4051  actgttccca aacccattgc actggagccg tgttttggca acaaagccgc
4101  tgtcctctct gtgttgtga ggctccctcg aggcctgggt ggcatccctc
4151  ctcctgggca gtcaggtctt gctgtggcca gcgccctggt ggacatttct
4201  cagcagatgc cgatagtgta caaggagaag tcaggagccg tgagaaaccg
4251  gaagcagcag cccctgcac agcctgggac ctgcatctga
```

FIG. 14B

SEQUENCE LISTING

```
<160> NUMBER OF SEQ ID NOS: 25

<210> SEQ ID NO 1
<211> LENGTH: 3597
<212> TYPE: DNA
<213> ORGANISM: Homo sapiens
<220> FEATURE:
<221> NAME/KEY: CDS
<222> LOCATION: (1)...(3594)
```

<400> SEQUENCE: 1

| | | | | | | | | | | | | | | | | |
|---|---|---|---|---|---|---|---|---|---|---|---|---|---|---|---|---|
| atg | gtg | gcc | gca | gcg | gcg | gca | act | gag | gca | agg | ctg | agg | agg | agg | acg | 48 |
| Met | Val | Ala | Ala | Ala | Ala | Thr | Glu | Ala | Arg | Leu | Arg | Arg | Arg | Thr | | |
| 1 | | | | 5 | | | | | 10 | | | | | 15 | | |
| gcg | gcg | acg | gca | gcg | ctc | gcg | ggc | agg | agc | ggc | ggg | ccg | cac | tgt | gtc | 96 |
| Ala | Ala | Thr | Ala | Ala | Leu | Ala | Gly | Arg | Ser | Gly | Gly | Pro | His | Cys | Val | |
| | | | 20 | | | | | 25 | | | | | 30 | | | |
| aac | ggc | ggt | cgc | tgc | aac | cct | ggc | acc | ggc | cag | tgc | gtc | tgc | ccc | gcc | 144 |
| Asn | Gly | Gly | Arg | Cys | Asn | Pro | Gly | Thr | Gly | Gln | Cys | Val | Cys | Pro | Ala | |
| | | 35 | | | | | 40 | | | | | 45 | | | | |
| ggc | tgg | gtg | ggc | gag | caa | tgc | cag | cac | tgc | ggg | ggc | cgc | ttc | aga | cta | 192 |
| Gly | Trp | Val | Gly | Glu | Gln | Cys | Gln | His | Cys | Gly | Gly | Arg | Phe | Arg | Leu | |
| | 50 | | | | | 55 | | | | | 60 | | | | | |
| act | gga | tct | tct | ggg | ttt | gtg | aca | gat | gga | cct | gga | aat | tat | aaa | tac | 240 |
| Thr | Gly | Ser | Ser | Gly | Phe | Val | Thr | Asp | Gly | Pro | Gly | Asn | Tyr | Lys | Tyr | |
| 65 | | | | | 70 | | | | | 75 | | | | | 80 | |
| aaa | acg | aag | tgc | acg | tgg | ctc | att | gaa | gga | cag | cca | aat | aga | ata | atg | 288 |
| Lys | Thr | Lys | Cys | Thr | Trp | Leu | Ile | Glu | Gly | Gln | Pro | Asn | Arg | Ile | Met | |
| | | | | 85 | | | | | 90 | | | | | 95 | | |
| aga | ctt | cgt | ttc | aat | cat | ttt | gct | aca | gag | tgt | agt | tgg | gac | cat | tta | 336 |
| Arg | Leu | Arg | Phe | Asn | His | Phe | Ala | Thr | Glu | Cys | Ser | Trp | Asp | His | Leu | |
| | | | 100 | | | | | 105 | | | | | 110 | | | |
| tat | gtt | tat | gat | ggg | gac | tca | att | tat | gca | ccg | cta | gtt | gct | gca | ttt | 384 |
| Tyr | Val | Tyr | Asp | Gly | Asp | Ser | Ile | Tyr | Ala | Pro | Leu | Val | Ala | Ala | Phe | |
| | | 115 | | | | | 120 | | | | | 125 | | | | |
| agt | ggc | ctc | att | gtt | cct | gag | aga | gat | ggc | aat | gag | act | gtc | cct | gag | 432 |
| Ser | Gly | Leu | Ile | Val | Pro | Glu | Arg | Asp | Gly | Asn | Glu | Thr | Val | Pro | Glu | |
| | 130 | | | | | 135 | | | | | 140 | | | | | |
| gtt | gtt | gcc | aca | tca | ggt | tat | gcc | ttg | ctg | cat | ttt | ttt | agt | gat | gct | 480 |
| Val | Val | Ala | Thr | Ser | Gly | Tyr | Ala | Leu | Leu | His | Phe | Phe | Ser | Asp | Ala | |
| 145 | | | | | 150 | | | | | 155 | | | | | 160 | |
| gct | tat | aat | ttg | act | gga | ttt | aat | att | act | tac | agt | ttt | gat | atg | tgt | 528 |
| Ala | Tyr | Asn | Leu | Thr | Gly | Phe | Asn | Ile | Thr | Tyr | Ser | Phe | Asp | Met | Cys | |
| | | | | 165 | | | | | 170 | | | | | 175 | | |
| cca | aat | aac | tgc | tca | ggc | cga | gga | gag | tgt | aag | atc | agt | aat | agc | agc | 576 |
| Pro | Asn | Asn | Cys | Ser | Gly | Arg | Gly | Glu | Cys | Lys | Ile | Ser | Asn | Ser | Ser | |
| | | | 180 | | | | | 185 | | | | | 190 | | | |
| gat | act | gtt | gaa | tgt | gaa | tgt | tct | gaa | aac | tgg | aaa | ggt | gaa | gca | tgt | 624 |
| Asp | Thr | Val | Glu | Cys | Glu | Cys | Ser | Glu | Asn | Trp | Lys | Gly | Glu | Ala | Cys | |
| | | 195 | | | | | 200 | | | | | 205 | | | | |
| gac | att | cct | cac | tgt | aca | gac | aac | tgt | ggt | ttt | cct | cat | cga | ggc | atc | 672 |
| Asp | Ile | Pro | His | Cys | Thr | Asp | Asn | Cys | Gly | Phe | Pro | His | Arg | Gly | Ile | |
| | 210 | | | | | 215 | | | | | 220 | | | | | |
| tgc | aat | tca | agt | gat | gtc | aga | gga | tgc | tcc | tgc | ttc | tca | gac | tgg | cag | 720 |
| Cys | Asn | Ser | Ser | Asp | Val | Arg | Gly | Cys | Ser | Cys | Phe | Ser | Asp | Trp | Gln | |
| 225 | | | | | 230 | | | | | 235 | | | | | 240 | |
| ggt | cct | gga | tgt | tca | gtt | cct | gta | cca | gct | aac | cag | tca | ttt | tgg | act | 768 |
| Gly | Pro | Gly | Cys | Ser | Val | Pro | Val | Pro | Ala | Asn | Gln | Ser | Phe | Trp | Thr | |
| | | | | 245 | | | | | 250 | | | | | 255 | | |
| cga | gag | gaa | tat | tct | aac | tta | aag | ctc | ccc | aga | gca | tct | cat | aaa | gct | 816 |
| Arg | Glu | Glu | Tyr | Ser | Asn | Leu | Lys | Leu | Pro | Arg | Ala | Ser | His | Lys | Ala | |
| | | | | 260 | | | | | 265 | | | | | 270 | | |
| gtg | gtc | aat | gga | aac | att | atg | tgg | gtt | gtt | gga | gga | tat | atg | ttc | aac | 864 |
| Val | Val | Asn | Gly | Asn | Ile | Met | Trp | Val | Val | Gly | Gly | Tyr | Met | Phe | Asn | |
| | | | 275 | | | | | 280 | | | | | 285 | | | |
| cac | tca | gat | tat | aac | atg | gtt | cta | gcg | tat | gac | ctt | gct | tct | agg | gag | 912 |
| His | Ser | Asp | Tyr | Asn | Met | Val | Leu | Ala | Tyr | Asp | Leu | Ala | Ser | Arg | Glu | |
| | 290 | | | | | 295 | | | | | 300 | | | | | |
| tgg | ctt | cca | cta | aac | cgt | tct | gtg | aac | aat | gtg | gtt | gtt | aga | tat | ggt | 960 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Trp | Leu | Pro | Leu | Asn | Arg | Ser | Val | Asn | Val | Val | Arg | Tyr | Gly |     |     |      |
| 305 |     |     |     | 310 |     |     |     | 315 |     |     |     | 320 |     |     |     |      |

```
cat tct ttg gca tta tac aag gat aaa att tac atg tat gga gga aaa      1008
His Ser Leu Ala Leu Tyr Lys Asp Lys Ile Tyr Met Tyr Gly Gly Lys
            325                 330                 335 att gat tca act ggg aat gtg acc aat gag ttg aga gtt ttt cac att      1056
Ile Asp Ser Thr Gly Asn Val Thr Asn Glu Leu Arg Val Phe His Ile
                340                 345                 350 cat aat gag tca tgg gtg ttg ttg acc cct aag gca aag gag cag tat      1104
His Asn Glu Ser Trp Val Leu Leu Thr Pro Lys Ala Lys Glu Gln Tyr
            355                 360                 365 gca gtg gtt ggg cac tct gca cac att gtt aca ctg aag aat ggc cga      1152
Ala Val Val Gly His Ser Ala His Ile Val Thr Leu Lys Asn Gly Arg
370                 375                 380 gtg gtc atg ctg gtc atc ttt ggt cac tgc cct ctc tat gga tat ata      1200
Val Val Met Leu Val Ile Phe Gly His Cys Pro Leu Tyr Gly Tyr Ile
385                 390                 395                 400 agc aat gtg cag gaa tat gat ttg gat aag aac aca tgg agt ata tta      1248
Ser Asn Val Gln Glu Tyr Asp Leu Asp Lys Asn Thr Trp Ser Ile Leu
                405                 410                 415 cac acc cag ggt gcc ctt gtg caa ggg ggt tac ggc cat agc agt gtt      1296
His Thr Gln Gly Ala Leu Val Gln Gly Gly Tyr Gly His Ser Ser Val
            420                 425                 430 tac gac cat agg acc agg gcc cta tac gtt cat ggt ggc tac aag gct      1344
Tyr Asp His Arg Thr Arg Ala Leu Tyr Val His Gly Gly Tyr Lys Ala
            435                 440                 445 ttc agt gcc aat aag tac cgg ctt gca gat gat ctc tac cga tat gat      1392
Phe Ser Ala Asn Lys Tyr Arg Leu Ala Asp Asp Leu Tyr Arg Tyr Asp
450                 455                 460 gtg gat acc cag atg tgg acc att ctt aag gac agc cga ttt ttc cgt      1440
Val Asp Thr Gln Met Trp Thr Ile Leu Lys Asp Ser Arg Phe Phe Arg
465                 470                 475                 480 tac ttg cac aca gct gtg ata gtg agt gga acc atg ctg gtg ttt ggg      1488
Tyr Leu His Thr Ala Val Ile Val Ser Gly Thr Met Leu Val Phe Gly
                485                 490                 495 gga aac aca cac aat gac aca tct atg agc cat ggc gcc aaa tgc ttc      1536
Gly Asn Thr His Asn Asp Thr Ser Met Ser His Gly Ala Lys Cys Phe
            500                 505                 510 tct tca gat ttc atg gcc tat gac att gcc tgt gac cgc tgg tca gtg      1584
Ser Ser Asp Phe Met Ala Tyr Asp Ile Ala Cys Asp Arg Trp Ser Val
            515                 520                 525 ctt ccc aga cct gat tcc acc atg atg tca aca gat ttg gcc att cca      1632
Leu Pro Arg Pro Asp Ser Thr Met Met Ser Thr Asp Leu Ala Ile Pro
530                 535                 540 gca gtc tta cac aac agc acc atg tat gtg ttc ggt ggt ttc aat agt      1680
Ala Val Leu His Asn Ser Thr Met Tyr Val Phe Gly Gly Phe Asn Ser
545                 550                 555                 560 ctc ctc ctc agc gac atc ctg gta ttc acc tcg gaa cag tgt gat gcg      1728
Leu Leu Leu Ser Asp Ile Leu Val Phe Thr Ser Glu Gln Cys Asp Ala
                565                 570                 575 cat cgg agt gaa gcc gct tgt tta gca gca gga cct ggt att cgg tgt      1776
His Arg Ser Glu Ala Ala Cys Leu Ala Ala Gly Pro Gly Ile Arg Cys
            580                 585                 590 gtg tgg aac aca ggg tcg tct cag tgt atc tcg tgg gcg ctg gca act      1824
Val Trp Asn Thr Gly Ser Ser Gln Cys Ile Ser Trp Ala Leu Ala Thr
            595                 600                 605 gat gaa caa gaa gaa aag tta aaa tca gaa tgt ttt tcc aaa aga act      1872
Asp Glu Gln Glu Glu Lys Leu Lys Ser Glu Cys Phe Ser Lys Arg Thr
610                 615                 620
```

-continued

| | | |
|---|---|---|
| ctt gac cat gac aga tgt gac cag cac aca gat tgt tac agc tgc aca<br>Leu Asp His Asp Arg Cys Asp Gln His Thr Asp Cys Tyr Ser Cys Thr<br>625                            630                       635                     640 | 1920 |

```
ctt gac cat gac aga tgt gac cag cac aca gat tgt tac agc tgc aca    1920
Leu Asp His Asp Arg Cys Asp Gln His Thr Asp Cys Tyr Ser Cys Thr
625                 630                 635                 640 gcc aac acc aat gac tgc cac tgg tgc aat gac cat tgt gtc ccc agg    1968
Ala Asn Thr Asn Asp Cys His Trp Cys Asn Asp His Cys Val Pro Arg
                645                 650                 655 aac cac agc tgc tca gaa ggc cag atc tcc att ttt agg tat gag aat    2016
Asn His Ser Cys Ser Glu Gly Gln Ile Ser Ile Phe Arg Tyr Glu Asn
            660                 665                 670 tgc ccc aag gat aac cct atg tac tac tgt aac aag aag acc agc tgc    2064
Cys Pro Lys Asp Asn Pro Met Tyr Tyr Cys Asn Lys Lys Thr Ser Cys
        675                 680                 685 agg agc tgt gcc ctg gac cag aac tgc cag tgg gag ccc cgg aat cag    2112
Arg Ser Cys Ala Leu Asp Gln Asn Cys Gln Trp Glu Pro Arg Asn Gln
690                 695                 700 gag tgc att gcc ctg ccc gaa aat atc tgt ggc att ggc tgg cat ttg    2160
Glu Cys Ile Ala Leu Pro Glu Asn Ile Cys Gly Ile Gly Trp His Leu
705                 710                 715                 720 gtt gga aac tca tgt ttg aaa att act act gcc aag gag aat tat gac    2208
Val Gly Asn Ser Cys Leu Lys Ile Thr Thr Ala Lys Glu Asn Tyr Asp
                725                 730                 735 aat gct aaa ttg ttc tgt agg aac cac aat gcc ctt ttg gct tct ctt    2256
Asn Ala Lys Leu Phe Cys Arg Asn His Asn Ala Leu Leu Ala Ser Leu
            740                 745                 750 aca acc cag aag aag gta gaa ttt gtc ctt aag cag ctg cga ata atg    2304
Thr Thr Gln Lys Lys Val Glu Phe Val Leu Lys Gln Leu Arg Ile Met
        755                 760                 765 cag tca tct cag agc atg tcc aag ctc acc tta acc cca tgg gtc ggc    2352
Gln Ser Ser Gln Ser Met Ser Lys Leu Thr Leu Thr Pro Trp Val Gly
770                 775                 780 ctt cgg aag atc aat gtg tcc tac tgg tgc tgg gaa gat atg tcc cca    2400
Leu Arg Lys Ile Asn Val Ser Tyr Trp Cys Trp Glu Asp Met Ser Pro
785                 790                 795                 800 ttt aca aat agt tta cta cag tgg atg ccg tct gag ccc agt gat gct    2448
Phe Thr Asn Ser Leu Leu Gln Trp Met Pro Ser Glu Pro Ser Asp Ala
                805                 810                 815 gga ttc tgt gga att tta tca gaa ccc agt act cgg gga ctg aag gct    2496
Gly Phe Cys Gly Ile Leu Ser Glu Pro Ser Thr Arg Gly Leu Lys Ala
            820                 825                 830 gca acc tgc atc aac cca ctc aat ggt agt gtc tgt gaa agg cct gca    2544
Ala Thr Cys Ile Asn Pro Leu Asn Gly Ser Val Cys Glu Arg Pro Ala
        835                 840                 845 aac cac agt gct aag cag tgc cgg aca cca tgt gcc ttg agg aca gca    2592
Asn His Ser Ala Lys Gln Cys Arg Thr Pro Cys Ala Leu Arg Thr Ala
850                 855                 860 tgt gga gat tgc acc agc ggc agc tct gag tgc atg tgg tgc agc aac    2640
Cys Gly Asp Cys Thr Ser Gly Ser Ser Glu Cys Met Trp Cys Ser Asn
865                 870                 875                 880 atg aag cag tgt gtg gac tcc aat gcc tat gtg gcc tcc ttc cct ttt    2688
Met Lys Gln Cys Val Asp Ser Asn Ala Tyr Val Ala Ser Phe Pro Phe
                885                 890                 895 ggc cag tgt atg gaa tgg tat acg atg agc acc tgc ccc cct gaa aat    2736
Gly Gln Cys Met Glu Trp Tyr Thr Met Ser Thr Cys Pro Pro Glu Asn
            900                 905                 910 tgt tca ggc tac tgt acc tgt agt cat tgc ttg gag caa cca ggc tgt    2784
Cys Ser Gly Tyr Cys Thr Cys Ser His Cys Leu Glu Gln Pro Gly Cys
        915                 920                 925 ggc tgg tgt act gat ccc agc aat act ggc aaa ggg aaa tgc ata gag    2832
Gly Trp Cys Thr Asp Pro Ser Asn Thr Gly Lys Gly Lys Cys Ile Glu
930                 935                 940
```

```
ggt tcc tat aaa gga cca gtg aag atg cct tcg caa gcc cct aca gga    2880
Gly Ser Tyr Lys Gly Pro Val Lys Met Pro Ser Gln Ala Pro Thr Gly
945                 950                 955                 960 aat ttc tat cca cag ccc ctg ctc aat tcc agc atg tgt cta gag gac    2928
Asn Phe Tyr Pro Gln Pro Leu Leu Asn Ser Ser Met Cys Leu Glu Asp
                965                 970                 975 agc aga tac aac tgg tct ttc att cac tgt cca gct tgc caa tgc aac    2976
Ser Arg Tyr Asn Trp Ser Phe Ile His Cys Pro Ala Cys Gln Cys Asn
            980                 985                 990 ggc cac agt aaa tgc atc aat cag agc atc tgt gag aag tgt gag aac    3024
Gly His Ser Lys Cys Ile Asn Gln Ser Ile Cys Glu Lys Cys Glu Asn
        995                 1000                1005 ctg acc aca ggc aag cac tgc gag acc tgc ata tct ggc ttc tac ggt    3072
Leu Thr Thr Gly Lys His Cys Glu Thr Cys Ile Ser Gly Phe Tyr Gly
    1010                1015                1020 gat ccc acc aat gga ggg aaa tgt cag cca tgc aag tgc aat ggg cac    3120
Asp Pro Thr Asn Gly Gly Lys Cys Gln Pro Cys Lys Cys Asn Gly His
1025                1030                1035                1040 gcg tct ctg tgc aac acc aac acg ggc aag tgc ttc tgc acc acc aag    3168
Ala Ser Leu Cys Asn Thr Asn Thr Gly Lys Cys Phe Cys Thr Thr Lys
                1045                1050                1055 ggc gtc aag ggg gac gag tgc cag cta tgt gag gta gaa aat cga tac    3216
Gly Val Lys Gly Asp Glu Cys Gln Leu Cys Glu Val Glu Asn Arg Tyr
            1060                1065                1070 caa gga aac cct ctc aga gga aca tgt tat tat act ctt ctt att gac    3264
Gln Gly Asn Pro Leu Arg Gly Thr Cys Tyr Tyr Thr Leu Leu Ile Asp
        1075                1080                1085 tat cag ttc acc ttt agt cta tcc cag gaa gat gat cgc tat tac aca    3312
Tyr Gln Phe Thr Phe Ser Leu Ser Gln Glu Asp Asp Arg Tyr Tyr Thr
    1090                1095                1100 gct atc aat ttt gtg gct act cct gac gaa caa aac agg gat ttg gac    3360
Ala Ile Asn Phe Val Ala Thr Pro Asp Glu Gln Asn Arg Asp Leu Asp
1105                1110                1115                1120 atg ttc atc aat gcc tcc aag aat ttc aac ctc aac atc acc tgg gct    3408
Met Phe Ile Asn Ala Ser Lys Asn Phe Asn Leu Asn Ile Thr Trp Ala
                1125                1130                1135 gcc agt ttc tca gct gga acc cag gct gga gaa gag atg cct gtt gtt    3456
Ala Ser Phe Ser Ala Gly Thr Gln Ala Gly Glu Glu Met Pro Val Val
            1140                1145                1150 tca aaa acc aac att aag gag tac aaa gat agt ttc tct aat gag aag    3504
Ser Lys Thr Asn Ile Lys Glu Tyr Lys Asp Ser Phe Ser Asn Glu Lys
        1155                1160                1165 ttt gat ttt cgc aac cac cca aat atc act ttc ttt gtt tat gtc agt    3552
Phe Asp Phe Arg Asn His Pro Asn Ile Thr Phe Phe Val Tyr Val Ser
    1170                1175                1180 aat ttc acc tgg ccc atc aaa att cag gtg caa act gaa caa           3594
Asn Phe Thr Trp Pro Ile Lys Ile Gln Val Gln Thr Glu Gln
1185                1190                1195 tga                                                                3597

<210> SEQ ID NO 2
<211> LENGTH: 1198
<212> TYPE: PRT
<213> ORGANISM: Homo sapiens

<400> SEQUENCE: 2

Met Val Ala Ala Ala Ala Thr Glu Ala Arg Leu Arg Arg Thr
 1               5                  10                  15

Ala Ala Thr Ala Ala Leu Ala Gly Arg Ser Gly Gly Pro His Cys Val
```

-continued

```
                    20                  25                  30
Asn Gly Gly Arg Cys Asn Pro Gly Thr Gly Gln Cys Val Cys Pro Ala
         35                  40                  45
Gly Trp Val Gly Glu Gln Cys Gln His Cys Gly Gly Arg Phe Arg Leu
     50                  55                  60
Thr Gly Ser Ser Gly Phe Val Thr Asp Gly Pro Gly Asn Tyr Lys Tyr
 65                  70                  75                  80
Lys Thr Lys Cys Thr Trp Leu Ile Glu Gly Gln Pro Asn Arg Ile Met
                 85                  90                  95
Arg Leu Arg Phe Asn His Phe Ala Thr Glu Cys Ser Trp Asp His Leu
             100                 105                 110
Tyr Val Tyr Asp Gly Asp Ser Ile Tyr Ala Pro Leu Val Ala Ala Phe
         115                 120                 125
Ser Gly Leu Ile Val Pro Glu Arg Asp Gly Asn Glu Thr Val Pro Glu
     130                 135                 140
Val Val Ala Thr Ser Gly Tyr Ala Leu Leu His Phe Phe Ser Asp Ala
145                 150                 155                 160
Ala Tyr Asn Leu Thr Gly Phe Asn Ile Thr Tyr Ser Phe Asp Met Cys
                165                 170                 175
Pro Asn Asn Cys Ser Gly Arg Gly Glu Cys Lys Ile Ser Asn Ser Ser
            180                 185                 190
Asp Thr Val Glu Cys Glu Cys Ser Glu Asn Trp Lys Gly Glu Ala Cys
        195                 200                 205
Asp Ile Pro His Cys Thr Asp Asn Cys Gly Phe Pro His Arg Gly Ile
    210                 215                 220
Cys Asn Ser Ser Asp Val Arg Gly Cys Ser Cys Phe Ser Asp Trp Gln
225                 230                 235                 240
Gly Pro Gly Cys Ser Val Pro Val Pro Ala Asn Gln Ser Phe Trp Thr
                245                 250                 255
Arg Glu Glu Tyr Ser Asn Leu Lys Leu Pro Arg Ala Ser His Lys Ala
            260                 265                 270
Val Val Asn Gly Asn Ile Met Trp Val Val Gly Gly Tyr Met Phe Asn
        275                 280                 285
His Ser Asp Tyr Asn Met Val Leu Ala Tyr Asp Leu Ala Ser Arg Glu
    290                 295                 300
Trp Leu Pro Leu Asn Arg Ser Val Asn Asn Val Val Arg Tyr Gly
305                 310                 315                 320
His Ser Leu Ala Leu Tyr Lys Asp Lys Ile Tyr Met Tyr Gly Gly Lys
                325                 330                 335
Ile Asp Ser Thr Gly Asn Val Thr Asn Glu Leu Arg Val Phe His Ile
            340                 345                 350
His Asn Glu Ser Trp Val Leu Leu Thr Pro Lys Ala Lys Glu Gln Tyr
        355                 360                 365
Ala Val Val Gly His Ser Ala His Ile Val Thr Leu Lys Asn Gly Arg
    370                 375                 380
Val Val Met Leu Val Ile Phe Gly His Cys Pro Leu Tyr Gly Tyr Ile
385                 390                 395                 400
Ser Asn Val Gln Glu Tyr Asp Leu Asp Lys Asn Thr Trp Ser Ile Leu
                405                 410                 415
His Thr Gln Gly Ala Leu Val Gln Gly Gly Tyr Gly His Ser Ser Val
            420                 425                 430
Tyr Asp His Arg Thr Arg Ala Leu Tyr Val His Gly Gly Tyr Lys Ala
        435                 440                 445
```

-continued

```
Phe Ser Ala Asn Lys Tyr Arg Leu Ala Asp Asp Leu Tyr Arg Tyr Asp
    450                 455                 460

Val Asp Thr Gln Met Trp Thr Ile Leu Lys Asp Ser Arg Phe Phe Arg
465                 470                 475                 480

Tyr Leu His Thr Ala Val Ile Val Ser Gly Thr Met Leu Val Phe Gly
                485                 490                 495

Gly Asn Thr His Asn Asp Thr Ser Met Ser His Gly Ala Lys Cys Phe
                500                 505                 510

Ser Ser Asp Phe Met Ala Tyr Asp Ile Ala Cys Asp Arg Trp Ser Val
        515                 520                 525

Leu Pro Arg Pro Asp Ser Thr Met Met Ser Thr Asp Leu Ala Ile Pro
        530                 535                 540

Ala Val Leu His Asn Ser Thr Met Tyr Val Phe Gly Gly Phe Asn Ser
545                 550                 555                 560

Leu Leu Leu Ser Asp Ile Leu Val Phe Thr Ser Glu Gln Cys Asp Ala
                565                 570                 575

His Arg Ser Glu Ala Ala Cys Leu Ala Ala Gly Pro Gly Ile Arg Cys
                580                 585                 590

Val Trp Asn Thr Gly Ser Ser Gln Cys Ile Ser Trp Ala Leu Ala Thr
        595                 600                 605

Asp Glu Gln Glu Glu Lys Leu Lys Ser Glu Cys Phe Ser Lys Arg Thr
        610                 615                 620

Leu Asp His Asp Arg Cys Asp Gln His Thr Asp Cys Tyr Ser Cys Thr
625                 630                 635                 640

Ala Asn Thr Asn Asp Cys His Trp Cys Asn Asp His Cys Val Pro Arg
                645                 650                 655

Asn His Ser Cys Ser Glu Gly Gln Ile Ser Ile Phe Arg Tyr Glu Asn
                660                 665                 670

Cys Pro Lys Asp Asn Pro Met Tyr Tyr Cys Asn Lys Lys Thr Ser Cys
        675                 680                 685

Arg Ser Cys Ala Leu Asp Gln Asn Cys Gln Trp Glu Pro Arg Asn Gln
690                 695                 700

Glu Cys Ile Ala Leu Pro Glu Asn Ile Cys Gly Ile Gly Trp His Leu
705                 710                 715                 720

Val Gly Asn Ser Cys Leu Lys Ile Thr Thr Ala Lys Glu Asn Tyr Asp
                725                 730                 735

Asn Ala Lys Leu Phe Cys Arg Asn His Asn Ala Leu Leu Ala Ser Leu
                740                 745                 750

Thr Thr Gln Lys Lys Val Glu Phe Val Leu Lys Gln Leu Arg Ile Met
        755                 760                 765

Gln Ser Ser Gln Ser Met Ser Lys Leu Thr Leu Thr Pro Trp Val Gly
        770                 775                 780

Leu Arg Lys Ile Asn Val Ser Tyr Trp Cys Trp Glu Asp Met Ser Pro
785                 790                 795                 800

Phe Thr Asn Ser Leu Leu Gln Trp Met Pro Ser Glu Pro Ser Asp Ala
                805                 810                 815

Gly Phe Cys Gly Ile Leu Ser Glu Pro Ser Thr Arg Gly Leu Lys Ala
                820                 825                 830

Ala Thr Cys Ile Asn Pro Leu Asn Gly Ser Val Cys Glu Arg Pro Ala
        835                 840                 845

Asn His Ser Ala Lys Gln Cys Arg Thr Pro Cys Ala Leu Arg Thr Ala
850                 855                 860
```

-continued

```
Cys Gly Asp Cys Thr Ser Gly Ser Ser Glu Cys Met Trp Cys Ser Asn
865                 870                 875                 880

Met Lys Gln Cys Val Asp Ser Asn Ala Tyr Val Ala Ser Phe Pro Phe
                885                 890                 895

Gly Gln Cys Met Glu Trp Tyr Thr Met Ser Thr Cys Pro Pro Glu Asn
            900                 905                 910

Cys Ser Gly Tyr Cys Thr Cys Ser His Cys Leu Glu Gln Pro Gly Cys
        915                 920                 925

Gly Trp Cys Thr Asp Pro Ser Asn Thr Gly Lys Gly Lys Cys Ile Glu
    930                 935                 940

Gly Ser Tyr Lys Gly Pro Val Lys Met Pro Ser Gln Ala Pro Thr Gly
945                 950                 955                 960

Asn Phe Tyr Pro Gln Pro Leu Leu Asn Ser Ser Met Cys Leu Glu Asp
                965                 970                 975

Ser Arg Tyr Asn Trp Ser Phe Ile His Cys Pro Ala Cys Gln Cys Asn
            980                 985                 990

Gly His Ser Lys Cys Ile Asn Gln Ser Ile Cys Glu Lys Cys Glu Asn
        995                 1000                1005

Leu Thr Thr Gly Lys His Cys Glu Thr Cys Ile Ser Gly Phe Tyr Gly
    1010                1015                1020

Asp Pro Thr Asn Gly Gly Lys Cys Gln Pro Cys Lys Cys Asn Gly His
1025                1030                1035                1040

Ala Ser Leu Cys Asn Thr Asn Thr Gly Lys Cys Phe Cys Thr Thr Lys
                1045                1050                1055

Gly Val Lys Gly Asp Glu Cys Gln Leu Cys Glu Val Glu Asn Arg Tyr
            1060                1065                1070

Gln Gly Asn Pro Leu Arg Gly Thr Cys Tyr Tyr Thr Leu Leu Ile Asp
        1075                1080                1085

Tyr Gln Phe Thr Phe Ser Leu Ser Gln Glu Asp Asp Arg Tyr Tyr Thr
    1090                1095                1100

Ala Ile Asn Phe Val Ala Thr Pro Asp Glu Gln Asn Arg Asp Leu Asp
1105                1110                1115                1120

Met Phe Ile Asn Ala Ser Lys Asn Phe Asn Leu Asn Ile Thr Trp Ala
                1125                1130                1135

Ala Ser Phe Ser Ala Gly Thr Gln Ala Gly Glu Glu Met Pro Val Val
            1140                1145                1150

Ser Lys Thr Asn Ile Lys Glu Tyr Lys Asp Ser Phe Ser Asn Glu Lys
        1155                1160                1165

Phe Asp Phe Arg Asn His Pro Asn Ile Thr Phe Phe Val Tyr Val Ser
    1170                1175                1180

Asn Phe Thr Trp Pro Ile Lys Ile Gln Val Gln Thr Glu Gln
1185                1190                1195
```

<210> SEQ ID NO 3
<211> LENGTH: 34
<212> TYPE: DNA
<213> ORGANISM: Artificial Sequence
<220> FEATURE:
<223> OTHER INFORMATION: oligonucleotide for PCR

<400> SEQUENCE: 3
cccaagcttg ggatgggtgt cgggctcagc ccgc                        34

<210> SEQ ID NO 4
<211> LENGTH: 41
<212> TYPE: DNA

```
<213> ORGANISM: Artificial Sequence
<220> FEATURE:
<223> OTHER INFORMATION: oligonucleotide for PCR

<400> SEQUENCE: 4
ataagaatgc ggcgctaaac tcattgttca gtttcgacct g                    41

<210> SEQ ID NO 5
<211> LENGTH: 32
<212> TYPE: DNA
<213> ORGANISM: Artificial Sequence
<220> FEATURE:
<223> OTHER INFORMATION: oligonucleotide for PCR

<400> SEQUENCE: 5
cccaagcttg ggatggtggc cgcagcggcg gc                              32

<210> SEQ ID NO 6
<211> LENGTH: 25
<212> TYPE: DNA
<213> ORGANISM: Artificial Sequence
<220> FEATURE:
<223> OTHER INFORMATION: oligonucleotide for PCR

<400> SEQUENCE: 6
ccaggtccat ctgtcacaaa cccag                                      25

<210> SEQ ID NO 7
<211> LENGTH: 38
<212> TYPE: DNA
<213> ORGANISM: Artificial Sequence
<220> FEATURE:
<223> OTHER INFORMATION: oligonucleotide for PCR

<400> SEQUENCE: 7
gtgcgtgaag cttgtaccgg caactgaggc aaggctga                        38

<210> SEQ ID NO 8
<211> LENGTH: 39
<212> TYPE: DNA
<213> ORGANISM: Artificial Sequence
<220> FEATURE:
<223> OTHER INFORMATION: oligonucleotide for PCR

<400> SEQUENCE: 8
gtagttttaa gtccacgttt gacttcgccg gcgtgcgtg                       39

<210> SEQ ID NO 9
<211> LENGTH: 15
<212> TYPE: PRT
<213> ORGANISM: Artificial Sequence
<220> FEATURE:
<223> OTHER INFORMATION: synthetically generated polypeptide

<400> SEQUENCE: 9

Gly Ala Pro Val Pro Tyr Pro Asp Pro Leu Glu Pro Arg Ala Ala
 1               5                  10                  15

<210> SEQ ID NO 10
<211> LENGTH: 1355
<212> TYPE: PRT
<213> ORGANISM: Homo sapiens

<400> SEQUENCE: 10

Met Val Ala Ala Ala Ala Ala Thr Glu Ala Arg Leu Arg Arg Arg Thr
 1               5                  10                  15
```

```
Ala Ala Thr Ala Ala Leu Ala Gly Arg Ser Gly Gly Pro His Cys Val
            20                  25                  30

Asn Gly Gly Arg Cys Asn Pro Gly Thr Gly Gln Cys Val Cys Pro Ala
        35                  40                  45

Gly Trp Val Gly Glu Gln Cys Gln His Cys Gly Gly Arg Phe Arg Leu
        50                  55                  60

Thr Gly Ser Ser Gly Phe Val Thr Asp Gly Pro Gly Asn Tyr Lys Tyr
65                  70                  75                  80

Lys Thr Lys Cys Thr Trp Leu Ile Glu Gly Gln Pro Asn Arg Ile Met
                85                  90                  95

Arg Leu Arg Phe Asn His Phe Ala Thr Glu Cys Ser Trp Asp His Leu
            100                 105                 110

Tyr Val Tyr Asp Gly Asp Ser Ile Tyr Ala Pro Leu Val Ala Ala Phe
            115                 120                 125

Ser Gly Leu Ile Val Pro Glu Arg Asp Gly Asn Glu Thr Val Pro Glu
        130                 135                 140

Val Val Ala Thr Ser Gly Tyr Ala Leu Leu His Phe Phe Ser Asp Ala
145                 150                 155                 160

Ala Tyr Asn Leu Thr Gly Phe Asn Ile Thr Tyr Ser Phe Asp Met Cys
                165                 170                 175

Pro Asn Asn Cys Ser Gly Arg Gly Glu Cys Lys Ile Ser Asn Ser Ser
            180                 185                 190

Asp Thr Val Glu Cys Glu Cys Ser Glu Asn Trp Lys Gly Glu Ala Cys
        195                 200                 205

Asp Ile Pro His Cys Thr Asp Asn Cys Gly Phe Pro His Arg Gly Ile
        210                 215                 220

Cys Asn Ser Ser Asp Val Arg Gly Cys Ser Cys Phe Ser Asp Trp Gln
225                 230                 235                 240

Gly Pro Gly Cys Ser Val Pro Val Pro Ala Asn Gln Ser Phe Trp Thr
                245                 250                 255

Arg Glu Glu Tyr Ser Asn Leu Lys Leu Pro Arg Ala Ser His Lys Ala
            260                 265                 270

Val Val Asn Gly Asn Ile Met Trp Val Val Gly Gly Tyr Met Phe Asn
        275                 280                 285

His Ser Asp Tyr Asn Met Val Leu Ala Tyr Asp Leu Ala Ser Arg Glu
        290                 295                 300

Trp Leu Pro Leu Asn Arg Ser Val Asn Val Val Arg Tyr Gly
305                 310                 315                 320

His Ser Leu Ala Leu Tyr Lys Asp Lys Ile Tyr Met Tyr Gly Gly Lys
                325                 330                 335

Ile Asp Ser Thr Gly Asn Val Thr Asn Glu Leu Arg Val Phe His Ile
            340                 345                 350

His Asn Glu Ser Trp Val Leu Leu Thr Pro Lys Ala Lys Glu Gln Tyr
            355                 360                 365

Ala Val Val Gly His Ser Ala His Ile Val Thr Leu Lys Asn Gly Arg
        370                 375                 380

Val Val Met Leu Val Ile Phe Gly His Cys Pro Leu Tyr Gly Tyr Ile
385                 390                 395                 400

Ser Asn Val Gln Glu Tyr Asp Leu Asp Lys Asn Thr Trp Ser Ile Leu
                405                 410                 415

His Thr Gln Gly Ala Leu Val Gln Gly Gly Tyr Gly His Ser Ser Val
            420                 425                 430
```

```
Tyr Asp His Arg Thr Arg Ala Leu Tyr Val His Gly Gly Tyr Lys Ala
        435                 440                 445

Phe Ser Ala Asn Lys Tyr Arg Leu Ala Asp Asp Leu Tyr Arg Tyr Asp
        450                 455                 460

Val Asp Thr Gln Met Trp Thr Ile Leu Lys Asp Ser Arg Phe Phe Arg
465                 470                 475                 480

Tyr Leu His Thr Ala Val Ile Val Ser Gly Thr Met Leu Val Phe Gly
                485                 490                 495

Gly Asn Thr His Asn Asp Thr Ser Met Ser His Gly Ala Lys Cys Phe
                500                 505                 510

Ser Ser Asp Phe Met Ala Tyr Asp Ile Ala Cys Asp Arg Trp Ser Val
        515                 520                 525

Leu Pro Arg Pro Asp Leu His His Asp Val Asn Arg Phe Gly His Ser
        530                 535                 540

Ala Val Leu His Asn Ser Thr Met Tyr Val Phe Gly Gly Phe Asn Ser
545                 550                 555                 560

Leu Leu Leu Ser Asp Ile Leu Val Phe Thr Ser Glu Gln Cys Asp Ala
                565                 570                 575

His Arg Ser Glu Ala Ala Cys Leu Ala Ala Gly Pro Gly Ile Arg Cys
                580                 585                 590

Val Trp Asn Thr Gly Ser Ser Gln Cys Ile Ser Trp Ala Leu Ala Thr
        595                 600                 605

Asp Glu Gln Glu Glu Lys Leu Lys Ser Glu Cys Phe Ser Lys Arg Thr
        610                 615                 620

Leu Asp His Asp Arg Cys Asp Gln His Thr Asp Cys Tyr Ser Cys Thr
625                 630                 635                 640

Ala Asn Thr Asn Asp Cys His Trp Cys Asn Asp His Cys Val Pro Arg
                645                 650                 655

Asn His Ser Cys Ser Glu Gly Gln Ile Ser Ile Phe Arg Tyr Glu Asn
                660                 665                 670

Cys Pro Lys Asp Asn Pro Met Tyr Tyr Cys Asn Lys Lys Thr Ser Cys
        675                 680                 685

Arg Ser Cys Ala Leu Asp Gln Asn Cys Gln Trp Glu Pro Arg Asn Gln
        690                 695                 700

Glu Cys Ile Ala Leu Pro Glu Asn Ile Cys Gly Ile Gly Trp His Leu
705                 710                 715                 720

Val Gly Asn Ser Cys Leu Lys Ile Thr Thr Ala Lys Glu Asn Tyr Asp
                725                 730                 735

Asn Ala Lys Leu Phe Cys Arg Asn His Asn Ala Leu Leu Ala Ser Leu
                740                 745                 750

Thr Thr Gln Lys Lys Val Glu Phe Val Leu Lys Gln Leu Arg Ile Met
        755                 760                 765

Gln Ser Ser Gln Ser Met Ser Lys Leu Thr Leu Thr Pro Trp Val Gly
        770                 775                 780

Leu Arg Lys Ile Asn Val Ser Tyr Trp Cys Trp Glu Asp Met Ser Pro
785                 790                 795                 800

Phe Thr Asn Ser Leu Leu Gln Trp Met Pro Ser Glu Pro Ser Asp Ala
                805                 810                 815

Gly Phe Cys Gly Ile Leu Ser Glu Pro Ser Thr Arg Gly Leu Lys Ala
                820                 825                 830

Ala Thr Cys Ile Asn Pro Leu Asn Gly Ser Val Cys Glu Arg Pro Ala
        835                 840                 845

Asn His Ser Ala Lys Gln Cys Arg Thr Pro Cys Ala Leu Arg Thr Ala
```

-continued

```
            850                 855                 860
Cys Gly Asp Cys Thr Ser Gly Ser Ser Glu Cys Met Trp Cys Ser Asn
865                 870                         875                 880

Met Lys Gln Cys Val Asp Ser Asn Ala Tyr Val Ala Ser Phe Pro Phe
                        885                 890                 895

Gly Gln Cys Met Glu Trp Tyr Thr Met Ser Thr Cys Pro Pro Glu Asn
                900                 905                 910

Cys Ser Gly Tyr Cys Thr Cys Ser His Cys Leu Glu Gln Pro Gly Cys
                915                 920                 925

Gly Trp Cys Thr Asp Pro Ser Asn Thr Gly Lys Gly Lys Cys Ile Glu
930                 935                 940

Gly Ser Tyr Lys Gly Pro Val Lys Met Pro Ser Gln Ala Pro Thr Gly
945                 950                 955                 960

Asn Phe Tyr Pro Gln Pro Leu Leu Asn Ser Ser Met Cys Leu Glu Asp
                965                 970                 975

Ser Arg Tyr Asn Trp Ser Phe Ile His Cys Pro Ala Cys Gln Cys Asn
                980                 985                 990

Gly His Ser Lys Cys Ile Asn Gln Ser Ile Cys Glu Lys Cys Glu Asn
                995                 1000                1005

Leu Thr Thr Gly Lys His Cys Glu Thr Cys Ile Ser Gly Phe Tyr Gly
        1010                1015                1020

Asp Pro Thr Asn Gly Gly Lys Cys Gln Pro Cys Lys Cys Asn Gly His
1025                1030                1035                1040

Ala Ser Leu Cys Asn Thr Asn Thr Gly Lys Cys Phe Cys Thr Thr Lys
                1045                1050                1055

Gly Val Lys Gly Asp Glu Cys Gln Leu Cys Glu Val Glu Asn Arg Tyr
                1060                1065                1070

Gln Gly Asn Pro Leu Arg Gly Thr Cys Tyr Tyr Thr Leu Leu Ile Asp
                1075                1080                1085

Tyr Gln Phe Thr Phe Ser Leu Ser Gln Glu Asp Asp Arg Tyr Tyr Thr
                1090                1095                1100

Ala Ile Asn Phe Val Ala Thr Pro Asp Glu Gln Asn Arg Asp Leu Asp
1105                1110                1115                1120

Met Phe Ile Asn Ala Ser Lys Asn Phe Asn Leu Asn Ile Thr Trp Ala
                1125                1130                1135

Ala Ser Phe Ser Ala Gly Thr Gln Ala Gly Glu Glu Met Pro Val Val
                1140                1145                1150

Ser Lys Thr Asn Ile Lys Glu Tyr Lys Asp Ser Phe Ser Asn Glu Lys
                1155                1160                1165

Phe Asp Phe Arg Asn His Pro Asn Ile Thr Phe Phe Val Tyr Val Ser
        1170                1175                1180

Asn Phe Thr Trp Pro Ile Lys Ile Gln Ile Ala Phe Ser Gln His Ser
1185                1190                1195                1200

Asn Phe Met Asp Leu Val Gln Phe Phe Val Thr Phe Ser Cys Phe
                1205                1210                1215

Leu Ser Leu Leu Leu Val Ala Ala Val Val Trp Lys Ile Lys Gln Ser
        1220                1225                1230

Cys Trp Ala Ser Arg Arg Arg Glu Gln Leu Leu Arg Glu Met Gln Gln
                1235                1240                1245

Met Ala Ser Arg Pro Phe Ala Ser Val Asn Val Ala Leu Glu Thr Asp
        1250                1255                1260

Glu Glu Pro Pro Asp Leu Ile Gly Gly Ser Ile Lys Thr Val Pro Lys
1265                1270                1275                1280
```

```
Pro Ile Ala Leu Glu Pro Cys Phe Gly Asn Lys Ala Ala Val Leu Ser
            1285                1290                1295

Val Phe Val Arg Leu Pro Arg Gly Leu Gly Ile Pro Pro Gly
        1300                1305                1310

Gln Ser Gly Leu Ala Val Ala Ser Ala Leu Val Asp Ile Ser Gln Gln
        1315                1320                1325

Met Pro Ile Val Tyr Lys Glu Lys Ser Gly Ala Val Arg Asn Arg Lys
        1330                1335                1340

Gln Gln Pro Pro Ala Gln Pro Gly Thr Cys Ile
1345                1350                1355

<210> SEQ ID NO 11
<211> LENGTH: 4068
<212> TYPE: DNA
<213> ORGANISM: Homo sapiens
<220> FEATURE:
<221> NAME/KEY: CDS
<222> LOCATION: (1)...(4065)

<400> SEQUENCE: 11 atg gtg gcc gca gcg gcg gca act gag gca agg ctg agg agg agg acg        48
Met Val Ala Ala Ala Ala Ala Thr Glu Ala Arg Leu Arg Arg Arg Thr
  1               5                  10                  15 gcg gcg acg gca gcg ctc gcg ggc agg agc ggc ggg ccg cac tgt gtc        96
Ala Ala Thr Ala Ala Leu Ala Gly Arg Ser Gly Gly Pro His Cys Val
             20                  25                  30 aac ggc ggt cgc tgc aac cct ggc acc ggc cag tgc gtc tgc ccc gcc       144
Asn Gly Gly Arg Cys Asn Pro Gly Thr Gly Gln Cys Val Cys Pro Ala
         35                  40                  45 ggc tgg gtg ggc gag caa tgc cag cac tgc ggg ggc cgc ttc aga cta       192
Gly Trp Val Gly Glu Gln Cys Gln His Cys Gly Gly Arg Phe Arg Leu
     50                  55                  60 act gga tct tct ggg ttt gtg aca gat gga cct gga aat tat aaa tac       240
Thr Gly Ser Ser Gly Phe Val Thr Asp Gly Pro Gly Asn Tyr Lys Tyr
 65                  70                  75                  80 aaa acg aag tgc acg tgg ctc att gaa gga cag cca aat aga ata atg       288
Lys Thr Lys Cys Thr Trp Leu Ile Glu Gly Gln Pro Asn Arg Ile Met
                 85                  90                  95 aga ctt cgt ttc aat cat ttt gct aca gag tgt agt tgg gac cat tta       336
Arg Leu Arg Phe Asn His Phe Ala Thr Glu Cys Ser Trp Asp His Leu
            100                 105                 110 tat gtt tat gat ggg gac tca att tat gca ccg cta gtt gct gca ttt       384
Tyr Val Tyr Asp Gly Asp Ser Ile Tyr Ala Pro Leu Val Ala Ala Phe
        115                 120                 125 agt ggc ctc att gtt cct gag aga gat ggc aat gag act gtc cct gag       432
Ser Gly Leu Ile Val Pro Glu Arg Asp Gly Asn Glu Thr Val Pro Glu
    130                 135                 140 gtt gtt gcc aca tca ggt tat gcc ttg ctg cat ttt ttt agt gat gct       480
Val Val Ala Thr Ser Gly Tyr Ala Leu Leu His Phe Phe Ser Asp Ala
145                 150                 155                 160 gct tat aat ttg act gga ttt aat att act tac agt ttt gat atg tgt       528
Ala Tyr Asn Leu Thr Gly Phe Asn Ile Thr Tyr Ser Phe Asp Met Cys
                165                 170                 175 cca aat aac tgc tca ggc cga gga gag tgt aag atc agt aat agc agc       576
Pro Asn Asn Cys Ser Gly Arg Gly Glu Cys Lys Ile Ser Asn Ser Ser
            180                 185                 190 gat act gtt gaa tgt gaa tgt tct gaa aac tgg aaa ggt gaa gca tgt       624
Asp Thr Val Glu Cys Glu Cys Ser Glu Asn Trp Lys Gly Glu Ala Cys
        195                 200                 205
```

-continued

| | |
|---|---|
| gac att cct cac tgt aca gac aac tgt ggt ttt cct cat cga ggc atc<br>Asp Ile Pro His Cys Thr Asp Asn Cys Gly Phe Pro His Arg Gly Ile<br>210                              215                        220 | 672 |
| tgc aat tca agt gat gtc aga gga tgc tcc tgc ttc tca gac tgg cag<br>Cys Asn Ser Ser Asp Val Arg Gly Cys Ser Cys Phe Ser Asp Trp Gln<br>225                              230                        235                  240 | 720 |
| ggt cct gga tgt tca gtt cct gta cca gct aac cag tca ttt tgg act<br>Gly Pro Gly Cys Ser Val Pro Val Pro Ala Asn Gln Ser Phe Trp Thr<br>                          245                        250                        255 | 768 |
| cga gag gaa tat tct aac tta aag ctc ccc aga gca tct cat aaa gct<br>Arg Glu Glu Tyr Ser Asn Leu Lys Leu Pro Arg Ala Ser His Lys Ala<br>                260                        265                        270 | 816 |
| gtg gtc aat gga aac att atg tgg gtt gtt gga gga tat atg ttc aac<br>Val Val Asn Gly Asn Ile Met Trp Val Val Gly Gly Tyr Met Phe Asn<br>275                              280                        285 | 864 |
| cac tca gat tat aac atg gtt cta gcg tat gac ctt gct tct agg gag<br>His Ser Asp Tyr Asn Met Val Leu Ala Tyr Asp Leu Ala Ser Arg Glu<br>                290                        295                        300 | 912 |
| tgg ctt cca cta aac cgt tct gtg aac aat gtg gtt gtt aga tat ggt<br>Trp Leu Pro Leu Asn Arg Ser Val Asn Asn Val Val Val Arg Tyr Gly<br>305                              310                        315                  320 | 960 |
| cat tct ttg gca tta tac aag gat aaa att tac atg tat gga gga aaa<br>His Ser Leu Ala Leu Tyr Lys Asp Lys Ile Tyr Met Tyr Gly Gly Lys<br>                          325                        330                        335 | 1008 |
| att gat tca act ggg aat gtg acc aat gag ttg aga gtt ttt cac att<br>Ile Asp Ser Thr Gly Asn Val Thr Asn Glu Leu Arg Val Phe His Ile<br>                      340                        345                        350 | 1056 |
| cat aat gag tca tgg gtg ttg ttg acc cct aag gca aag gag cag tat<br>His Asn Glu Ser Trp Val Leu Leu Thr Pro Lys Ala Lys Glu Gln Tyr<br>                          355                        360                        365 | 1104 |
| gca gtg gtt ggg cac tct gca cac att gtt aca ctg aag aat ggc cga<br>Ala Val Val Gly His Ser Ala His Ile Val Thr Leu Lys Asn Gly Arg<br>370                              375                        380 | 1152 |
| gtg gtc atg ctg gtc atc ttt ggt cac tgc cct ctc tat gga tat ata<br>Val Val Met Leu Val Ile Phe Gly His Cys Pro Leu Tyr Gly Tyr Ile<br>385                              390                        395                  400 | 1200 |
| agc aat gtg cag gaa tat gat ttg gat aag aac aca tgg agt ata tta<br>Ser Asn Val Gln Glu Tyr Asp Leu Asp Lys Asn Thr Trp Ser Ile Leu<br>                      405                        410                        415 | 1248 |
| cac acc cag ggt gcc ctt gtg caa ggg ggt tac ggc cat agc agt gtt<br>His Thr Gln Gly Ala Leu Val Gln Gly Gly Tyr Gly His Ser Ser Val<br>                        420                        425                        430 | 1296 |
| tac gac cat agg acc agg gcc cta tac gtt cat ggt ggc tac aag gct<br>Tyr Asp His Arg Thr Arg Ala Leu Tyr Val His Gly Gly Tyr Lys Ala<br>                435                        440                        445 | 1344 |
| ttc agt gcc aat aag tac cgg ctt gca gat gat ctc tac cga tat gat<br>Phe Ser Ala Asn Lys Tyr Arg Leu Ala Asp Asp Leu Tyr Arg Tyr Asp<br>450                              455                        460 | 1392 |
| gtg gat acc cag atg tgg acc att ctt aag gac agc cga ttt ttc cgt<br>Val Asp Thr Gln Met Trp Thr Ile Leu Lys Asp Ser Arg Phe Phe Arg<br>465                              470                        475                  480 | 1440 |
| tac ttg cac aca gct gtg ata gtg agt gga acc atg ctg gtg ttt ggg<br>Tyr Leu His Thr Ala Val Ile Val Ser Gly Thr Met Leu Val Phe Gly<br>                      485                        490                        495 | 1488 |
| gga aac aca cac aat gac aca tct atg agc cat ggc gcc aaa tgc ttc<br>Gly Asn Thr His Asn Asp Thr Ser Met Ser His Gly Ala Lys Cys Phe<br>                        500                        505                        510 | 1536 |
| tct tca gat ttc atg gcc tat gac att gcc tgt gac cgc tgg tca gtg<br>Ser Ser Asp Phe Met Ala Tyr Asp Ile Ala Cys Asp Arg Trp Ser Val<br>               515                        520                        525 | 1584 |

-continued

| | |
|---|---|
| ctt ccc aga cct gat ctc cac cat gat gtc aac aga ttt ggc cat tca<br>Leu Pro Arg Pro Asp Leu His His Asp Val Asn Arg Phe Gly His Ser<br>530                          535                      540 | 1632 |
| gca gtc tta cac aac agc acc atg tat gtg ttc ggt ggt ttc aat agt<br>Ala Val Leu His Asn Ser Thr Met Tyr Val Phe Gly Gly Phe Asn Ser<br>545                          550                      555                      560 | 1680 |
| ctc ctc ctc agc gac atc ctg gta ttc acc tcg gaa cag tgt gat gcg<br>Leu Leu Leu Ser Asp Ile Leu Val Phe Thr Ser Glu Gln Cys Asp Ala<br>                    565                      570                      575 | 1728 |
| cat cgg agt gaa gcc gct tgt tta gca gca gga cct ggt att cgg tgt<br>His Arg Ser Glu Ala Ala Cys Leu Ala Ala Gly Pro Gly Ile Arg Cys<br>        580                      585                      590 | 1776 |
| gtg tgg aac aca ggg tcg tct cag tgt atc tcg tgg gcg ctg gca act<br>Val Trp Asn Thr Gly Ser Ser Gln Cys Ile Ser Trp Ala Leu Ala Thr<br>        595                      600                      605 | 1824 |
| gat gaa caa gaa gaa aag tta aaa tca gaa tgt ttt tcc aaa aga act<br>Asp Glu Gln Glu Glu Lys Leu Lys Ser Glu Cys Phe Ser Lys Arg Thr<br>610                          615                      620 | 1872 |
| ctt gac cat gac aga tgt gac cag cac aca gat tgt tac agc tgc aca<br>Leu Asp His Asp Arg Cys Asp Gln His Thr Asp Cys Tyr Ser Cys Thr<br>625                          630                      635                      640 | 1920 |
| gcc aac acc aat gac tgc cac tgg tgc aat gac cat tgt gtc ccc agg<br>Ala Asn Thr Asn Asp Cys His Trp Cys Asn Asp His Cys Val Pro Arg<br>                    645                      650                      655 | 1968 |
| aac cac agc tgc tca gaa ggc cag atc tcc att ttt agg tat gag aat<br>Asn His Ser Cys Ser Glu Gly Gln Ile Ser Ile Phe Arg Tyr Glu Asn<br>        660                      665                      670 | 2016 |
| tgc ccc aag gat aac cct atg tac tac tgt aac aag aag acc agc tgc<br>Cys Pro Lys Asp Asn Pro Met Tyr Tyr Cys Asn Lys Lys Thr Ser Cys<br>        675                      680                      685 | 2064 |
| agg agc tgt gcc ctg gac cag aac tgc cag tgg gag ccc cgg aat cag<br>Arg Ser Cys Ala Leu Asp Gln Asn Cys Gln Trp Glu Pro Arg Asn Gln<br>690                          695                      700 | 2112 |
| gag tgc att gcc ctg ccc gaa aat atc tgt ggc att ggc tgg cat ttg<br>Glu Cys Ile Ala Leu Pro Glu Asn Ile Cys Gly Ile Gly Trp His Leu<br>705                          710                      715                      720 | 2160 |
| gtt gga aac tca tgt ttg aaa att act act gcc aag gag aat tat gac<br>Val Gly Asn Ser Cys Leu Lys Ile Thr Thr Ala Lys Glu Asn Tyr Asp<br>                    725                      730                      735 | 2208 |
| aat gct aaa ttg ttc tgt agg aac cac aat gcc ctt ttg gct tct ctt<br>Asn Ala Lys Leu Phe Cys Arg Asn His Asn Ala Leu Leu Ala Ser Leu<br>                740                      745                      750 | 2256 |
| aca acc cag aag aag gta gaa ttt gtc ctt aag cag ctg cga ata atg<br>Thr Thr Gln Lys Lys Val Glu Phe Val Leu Lys Gln Leu Arg Ile Met<br>        755                      760                      765 | 2304 |
| cag tca tct cag agc atg tcc aag ctc acc tta acc cca tgg gtc ggc<br>Gln Ser Ser Gln Ser Met Ser Lys Leu Thr Leu Thr Pro Trp Val Gly<br>770                          775                      780 | 2352 |
| ctt cgg aag atc aat gtg tcc tac tgg tgc tgg gaa gat atg tcc cca<br>Leu Arg Lys Ile Asn Val Ser Tyr Trp Cys Trp Glu Asp Met Ser Pro<br>785                          790                      795                      800 | 2400 |
| ttt aca aat agt tta cta cag tgg atg ccg tct gag ccc agt gat gct<br>Phe Thr Asn Ser Leu Leu Gln Trp Met Pro Ser Glu Pro Ser Asp Ala<br>                805                      810                      815 | 2448 |
| gga ttc tgt gga att tta tca gaa ccc agt act cgg gga ctg aag gct<br>Gly Phe Cys Gly Ile Leu Ser Glu Pro Ser Thr Arg Gly Leu Lys Ala<br>        820                      825                      830 | 2496 |
| gca acc tgc atc aac cca ctc aat ggt agt gtc tgt gaa agg cct gca<br>Ala Thr Cys Ile Asn Pro Leu Asn Gly Ser Val Cys Glu Arg Pro Ala | 2544 |

```
                         835                 840                 845
aac cac agt gct aag cag tgc cgg aca cca tgt gcc ttg agg aca gca        2592
Asn His Ser Ala Lys Gln Cys Arg Thr Pro Cys Ala Leu Arg Thr Ala
        850                 855                 860
tgt gga gat tgc acc agc ggc agc tct gag tgc atg tgg tgc agc aac        2640
Cys Gly Asp Cys Thr Ser Gly Ser Ser Glu Cys Met Trp Cys Ser Asn
865                 870                 875                 880
atg aag cag tgt gtg gac tcc aat gcc tat gtg gcc tcc ttc cct ttt        2688
Met Lys Gln Cys Val Asp Ser Asn Ala Tyr Val Ala Ser Phe Pro Phe
                        885                 890                 895
ggc cag tgt atg gaa tgg tat acg atg agc acc tgc ccc cct gaa aat        2736
Gly Gln Cys Met Glu Trp Tyr Thr Met Ser Thr Cys Pro Pro Glu Asn
            900                 905                 910
tgt tca ggc tac tgt acc tgt agt cat tgc ttg gag caa cca ggc tgt        2784
Cys Ser Gly Tyr Cys Thr Cys Ser His Cys Leu Glu Gln Pro Gly Cys
        915                 920                 925
ggc tgg tgt act gat ccc agc aat act ggc aaa ggg aaa tgc ata gag        2832
Gly Trp Cys Thr Asp Pro Ser Asn Thr Gly Lys Gly Lys Cys Ile Glu
930                 935                 940
ggt tcc tat aaa gga cca gtg aag atg cct tcg caa gcc cct aca gga        2880
Gly Ser Tyr Lys Gly Pro Val Lys Met Pro Ser Gln Ala Pro Thr Gly
945                 950                 955                 960
aat ttc tat cca cag ccc ctg ctc aat tcc agc atg tgt cta gag gac        2928
Asn Phe Tyr Pro Gln Pro Leu Leu Asn Ser Ser Met Cys Leu Glu Asp
                965                 970                 975
agc aga tac aac tgg tct ttc att cac tgt cca gct tgc caa tgc aac        2976
Ser Arg Tyr Asn Trp Ser Phe Ile His Cys Pro Ala Cys Gln Cys Asn
            980                 985                 990
ggc cac agt aaa tgc atc aat cag agc atc tgt gag aag tgt gag aac        3024
Gly His Ser Lys Cys Ile Asn Gln Ser Ile Cys Glu Lys Cys Glu Asn
        995                 1000                1005
ctg acc aca ggc aag cac tgc gag acc tgc ata tct ggc ttc tac ggt        3072
Leu Thr Thr Gly Lys His Cys Glu Thr Cys Ile Ser Gly Phe Tyr Gly
        1010                1015                1020
gat ccc acc aat gga ggg aaa tgt cag cca tgc aag tgc aat ggg cac        3120
Asp Pro Thr Asn Gly Gly Lys Cys Gln Pro Cys Lys Cys Asn Gly His
1025                1030                1035                1040
gcg tct ctg tgc aac acc aac acg ggc aag tgc ttc tgc acc acc aag        3168
Ala Ser Leu Cys Asn Thr Asn Thr Gly Lys Cys Phe Cys Thr Thr Lys
            1045                1050                1055
ggc gtc aag ggg gac gag tgc cag cta tgt gag gta gaa aat cga tac        3216
Gly Val Lys Gly Asp Glu Cys Gln Leu Cys Glu Val Glu Asn Arg Tyr
        1060                1065                1070
caa gga aac cct ctc aga gga aca tgt tat tat act ctt ctt att gac        3264
Gln Gly Asn Pro Leu Arg Gly Thr Cys Tyr Tyr Thr Leu Leu Ile Asp
        1075                1080                1085
tat cag ttc acc ttt agt cta tcc cag gaa gat gat cgc tat tac aca        3312
Tyr Gln Phe Thr Phe Ser Leu Ser Gln Glu Asp Asp Arg Tyr Tyr Thr
    1090                1095                1100
gct atc aat ttt gtg gct act cct gac gaa caa aac agg gat ttg gac        3360
Ala Ile Asn Phe Val Ala Thr Pro Asp Glu Gln Asn Arg Asp Leu Asp
1105                1110                1115                1120
atg ttc atc aat gcc tcc aag aat ttc aac ctc aac atc acc tgg gct        3408
Met Phe Ile Asn Ala Ser Lys Asn Phe Asn Leu Asn Ile Thr Trp Ala
            1125                1130                1135
gcc agt ttc tca gct gga acc cag gct gga gaa gag atg cct gtt gtt        3456
Ala Ser Phe Ser Ala Gly Thr Gln Ala Gly Glu Glu Met Pro Val Val
        1140                1145                1150
tca aaa acc aac att aag gag tac aaa gat agt ttc tct aat gag aag        3504
```

```
Ser Lys Thr Asn Ile Lys Glu Tyr Lys Asp Ser Phe Ser Asn Glu Lys
        1155                1160                1165 ttt gat ttt cgc aac cac cca aat atc act ttc ttt gtt tat gtc agt      3552
Phe Asp Phe Arg Asn His Pro Asn Ile Thr Phe Phe Val Tyr Val Ser
    1170                1175                1180 aat ttc acc tgg ccc atc aaa att cag att gcc ttc tct cag cac agc      3600
Asn Phe Thr Trp Pro Ile Lys Ile Gln Ile Ala Phe Ser Gln His Ser
1185                1190                1195                1200 aat ttt atg gac ctg gta cag ttc ttc gtg act ttc ttc agt tgt ttc      3648
Asn Phe Met Asp Leu Val Gln Phe Phe Val Thr Phe Phe Ser Cys Phe
                1205                1210                1215 ctc tct ttg ctc ctg gtg gct gct gtg gtt tgg aag atc aaa caa agt      3696
Leu Ser Leu Leu Leu Val Ala Ala Val Val Trp Lys Ile Lys Gln Ser
            1220                1225                1230 tgt tgg gcc tcc aga cgt aga gag caa ctt ctt cga gag atg caa cag      3744
Cys Trp Ala Ser Arg Arg Arg Glu Gln Leu Leu Arg Glu Met Gln Gln
        1235                1240                1245 atg gcc agc cgt ccc ttt gcc tct gta aat gtc gcc ttg gaa aca gat      3792
Met Ala Ser Arg Pro Phe Ala Ser Val Asn Val Ala Leu Glu Thr Asp
    1250                1255                1260 gag gag cct cct gat ctt att ggg ggg agt ata aag act gtt ccc aaa      3840
Glu Glu Pro Pro Asp Leu Ile Gly Gly Ser Ile Lys Thr Val Pro Lys
1265                1270                1275                1280 ccc att gca ctg gag ccg tgt ttt ggc aac aaa gcc gct gtc ctc tct      3888
Pro Ile Ala Leu Glu Pro Cys Phe Gly Asn Lys Ala Ala Val Leu Ser
                1285                1290                1295 gtg ttt gtg agg ctc cct cga ggc ctg ggt ggc atc cct cct cct ggg      3936
Val Phe Val Arg Leu Pro Arg Gly Leu Gly Gly Ile Pro Pro Pro Gly
            1300                1305                1310 cag tca ggt ctt gct gtg gcc agc gcc ctg gtg gac att tct cag cag      3984
Gln Ser Gly Leu Ala Val Ala Ser Ala Leu Val Asp Ile Ser Gln Gln
        1315                1320                1325 atg ccg ata gtg tac aag gag aag tca gga gcc gtg aga aac cgg aag      4032
Met Pro Ile Val Tyr Lys Glu Lys Ser Gly Ala Val Arg Asn Arg Lys
    1330                1335                1340 cag cag ccc cct gca cag cct ggg acc tgc atc tga                      4068
Gln Gln Pro Pro Ala Gln Pro Gly Thr Cys Ile
1345                1350                1355

<210> SEQ ID NO 12
<211> LENGTH: 1429
<212> TYPE: PRT
<213> ORGANISM: Homo sapiens

<400> SEQUENCE: 12

Met Val Ala Ala Ala Ala Thr Glu Ala Arg Leu Arg Arg Arg Thr
1               5                   10                  15

Ala Ala Thr Ala Ala Leu Ala Gly Arg Ser Gly Gly Pro His Trp Asp
            20                  25                  30

Trp Asp Val Thr Arg Ala Gly Arg Pro Gly Leu Gly Ala Gly Leu Arg
        35                  40                  45

Leu Pro Arg Leu Leu Ser Pro Pro Leu Arg Pro Arg Leu Leu Leu Leu
    50                  55                  60

Leu Leu Leu Leu Pro Pro Pro Leu Leu Leu Leu Leu Pro Cys Glu
65                  70                  75                  80

Ala Glu Ala Ala Ala Ala Ala Ala Val Ser Gly Ser Ala Ala
                85                  90                  95

Glu Ala Lys Glu Cys Asp Arg Pro Cys Val Asn Gly Gly Arg Cys Asn
            100                 105                 110
```

```
Pro Gly Thr Gly Gln Cys Val Cys Pro Ala Gly Trp Val Gly Glu Gln
        115                 120                 125
Cys Gln His Cys Gly Gly Arg Phe Arg Leu Thr Gly Ser Ser Gly Phe
    130                 135                 140
Val Thr Asp Gly Pro Gly Asn Tyr Lys Tyr Lys Thr Lys Cys Thr Trp
145                 150                 155                 160
Leu Ile Glu Gly Gln Pro Asn Arg Ile Met Arg Leu Arg Phe Asn His
                165                 170                 175
Phe Ala Thr Glu Cys Ser Trp Asp His Leu Tyr Val Tyr Asp Gly Asp
            180                 185                 190
Ser Ile Tyr Ala Pro Leu Val Ala Ala Phe Ser Gly Leu Ile Val Pro
        195                 200                 205
Glu Arg Asp Gly Asn Glu Thr Val Pro Glu Val Val Ala Thr Ser Gly
    210                 215                 220
Tyr Ala Leu Leu His Phe Phe Ser Asp Ala Ala Tyr Asn Leu Thr Gly
225                 230                 235                 240
Phe Asn Ile Thr Tyr Ser Phe Asp Met Cys Pro Asn Asn Cys Ser Gly
                245                 250                 255
Arg Gly Glu Cys Lys Ile Ser Asn Ser Ser Glu Thr Val Glu Cys Glu
            260                 265                 270
Cys Ser Glu Asn Trp Lys Gly Glu Ala Cys Asp Ile Pro His Cys Thr
        275                 280                 285
Asp Asn Cys Gly Phe Pro His Arg Gly Ile Cys Asn Ser Ser Asp Val
    290                 295                 300
Arg Gly Cys Ser Cys Phe Ser Asp Trp Gln Gly Pro Gly Cys Ser Val
305                 310                 315                 320
Pro Val Pro Ala Asn Gln Ser Phe Trp Thr Arg Glu Glu Tyr Ser Asn
                325                 330                 335
Leu Lys Leu Pro Arg Ala Ser His Lys Ala Val Val Asn Gly Asn Ile
            340                 345                 350
Met Trp Val Val Gly Gly Tyr Met Phe Asn His Ser Asp Tyr Asn Met
        355                 360                 365
Val Leu Ala Tyr Asp Leu Ala Ser Arg Glu Trp Leu Pro Leu Asn Arg
    370                 375                 380
Ser Val Asn Asn Val Val Arg Tyr Gly His Ser Leu Ala Leu Tyr
385                 390                 395                 400
Lys Asp Lys Ile Tyr Met Tyr Gly Gly Lys Ile Asp Pro Thr Gly Asn
                405                 410                 415
Val Thr Asn Glu Leu Arg Val Phe His Ile His Asn Glu Ser Trp Val
            420                 425                 430
Leu Leu Thr Pro Lys Ala Lys Glu Gln Tyr Ala Val Val Gly His Ser
        435                 440                 445
Ala His Ile Val Thr Leu Lys Asn Gly Arg Val Val Met Leu Val Ile
    450                 455                 460
Phe Gly His Cys Pro Leu Tyr Gly Tyr Ile Ser Asn Val Gln Glu Tyr
465                 470                 475                 480
Asp Leu Asp Lys Asn Thr Trp Ser Ile Leu His Thr Gln Gly Ala Leu
                485                 490                 495
Val Gln Gly Gly Tyr Gly His Ser Ser Val Tyr Asp His Arg Thr Arg
            500                 505                 510
Ala Leu Tyr Val His Gly Gly Tyr Lys Ala Phe Ser Ala Asn Lys Tyr
        515                 520                 525
```

```
Arg Leu Ala Asp Asp Leu Tyr Arg Tyr Asp Val Asp Thr Gln Met Trp
    530                 535                 540

Thr Ile Leu Lys Asp Ser Arg Phe Phe Arg Tyr Leu His Thr Ala Val
545                 550                 555                 560

Ile Val Ser Gly Thr Met Leu Val Phe Gly Gly Asn Thr His Asn Asp
                565                 570                 575

Thr Ser Met Ser His Gly Ala Lys Cys Phe Ser Ser Asp Phe Met Ala
            580                 585                 590

Tyr Asp Ile Ala Cys Asp Arg Trp Ser Val Leu Pro Arg Pro Asp Leu
        595                 600                 605

His His Asp Val Asn Arg Phe Gly His Ser Ala Val Leu His Asn Ser
    610                 615                 620

Thr Met Tyr Val Phe Gly Gly Phe Asn Ser Leu Leu Leu Ser Asp Ile
625                 630                 635                 640

Leu Val Phe Thr Ser Glu Gln Cys Asp Ala His Arg Ser Glu Ala Ala
                645                 650                 655

Cys Leu Ala Ala Gly Pro Gly Ile Arg Cys Val Trp Asn Thr Gly Ser
            660                 665                 670

Ser Gln Cys Ile Ser Trp Ala Leu Ala Thr Asp Glu Gln Glu Glu Lys
        675                 680                 685

Leu Lys Ser Glu Cys Phe Ser Lys Arg Thr Leu Asp His Asp Arg Cys
690                 695                 700

Asp Gln His Thr Asp Cys Tyr Ser Cys Thr Ala Asn Thr Asn Asp Cys
705                 710                 715                 720

His Trp Cys Asn Asp His Cys Val Pro Arg Asn His Ser Cys Ser Glu
                725                 730                 735

Gly Gln Ile Ser Ile Phe Arg Tyr Glu Asn Cys Pro Lys Asp Asn Pro
            740                 745                 750

Met Tyr Tyr Cys Asn Lys Lys Thr Ser Cys Arg Ser Cys Ala Leu Asp
        755                 760                 765

Gln Asn Cys Gln Trp Glu Pro Arg Asn Gln Glu Cys Ile Ala Leu Pro
770                 775                 780

Glu Asn Ile Cys Gly Ile Gly Trp His Leu Val Gly Asn Ser Cys Leu
785                 790                 795                 800

Lys Ile Thr Thr Ala Lys Glu Asn Tyr Asp Asn Ala Lys Leu Phe Cys
                805                 810                 815

Arg Asn His Asn Ala Leu Leu Ala Ser Leu Thr Thr Gln Lys Lys Val
            820                 825                 830

Glu Phe Val Leu Lys Gln Leu Arg Ile Met Gln Ser Ser Gln Ser Met
        835                 840                 845

Ser Lys Leu Thr Leu Thr Pro Trp Val Gly Leu Arg Lys Ile Asn Val
850                 855                 860

Ser Tyr Trp Cys Trp Glu Asp Met Ser Pro Phe Thr Asn Ser Leu Leu
865                 870                 875                 880

Gln Trp Met Pro Ser Glu Pro Ser Asp Ala Gly Phe Cys Gly Ile Leu
                885                 890                 895

Ser Glu Pro Ser Thr Arg Gly Leu Lys Ala Ala Thr Cys Ile Asn Pro
            900                 905                 910

Leu Asn Gly Ser Val Cys Glu Arg Pro Ala Asn His Ser Ala Lys Gln
        915                 920                 925

Cys Arg Thr Pro Cys Ala Leu Arg Thr Ala Cys Gly Asp Cys Thr Ser
930                 935                 940

Gly Ser Ser Glu Cys Met Trp Cys Ser Asn Met Lys Gln Cys Val Asp
```

-continued

```
            945                 950                 955                 960
Ser Asn Ala Tyr Val Ala Ser Phe Pro Phe Gly Gln Cys Met Glu Trp
                    965                 970                 975
Tyr Thr Met Ser Thr Cys Pro Pro Glu Asn Cys Ser Gly Tyr Cys Thr
                980                 985                 990
Cys Ser His Cys Leu Glu Gln Pro Gly Cys Gly Trp Cys Thr Asp Pro
            995                 1000                1005
Ser Asn Thr Gly Lys Gly Lys Cys Ile Glu Gly Ser Tyr Lys Gly Pro
        1010                1015                1020
Val Lys Met Pro Ser Gln Ala Pro Thr Gly Asn Phe Tyr Pro Gln Pro
1025                1030                1035                1040
Leu Leu Asn Ser Ser Met Cys Leu Glu Asp Ser Arg Tyr Asn Trp Ser
                    1045                1050                1055
Phe Ile His Cys Pro Ala Cys Gln Cys Asn Gly His Ser Lys Cys Ile
                1060                1065                1070
Asn Gln Ser Ile Cys Glu Lys Cys Glu Asn Leu Thr Thr Gly Lys His
            1075                1080                1085
Cys Glu Thr Cys Ile Ser Gly Phe Tyr Gly Asp Pro Thr Asn Gly Gly
        1090                1095                1100
Lys Cys Gln Pro Cys Lys Cys Asn Gly His Ala Ser Leu Cys Asn Thr
1105                1110                1115                1120
Asn Thr Gly Lys Cys Phe Cys Thr Thr Lys Gly Val Lys Gly Asp Glu
                    1125                1130                1135
Cys Gln Leu Cys Glu Val Glu Asn Arg Tyr Gln Gly Asn Pro Leu Arg
                1140                1145                1150
Gly Thr Cys Tyr Tyr Thr Leu Leu Ile Asp Tyr Gln Phe Thr Phe Ser
            1155                1160                1165
Leu Ser Gln Glu Asp Asp Arg Tyr Tyr Thr Ala Ile Asn Phe Val Ala
        1170                1175                1180
Thr Pro Asp Glu Gln Asn Arg Asp Leu Asp Met Phe Ile Asn Ala Ser
1185                1190                1195                1200
Lys Asn Phe Asn Leu Asn Ile Thr Trp Ala Ala Ser Phe Ser Ala Gly
                    1205                1210                1215
Thr Gln Ala Gly Glu Glu Met Pro Val Val Ser Lys Thr Asn Ile Lys
                1220                1225                1230
Glu Tyr Lys Asp Ser Phe Ser Asn Glu Lys Phe Asp Phe Arg Asn His
            1235                1240                1245
Pro Asn Ile Thr Phe Phe Val Tyr Val Ser Asn Phe Thr Trp Pro Ile
        1250                1255                1260
Lys Ile Gln Ile Ala Phe Ser Gln His Ser Asn Phe Met Asp Leu Val
1265                1270                1275                1280
Gln Phe Phe Val Thr Phe Phe Ser Cys Phe Leu Ser Leu Leu Leu Val
                    1285                1290                1295
Ala Ala Val Val Trp Lys Ile Lys Gln Ser Cys Trp Ala Ser Arg Arg
                1300                1305                1310
Arg Glu Gln Leu Leu Arg Glu Met Gln Gln Met Ala Ser Arg Pro Phe
            1315                1320                1325
Ala Ser Val Asn Val Ala Leu Glu Thr Asp Glu Glu Pro Pro Asp Leu
        1330                1335                1340
Ile Gly Gly Ser Ile Lys Thr Val Pro Lys Pro Ile Ala Leu Glu Pro
1345                1350                1355                1360
Cys Phe Gly Asn Lys Ala Ala Val Leu Ser Val Phe Val Arg Leu Pro
                    1365                1370                1375
```

-continued

```
Arg Gly Leu Gly Gly Ile Pro Pro Gly Gln Ser Gly Leu Ala Val
        1380                1385                1390

Ala Ser Ala Leu Val Asp Ile Ser Gln Gln Met Pro Ile Val Tyr Lys
        1395                1400                1405

Glu Lys Ser Gly Ala Val Arg Asn Arg Lys Gln Gln Pro Pro Ala Gln
        1410                1415                1420

Pro Gly Thr Cys Ile
1425

<210> SEQ ID NO 13
<211> LENGTH: 4290
<212> TYPE: DNA
<213> ORGANISM: Homo sapiens
<220> FEATURE:
<221> NAME/KEY: CDS
<222> LOCATION: (1)...(4287)

<400> SEQUENCE: 13
```

| | | | | | | | | | | | | | | | | |
|---|---|---|---|---|---|---|---|---|---|---|---|---|---|---|---|---|
| atg | gtg | gcc | gca | gcg | gcg | gca | act | gag | gca | agg | ctg | agg | agg | agg | acg | 48 |
| Met | Val | Ala | Ala | Ala | Ala | Thr | Glu | Ala | Arg | Leu | Arg | Arg | Arg | Thr | | |
| 1 | | | 5 | | | | | 10 | | | | | 15 | | | |
| gcg | gcg | acg | gca | gcg | ctc | gcg | ggc | agg | agc | ggc | ggg | ccg | cac | tgg | gac | 96 |
| Ala | Ala | Thr | Ala | Ala | Leu | Ala | Gly | Arg | Ser | Gly | Gly | Pro | His | Trp | Asp | |
| | | 20 | | | | | 25 | | | | | 30 | | | | |
| tgg | gac | gtg | acc | agg | gct | ggg | agg | ccg | ggg | ctg | ggg | gcc | ggg | ctg | cgc | 144 |
| Trp | Asp | Val | Thr | Arg | Ala | Gly | Arg | Pro | Gly | Leu | Gly | Ala | Gly | Leu | Arg | |
| | 35 | | | | | 40 | | | | | 45 | | | | | |
| ctc | ccg | cgg | ctg | ctg | tct | cca | ccg | ctg | cgg | cca | cgg | ctg | ctg | ctg | ctg | 192 |
| Leu | Pro | Arg | Leu | Leu | Ser | Pro | Pro | Leu | Arg | Pro | Arg | Leu | Leu | Leu | Leu | |
| 50 | | | | | 55 | | | | | 60 | | | | | | |
| ctg | ttg | ttt | ctc | ccg | ccg | ccg | ctg | ttg | ctg | ctg | ctg | ctg | ccc | tgt | gag | 240 |
| Leu | Leu | Leu | Leu | Pro | Pro | Pro | Leu | Leu | Leu | Leu | Leu | Leu | Pro | Cys | Glu | |
| 65 | | | | | 70 | | | | | 75 | | | | | 80 | |
| gcc | gag | gcc | gcg | gcg | gcg | gcg | gcg | gcg | gtg | tcg | ggc | tca | gcc | gca | gcc | 288 |
| Ala | Glu | Ala | Ala | Ala | Ala | Ala | Ala | Ala | Val | Ser | Gly | Ser | Ala | Ala | Ala | |
| | | | 85 | | | | | 90 | | | | | 95 | | | |
| gag | gcc | aag | gaa | tgt | gac | cgg | ccc | tgt | gtc | aac | ggc | ggt | cgc | tgc | aac | 336 |
| Glu | Ala | Lys | Glu | Cys | Asp | Arg | Pro | Cys | Val | Asn | Gly | Gly | Arg | Cys | Asn | |
| | | 100 | | | | | 105 | | | | | 110 | | | | |
| cct | ggc | acc | ggc | cag | tgc | gtc | tgc | ccc | gcc | ggc | tgg | gtg | ggc | gag | caa | 384 |
| Pro | Gly | Thr | Gly | Gln | Cys | Val | Cys | Pro | Ala | Gly | Trp | Val | Gly | Glu | Gln | |
| | 115 | | | | | 120 | | | | | 125 | | | | | |
| tgc | cag | cac | tgc | ggg | ggc | cgc | ttc | aga | cta | act | gga | tct | tct | ggg | ttt | 432 |
| Cys | Gln | His | Cys | Gly | Gly | Arg | Phe | Arg | Leu | Thr | Gly | Ser | Ser | Gly | Phe | |
| 130 | | | | | 135 | | | | | 140 | | | | | | |
| gtg | aca | gat | gga | cct | gga | aat | tat | aaa | tac | aaa | acg | aag | tgc | acg | tgg | 480 |
| Val | Thr | Asp | Gly | Pro | Gly | Asn | Tyr | Lys | Tyr | Lys | Thr | Lys | Cys | Thr | Trp | |
| 145 | | | | | 150 | | | | | 155 | | | | | 160 | |
| ctc | att | gaa | gga | cag | cca | aat | aga | ata | atg | aga | ctt | cgt | ttc | aat | cat | 528 |
| Leu | Ile | Glu | Gly | Gln | Pro | Asn | Arg | Ile | Met | Arg | Leu | Arg | Phe | Asn | His | |
| | | | | 165 | | | | | 170 | | | | | 175 | | |
| ttt | gct | aca | gag | tgt | agt | tgg | gac | cat | tta | tat | gtt | tat | gat | ggg | gac | 576 |
| Phe | Ala | Thr | Glu | Cys | Ser | Trp | Asp | His | Leu | Tyr | Val | Tyr | Asp | Gly | Asp | |
| | | | 180 | | | | | 185 | | | | | 190 | | | |
| tca | att | tat | gca | ccg | cta | gtt | gct | gca | ttt | agt | ggc | ctc | att | gtt | cct | 624 |
| Ser | Ile | Tyr | Ala | Pro | Leu | Val | Ala | Ala | Phe | Ser | Gly | Leu | Ile | Val | Pro | |
| | | 195 | | | | | 200 | | | | | 205 | | | | |
| gag | aga | gat | ggc | aat | gag | act | gtc | cct | gag | gtt | gtt | gcc | aca | tca | ggt | 672 |
| Glu | Arg | Asp | Gly | Asn | Glu | Thr | Val | Pro | Glu | Val | Val | Ala | Thr | Ser | Gly | |
| | 210 | | | | | 215 | | | | | 220 | | | | | |

-continued

| | | |
|---|---|---|
| tat gcc ttg ctg cat ttt ttt agt gat gct gct tat aat ttg act gga<br>Tyr Ala Leu Leu His Phe Phe Ser Asp Ala Ala Tyr Asn Leu Thr Gly<br>225                              230                          235                          240 | 720 |
| ttt aat att act tac agt ttt gat atg tgt cca aat aac tgc tca ggc<br>Phe Asn Ile Thr Tyr Ser Phe Asp Met Cys Pro Asn Asn Cys Ser Gly<br>                          245                          250                          255 | 768 |
| cga gga gag tgt aag atc agt aat agc agc gaa act gtt gaa tgt gaa<br>Arg Gly Glu Cys Lys Ile Ser Asn Ser Ser Glu Thr Val Glu Cys Glu<br>                 260                          265                          270 | 816 |
| tgt tct gaa aac tgg aaa ggt gaa gca tgt gac att cct cac tgt aca<br>Cys Ser Glu Asn Trp Lys Gly Glu Ala Cys Asp Ile Pro His Cys Thr<br>            275                          280                          285 | 864 |
| gac aac tgt ggt ttt cct cat cga ggc atc tgc aat tca agt gat gtc<br>Asp Asn Cys Gly Phe Pro His Arg Gly Ile Cys Asn Ser Ser Asp Val<br>290                              295                          300 | 912 |
| aga gga tgc tcc tgc ttc tca gac tgg cag ggt cct gga tgt tca gtt<br>Arg Gly Cys Ser Cys Phe Ser Asp Trp Gln Gly Pro Gly Cys Ser Val<br>305                              310                          315                          320 | 960 |
| cct gta cca gct aac cag tca ttt tgg act cga gag gaa tat tct aac<br>Pro Val Pro Ala Asn Gln Ser Phe Trp Thr Arg Glu Glu Tyr Ser Asn<br>                          325                          330                          335 | 1008 |
| tta aag ctc ccc aga gca tct cat aaa gct gtg gtc aat gga aac att<br>Leu Lys Leu Pro Arg Ala Ser His Lys Ala Val Val Asn Gly Asn Ile<br>                 340                          345                          350 | 1056 |
| atg tgg gtt gtt gga gga tat atg ttc aac cac tca gat tat aac atg<br>Met Trp Val Val Gly Gly Tyr Met Phe Asn His Ser Asp Tyr Asn Met<br>            355                          360                          365 | 1104 |
| gtt cta gcg tat gac ctt gct tct agg gag tgg ctt cca cta aac cgt<br>Val Leu Ala Tyr Asp Leu Ala Ser Arg Glu Trp Leu Pro Leu Asn Arg<br>370                              375                          380 | 1152 |
| tct gtg aac aat gtg gtt gtt aga tat ggt cat tct ttg gca tta tac<br>Ser Val Asn Asn Val Val Val Arg Tyr Gly His Ser Leu Ala Leu Tyr<br>385                              390                          395                          400 | 1200 |
| aag gat aaa att tac atg tat gga gga aaa att gat cca act ggg aat<br>Lys Asp Lys Ile Tyr Met Tyr Gly Gly Lys Ile Asp Pro Thr Gly Asn<br>                          405                          410                          415 | 1248 |
| gtg acc aat gag ttg aga gtt ttt cac att cat aat gag tca tgg gtg<br>Val Thr Asn Glu Leu Arg Val Phe His Ile His Asn Glu Ser Trp Val<br>            420                          425                          430 | 1296 |
| ttg ttg acc cct aag gca aag gag cag tat gca gtg gtt ggg cac tct<br>Leu Leu Thr Pro Lys Ala Lys Glu Gln Tyr Ala Val Val Gly His Ser<br>                 435                          440                          445 | 1344 |
| gca cac att gtt aca ctg aag aat ggc cga gtg gtc atg ctg gtc atc<br>Ala His Ile Val Thr Leu Lys Asn Gly Arg Val Val Met Leu Val Ile<br>450                              455                          460 | 1392 |
| ttt ggt cac tgc cct ctc tat gga tat ata agc aat gtg cag gaa tat<br>Phe Gly His Cys Pro Leu Tyr Gly Tyr Ile Ser Asn Val Gln Glu Tyr<br>465                              470                          475                          480 | 1440 |
| gat ttg gat aag aac aca tgg agt ata tta cac acc cag ggt gcc ctt<br>Asp Leu Asp Lys Asn Thr Trp Ser Ile Leu His Thr Gln Gly Ala Leu<br>                          485                          490                          495 | 1488 |
| gtg caa ggg ggt tac ggc cat agc agt gtt tac gac cat agg acc agg<br>Val Gln Gly Gly Tyr Gly His Ser Ser Val Tyr Asp His Arg Thr Arg<br>            500                          505                          510 | 1536 |
| gcc cta tac gtt cat ggt ggc tac aag gct ttc agt gcc aat aag tac<br>Ala Leu Tyr Val His Gly Gly Tyr Lys Ala Phe Ser Ala Asn Lys Tyr<br>                 515                          520                          525 | 1584 |
| cgg ctt gca gat gat ctc tac cga tat gat gtg gat acc cag atg tgg<br>Arg Leu Ala Asp Asp Leu Tyr Arg Tyr Asp Val Asp Thr Gln Met Trp | 1632 |

```
                530             535             540
acc att ctt aag gac agc cga ttt ttc cgt tac ttg cac aca gct gtg     1680
Thr Ile Leu Lys Asp Ser Arg Phe Phe Arg Tyr Leu His Thr Ala Val
545                 550                 555                 560 ata gtg agt gga acc atg ctg gtg ttt ggg gga aac aca cac aat gac     1728
Ile Val Ser Gly Thr Met Leu Val Phe Gly Gly Asn Thr His Asn Asp
                565                 570                 575 aca tct atg agc cat ggc gcc aaa tgc ttc tct tca gat ttc atg gcc     1776
Thr Ser Met Ser His Gly Ala Lys Cys Phe Ser Ser Asp Phe Met Ala
            580                 585                 590 tat gac att gcc tgt gac cgc tgg tca gtg ctt ccc aga cct gat ctc     1824
Tyr Asp Ile Ala Cys Asp Arg Trp Ser Val Leu Pro Arg Pro Asp Leu
        595                 600                 605 cac cat gat gtc aac aga ttt ggc cat tca gca gtc tta cac aac agc     1872
His His Asp Val Asn Arg Phe Gly His Ser Ala Val Leu His Asn Ser
    610                 615                 620 acc atg tat gtg ttc ggt ggt ttc aat agt ctc ctc ctc agc gac atc     1920
Thr Met Tyr Val Phe Gly Gly Phe Asn Ser Leu Leu Leu Ser Asp Ile
625                 630                 635                 640 ctg gta ttc acc tcg gaa cag tgt gat gcg cat cgg agt gaa gcc gct     1968
Leu Val Phe Thr Ser Glu Gln Cys Asp Ala His Arg Ser Glu Ala Ala
                645                 650                 655 tgt tta gca gca gga cct ggt att cgg tgt gtg tgg aac aca ggg tcg     2016
Cys Leu Ala Ala Gly Pro Gly Ile Arg Cys Val Trp Asn Thr Gly Ser
            660                 665                 670 tct cag tgt atc tcg tgg gcg ctg gca act gat gaa caa gaa gaa aag     2064
Ser Gln Cys Ile Ser Trp Ala Leu Ala Thr Asp Glu Gln Glu Glu Lys
        675                 680                 685 tta aaa tca gaa tgt ttt tcc aaa aga act ctt gac cat gac aga tgt     2112
Leu Lys Ser Glu Cys Phe Ser Lys Arg Thr Leu Asp His Asp Arg Cys
    690                 695                 700 gac cag cac aca gat tgt tac agc tgt aca gcc aac acc aat gac tgc     2160
Asp Gln His Thr Asp Cys Tyr Ser Cys Thr Ala Asn Thr Asn Asp Cys
705                 710                 715                 720 cac tgg tgc aat gac cat tgt gtc ccc agg aac cac agc tgc tca gaa     2208
His Trp Cys Asn Asp His Cys Val Pro Arg Asn His Ser Cys Ser Glu
                725                 730                 735 ggc cag atc tcc att ttt agg tat gag aat tgc ccc aag gat aac ccc     2256
Gly Gln Ile Ser Ile Phe Arg Tyr Glu Asn Cys Pro Lys Asp Asn Pro
            740                 745                 750 atg tac tac tgt aac aag aag acc agc tgc agg agc tgt gcc ctg gac     2304
Met Tyr Tyr Cys Asn Lys Lys Thr Ser Cys Arg Ser Cys Ala Leu Asp
        755                 760                 765 cag aac tgc cag tgg gag ccc cgg aat cag gag tgc att gcc ctg ccc     2352
Gln Asn Cys Gln Trp Glu Pro Arg Asn Gln Glu Cys Ile Ala Leu Pro
    770                 775                 780 gaa aat atc tgt ggc att ggc tgg cat ttg gtt gga aac tca tgt ttg     2400
Glu Asn Ile Cys Gly Ile Gly Trp His Leu Val Gly Asn Ser Cys Leu
785                 790                 795                 800 aaa att act act gcc aag gag aat tat gac aat gct aaa ttg ttc tgt     2448
Lys Ile Thr Thr Ala Lys Glu Asn Tyr Asp Asn Ala Lys Leu Phe Cys
                805                 810                 815 agg aac cac aat gcc ctt ttg gct tct ctt aca acc cag aag aag gta     2496
Arg Asn His Asn Ala Leu Leu Ala Ser Leu Thr Thr Gln Lys Lys Val
            820                 825                 830 gaa ttt gtc ctt aag cag ctg cga ata atg cag tca tct cag agc atg     2544
Glu Phe Val Leu Lys Gln Leu Arg Ile Met Gln Ser Ser Gln Ser Met
        835                 840                 845 tcc aag ctc acc tta acc cca tgg gtc ggc ctt cgg aag atc aat gtg     2592
```

-continued

```
Ser Lys Leu Thr Leu Thr Pro Trp Val Gly Leu Arg Lys Ile Asn Val
    850                 855                 860 tcc tac tgg tgc tgg gaa gat atg tcc cca ttt aca aat agt tta cta      2640
Ser Tyr Trp Cys Trp Glu Asp Met Ser Pro Phe Thr Asn Ser Leu Leu
865                 870                 875                 880 cag tgg atg ccg tct gag ccc agt gat gct gga ttc tgt gga att tta      2688
Gln Trp Met Pro Ser Glu Pro Ser Asp Ala Gly Phe Cys Gly Ile Leu
                885                 890                 895 tca gaa ccc agt act cgg gga ctg aag gct gca acc tgc atc aac cca      2736
Ser Glu Pro Ser Thr Arg Gly Leu Lys Ala Ala Thr Cys Ile Asn Pro
        900                 905                 910 ctc aat ggt agt gtc tgt gaa agg cct gca aac cac agt gct aag cag      2784
Leu Asn Gly Ser Val Cys Glu Arg Pro Ala Asn His Ser Ala Lys Gln
    915                 920                 925 tgc cgg aca cca tgt gcc ttg agg aca gca tgt gga gat tgc acc agc      2832
Cys Arg Thr Pro Cys Ala Leu Arg Thr Ala Cys Gly Asp Cys Thr Ser
930                 935                 940 ggc agc tct gag tgc atg tgg tgc agc aac atg aag cag tgt gtg gac      2880
Gly Ser Ser Glu Cys Met Trp Cys Ser Asn Met Lys Gln Cys Val Asp
945                 950                 955                 960 tcc aat gcc tat gtg gcc tcc ttc cct ttt ggc cag tgt atg gaa tgg      2928
Ser Asn Ala Tyr Val Ala Ser Phe Pro Phe Gly Gln Cys Met Glu Trp
                965                 970                 975 tat acg atg agc acc tgc ccc cct gaa aat tgt tca ggc tac tgt acc      2976
Tyr Thr Met Ser Thr Cys Pro Pro Glu Asn Cys Ser Gly Tyr Cys Thr
        980                 985                 990 tgt agt cat tgc ttg gag caa cca ggc tgt ggc tgg tgt act gat ccc      3024
Cys Ser His Cys Leu Glu Gln Pro Gly Cys Gly Trp Cys Thr Asp Pro
    995                 1000                1005 agc aat act ggc aaa ggg aaa tgc ata gag ggt tcc tat aaa gga cca      3072
Ser Asn Thr Gly Lys Gly Lys Cys Ile Glu Gly Ser Tyr Lys Gly Pro
1010                1015                1020 gtg aag atg cct tcg caa gcc cct aca gga aat ttc tat cca cag ccc      3120
Val Lys Met Pro Ser Gln Ala Pro Thr Gly Asn Phe Tyr Pro Gln Pro
1025                1030                1035                1040 ctg ctc aat tcc agc atg tgt cta gag gac agc aga tac aac tgg tct      3168
Leu Leu Asn Ser Ser Met Cys Leu Glu Asp Ser Arg Tyr Asn Trp Ser
                1045                1050                1055 ttc att cac tgt cca gct tgc caa tgc aac ggc cac agt aaa tgc atc      3216
Phe Ile His Cys Pro Ala Cys Gln Cys Asn Gly His Ser Lys Cys Ile
        1060                1065                1070 aat cag agc atc tgt gag aag tgt gag aac ctg acc aca ggc aag cac      3264
Asn Gln Ser Ile Cys Glu Lys Cys Glu Asn Leu Thr Thr Gly Lys His
    1075                1080                1085 tgc gag acc tgc ata tct ggc ttc tac ggt gat ccc acc aat gga ggg      3312
Cys Glu Thr Cys Ile Ser Gly Phe Tyr Gly Asp Pro Thr Asn Gly Gly
1090                1095                1100 aaa tgt cag cca tgc aag tgc aat ggg cac gcg tct ctg tgc aac acc      3360
Lys Cys Gln Pro Cys Lys Cys Asn Gly His Ala Ser Leu Cys Asn Thr
1105                1110                1115                1120 aac acg ggc aag tgc ttc tgc acc acc aag ggc gtc aag ggg gac gag      3408
Asn Thr Gly Lys Cys Phe Cys Thr Thr Lys Gly Val Lys Gly Asp Glu
                1125                1130                1135 tgc cag cta tgt gag gta gaa aat cga tac caa gga aac cct ctc aga      3456
Cys Gln Leu Cys Glu Val Glu Asn Arg Tyr Gln Gly Asn Pro Leu Arg
        1140                1145                1150 gga aca tgt tat tat act ctt ctt att gac tat cag ttc acc ttt agt      3504
Gly Thr Cys Tyr Tyr Thr Leu Leu Ile Asp Tyr Gln Phe Thr Phe Ser
    1155                1160                1165
```

```
                                                              -continued cta tcc cag gaa gat gat cgc tat tac aca gct atc aat ttt gtg gct     3552
Leu Ser Gln Glu Asp Asp Arg Tyr Tyr Thr Ala Ile Asn Phe Val Ala
        1170                1175                1180 act cct gac gaa caa aac agg gat ttg gac atg ttc atc aat gcc tcc     3600
Thr Pro Asp Glu Gln Asn Arg Asp Leu Asp Met Phe Ile Asn Ala Ser
1185                1190                1195                1200 aag aat ttc aac ctc aac atc acc tgg gct gcc agt ttc tca gct gga     3648
Lys Asn Phe Asn Leu Asn Ile Thr Trp Ala Ala Ser Phe Ser Ala Gly
                1205                1210                1215 acc cag gct gga gaa gag atg cct gtt gtt tca aaa acc aac att aag     3696
Thr Gln Ala Gly Glu Glu Met Pro Val Val Ser Lys Thr Asn Ile Lys
        1220                1225                1230 gag tac aaa gat agt ttc tct aat gag aag ttt gat ttt cgc aac cac     3744
Glu Tyr Lys Asp Ser Phe Ser Asn Glu Lys Phe Asp Phe Arg Asn His
        1235                1240                1245 cca aat atc act ttc ttt gtt tat gtc agt aat ttc acc tgg ccc atc     3792
Pro Asn Ile Thr Phe Phe Val Tyr Val Ser Asn Phe Thr Trp Pro Ile
    1250                1255                1260 aaa att cag att gcc ttc tct cag cac agc aat ttt atg gac ctg gta     3840
Lys Ile Gln Ile Ala Phe Ser Gln His Ser Asn Phe Met Asp Leu Val
1265                1270                1275                1280 cag ttc ttc gtg act ttc ttc agt tgt ttc ctc tct ttg ctc ctg gtg     3888
Gln Phe Phe Val Thr Phe Phe Ser Cys Phe Leu Ser Leu Leu Leu Val
                1285                1290                1295 gct gct gtg gtt tgg aag atc aaa caa agt tgt tgg gcc tcc aga cgt     3936
Ala Ala Val Val Trp Lys Ile Lys Gln Ser Cys Trp Ala Ser Arg Arg
        1300                1305                1310 aga gag caa ctt ctt cga gag atg caa cag atg gcc agc cgt ccc ttt     3984
Arg Glu Gln Leu Leu Arg Glu Met Gln Gln Met Ala Ser Arg Pro Phe
        1315                1320                1325 gcc tct gta aat gtc gcc ttg gaa aca gat gag gag cct cct gat ctt     4032
Ala Ser Val Asn Val Ala Leu Glu Thr Asp Glu Glu Pro Pro Asp Leu
    1330                1335                1340 att ggg ggg agt ata aag act gtt ccc aaa ccc att gca ctg gag ccg     4080
Ile Gly Gly Ser Ile Lys Thr Val Pro Lys Pro Ile Ala Leu Glu Pro
1345                1350                1355                1360 tgt ttt ggc aac aaa gcc gct gtc ctc tct gtg ttt gtg agg ctc cct     4128
Cys Phe Gly Asn Lys Ala Ala Val Leu Ser Val Phe Val Arg Leu Pro
                1365                1370                1375 cga ggc ctg ggt ggc atc cct cct cct ggg cag tca ggt ctt gct gtg     4176
Arg Gly Leu Gly Gly Ile Pro Pro Pro Gly Gln Ser Gly Leu Ala Val
        1380                1385                1390 gcc agc gcc ctg gtg gac att tct cag cag atg ccg ata gtg tac aag     4224
Ala Ser Ala Leu Val Asp Ile Ser Gln Gln Met Pro Ile Val Tyr Lys
        1395                1400                1405 gag aag tca gga gcc gtg aga aac cgg aag cag cag ccc cct gca cag     4272
Glu Lys Ser Gly Ala Val Arg Asn Arg Lys Gln Gln Pro Pro Ala Gln
    1410                1415                1420 cct ggg acc tgc atc tga                                             4290
Pro Gly Thr Cys Ile
1425

<210> SEQ ID NO 14
<211> LENGTH: 25
<212> TYPE: PRT
<213> ORGANISM: Homo sapiens

<400> SEQUENCE: 14

Met Ala Ile Ser Gly Val Pro Val Leu Gly Phe Phe Ile Ile Ala Val
  1               5                  10                  15
```

```
Leu Met Ser Ala Gln Glu Ser Trp Ala
            20              25

<210> SEQ ID NO 15
<211> LENGTH: 5
<212> TYPE: PRT
<213> ORGANISM: Bos taurus

<400> SEQUENCE: 15

Lys Phe Glu Arg Gln
 1               5

<210> SEQ ID NO 16
<211> LENGTH: 15
<212> TYPE: PRT
<213> ORGANISM: Homo sapiens

<400> SEQUENCE: 16

Met Asp Asp Gln Arg Asp Leu Ile Ser Asn Asn Glu Gln Leu Pro
 1               5                  10                  15

<210> SEQ ID NO 17
<211> LENGTH: 4
<212> TYPE: PRT
<213> ORGANISM: Rattus norvegicus

<400> SEQUENCE: 17

Lys Asp Glu Leu
 1

<210> SEQ ID NO 18
<211> LENGTH: 1272
<212> TYPE: PRT
<213> ORGANISM: Homo sapiens

<400> SEQUENCE: 18

Met Val Ala Ala Ala Ala Thr Glu Ala Arg Leu Arg Arg Arg Thr
 1               5                  10                  15

Ala Ala Thr Ala Ala Leu Ala Gly Arg Ser Gly Gly Pro His Trp Asp
            20                  25                  30

Trp Asp Val Thr Arg Ala Gly Arg Pro Gly Leu Gly Ala Gly Leu Arg
            35                  40                  45

Leu Pro Arg Leu Leu Ser Pro Pro Leu Arg Pro Arg Leu Leu Leu Leu
    50                  55                  60

Leu Leu Leu Leu Pro Pro Pro Leu Leu Leu Leu Leu Pro Cys Glu
 65                  70                  75                  80

Ala Glu Ala Ala Ala Ala Ala Ala Val Ser Gly Ser Ala Ala Ala
                85                  90                  95

Glu Ala Lys Glu Cys Asp Arg Pro Cys Val Asn Gly Gly Arg Cys Asn
                100                 105                 110

Pro Gly Thr Gly Gln Cys Val Cys Pro Ala Gly Trp Val Gly Glu Gln
            115                 120                 125

Cys Gln His Cys Gly Gly Arg Phe Arg Leu Thr Gly Ser Ser Gly Phe
130                 135                 140

Val Thr Asp Gly Pro Gly Asn Tyr Lys Tyr Lys Thr Lys Cys Thr Trp
145                 150                 155                 160

Leu Ile Glu Gly Gln Pro Asn Arg Ile Met Arg Leu Arg Phe Asn His
                165                 170                 175

Phe Ala Thr Glu Cys Ser Trp Asp His Leu Tyr Val Tyr Asp Gly Asp
                180                 185                 190
```

```
Ser Ile Tyr Ala Pro Leu Val Ala Phe Ser Gly Leu Ile Val Pro
        195                 200                 205

Glu Arg Asp Gly Asn Glu Thr Val Pro Glu Val Val Ala Thr Ser Gly
210                 215                 220

Tyr Ala Leu Leu His Phe Phe Ser Asp Ala Ala Tyr Asn Leu Thr Gly
225                 230                 235                 240

Phe Asn Ile Thr Tyr Ser Phe Asp Met Cys Pro Asn Asn Cys Ser Gly
                245                 250                 255

Arg Gly Glu Cys Lys Ile Ser Asn Ser Ser Glu Thr Val Glu Cys Glu
                260                 265                 270

Cys Ser Glu Asn Trp Lys Gly Glu Ala Cys Asp Ile Pro His Cys Thr
        275                 280                 285

Asp Asn Cys Gly Phe Pro His Arg Gly Ile Cys Asn Ser Ser Asp Val
        290                 295                 300

Arg Gly Cys Ser Cys Phe Ser Asp Trp Gln Gly Pro Gly Cys Ser Val
305                 310                 315                 320

Pro Val Pro Ala Asn Gln Ser Phe Trp Thr Arg Glu Glu Tyr Ser Asn
                325                 330                 335

Leu Lys Leu Pro Arg Ala Ser His Lys Ala Val Val Asn Gly Asn Ile
                340                 345                 350

Met Trp Val Val Gly Gly Tyr Met Phe Asn His Ser Asp Tyr Asn Met
        355                 360                 365

Val Leu Ala Tyr Asp Leu Ala Ser Arg Glu Trp Leu Pro Leu Asn Arg
        370                 375                 380

Ser Val Asn Asn Val Val Val Arg Tyr Gly His Ser Leu Ala Leu Tyr
385                 390                 395                 400

Lys Asp Lys Ile Tyr Met Tyr Gly Gly Lys Ile Asp Pro Thr Gly Asn
                405                 410                 415

Val Thr Asn Glu Leu Arg Val Phe His Ile His Asn Glu Ser Trp Val
                420                 425                 430

Leu Leu Thr Pro Lys Ala Lys Glu Gln Tyr Ala Val Val Gly His Ser
        435                 440                 445

Ala His Ile Val Thr Leu Lys Asn Gly Arg Val Val Met Leu Val Ile
        450                 455                 460

Phe Gly His Cys Pro Leu Tyr Gly Tyr Ile Ser Asn Val Gln Glu Tyr
465                 470                 475                 480

Asp Leu Asp Lys Asn Thr Trp Ser Ile Leu His Thr Gln Gly Ala Leu
                485                 490                 495

Val Gln Gly Gly Tyr Gly His Ser Ser Val Tyr Asp His Arg Thr Arg
                500                 505                 510

Ala Leu Tyr Val His Gly Gly Tyr Lys Ala Phe Ser Ala Asn Lys Tyr
        515                 520                 525

Arg Leu Ala Asp Asp Leu Tyr Arg Tyr Asp Val Asp Thr Gln Met Trp
        530                 535                 540

Thr Ile Leu Lys Asp Ser Arg Phe Phe Arg Tyr Leu His Thr Ala Val
545                 550                 555                 560

Ile Val Ser Gly Thr Met Leu Val Phe Gly Gly Asn Thr His Asn Asp
                565                 570                 575

Thr Ser Met Ser His Gly Ala Lys Cys Phe Ser Ser Asp Phe Met Ala
                580                 585                 590

Tyr Asp Ile Ala Cys Asp Arg Trp Ser Val Leu Pro Arg Pro Asp Leu
        595                 600                 605
```

-continued

His His Asp Val Asn Arg Phe Gly His Ser Ala Val Leu His Asn Ser
    610                 615                 620

Thr Met Tyr Val Phe Gly Gly Phe Asn Ser Leu Leu Leu Ser Asp Ile
625                 630                 635                 640

Leu Val Phe Thr Ser Glu Gln Cys Asp Ala His Arg Ser Glu Ala Ala
                645                 650                 655

Cys Leu Ala Ala Gly Pro Gly Ile Arg Cys Val Trp Asn Thr Gly Ser
                660                 665                 670

Ser Gln Cys Ile Ser Trp Ala Leu Ala Thr Asp Glu Gln Glu Glu Lys
                675                 680                 685

Leu Lys Ser Glu Cys Phe Ser Lys Arg Thr Leu Asp His Asp Arg Cys
    690                 695                 700

Asp Gln His Thr Asp Cys Tyr Ser Cys Thr Ala Asn Thr Asn Asp Cys
705                 710                 715                 720

His Trp Cys Asn Asp His Cys Val Pro Arg Asn His Ser Cys Ser Glu
                725                 730                 735

Gly Gln Ile Ser Ile Phe Arg Tyr Glu Asn Cys Pro Lys Asp Asn Pro
                740                 745                 750

Met Tyr Tyr Cys Asn Lys Lys Thr Ser Cys Arg Ser Cys Ala Leu Asp
                755                 760                 765

Gln Asn Cys Gln Trp Glu Pro Arg Asn Gln Glu Cys Ile Ala Leu Pro
770                 775                 780

Glu Asn Ile Cys Gly Ile Gly Trp His Leu Val Gly Asn Ser Cys Leu
785                 790                 795                 800

Lys Ile Thr Thr Ala Lys Glu Asn Tyr Asp Asn Ala Lys Leu Phe Cys
                805                 810                 815

Arg Asn His Asn Ala Leu Leu Ala Ser Leu Thr Thr Gln Lys Lys Val
                820                 825                 830

Glu Phe Val Leu Lys Gln Leu Arg Ile Met Gln Ser Ser Gln Ser Met
                835                 840                 845

Ser Lys Leu Thr Leu Thr Pro Trp Val Gly Leu Arg Lys Ile Asn Val
850                 855                 860

Ser Tyr Trp Cys Trp Glu Asp Met Ser Pro Phe Thr Asn Ser Leu Leu
865                 870                 875                 880

Gln Trp Met Pro Ser Glu Pro Ser Asp Ala Gly Phe Cys Gly Ile Leu
                885                 890                 895

Ser Glu Pro Ser Thr Arg Gly Leu Lys Ala Ala Thr Cys Ile Asn Pro
                900                 905                 910

Leu Asn Gly Ser Val Cys Glu Arg Pro Ala Asn His Ser Ala Lys Gln
                915                 920                 925

Cys Arg Thr Pro Cys Ala Leu Arg Thr Ala Cys Gly Asp Cys Thr Ser
    930                 935                 940

Gly Ser Ser Glu Cys Met Trp Cys Ser Asn Met Lys Gln Cys Val Asp
945                 950                 955                 960

Ser Asn Ala Tyr Val Ala Ser Phe Pro Phe Gly Gln Cys Met Glu Trp
                965                 970                 975

Tyr Thr Met Ser Thr Cys Pro Pro Glu Asn Cys Ser Gly Tyr Cys Thr
                980                 985                 990

Cys Ser His Cys Leu Glu Gln Pro Gly Cys Gly Trp Cys Thr Asp Pro
                995                 1000                1005

Ser Asn Thr Gly Lys Gly Lys Cys Ile Glu Gly Ser Tyr Lys Gly Pro
    1010                1015                1020

Val Lys Met Pro Ser Gln Ala Pro Thr Gly Asn Phe Tyr Pro Gln Pro

```
                1025            1030            1035            1040
Leu Leu Asn Ser Ser Met Cys Leu Glu Asp Ser Arg Tyr Asn Trp Ser
                    1045            1050            1055
Phe Ile His Cys Pro Ala Cys Gln Cys Asn Gly His Ser Lys Cys Ile
                1060            1065            1070
Asn Gln Ser Ile Cys Glu Lys Cys Glu Asn Leu Thr Thr Gly Lys His
            1075            1080            1085
Cys Glu Thr Cys Ile Ser Gly Phe Tyr Gly Asp Pro Thr Asn Gly Gly
        1090            1095            1100
Lys Cys Gln Pro Cys Lys Cys Asn Gly His Ala Ser Leu Cys Asn Thr
1105            1110            1115            1120
Asn Thr Gly Lys Cys Phe Cys Thr Thr Lys Gly Val Lys Gly Asp Glu
                1125            1130            1135
Cys Gln Leu Cys Glu Val Glu Asn Arg Tyr Gln Gly Asn Pro Leu Arg
            1140            1145            1150
Gly Thr Cys Tyr Tyr Thr Leu Leu Ile Asp Tyr Gln Phe Thr Phe Ser
        1155            1160            1165
Leu Ser Gln Glu Asp Asp Arg Tyr Tyr Thr Ala Ile Asn Phe Val Ala
    1170            1175            1180
Thr Pro Asp Glu Gln Asn Arg Asp Leu Asp Met Phe Ile Asn Ala Ser
1185            1190            1195            1200
Lys Asn Phe Asn Leu Asn Ile Thr Trp Ala Ala Ser Phe Ser Ala Gly
                1205            1210            1215
Thr Gln Ala Gly Glu Glu Met Pro Val Val Ser Lys Thr Asn Ile Lys
            1220            1225            1230
Glu Tyr Lys Asp Ser Phe Ser Asn Glu Lys Phe Asp Phe Arg Asn His
        1235            1240            1245
Pro Asn Ile Thr Phe Phe Val Tyr Val Ser Asn Phe Thr Trp Pro Ile
    1250            1255            1260
Lys Ile Gln Val Gln Thr Glu Gln
1265            1270

<210> SEQ ID NO 19
<211> LENGTH: 3819
<212> TYPE: DNA
<213> ORGANISM: Homo sapiens
<220> FEATURE:
<221> NAME/KEY: CDS
<222> LOCATION: (1)...(3816)

<400> SEQUENCE: 19 atg gtg gcc gca gcg gcg gca act gag gca agg ctg agg agg agg acg       48
Met Val Ala Ala Ala Ala Thr Glu Ala Arg Leu Arg Arg Arg Thr
1               5                   10                  15 gcg gcg acg gca gcg ctc gcg ggc agg agc ggc ggg ccg cac tgg gac       96
Ala Ala Thr Ala Ala Leu Ala Gly Arg Ser Gly Gly Pro His Trp Asp
                20                  25                  30 tgg gac gtg acc agg gct ggg agg ccg ggg ctg ggg gcc ggg ctg cgc      144
Trp Asp Val Thr Arg Ala Gly Arg Pro Gly Leu Gly Ala Gly Leu Arg
            35                  40                  45 ctc ccg cgg ctg ctg tct cca ccg ctg cgg cca cgg ctg ctg ctg ctg      192
Leu Pro Arg Leu Leu Ser Pro Pro Leu Arg Pro Arg Leu Leu Leu Leu
        50                  55                  60 ctg ttg ttg ctc ccg ccg ccg ctg ttg ctg ctg ctg ccc tgt gag          240
Leu Leu Leu Leu Pro Pro Pro Leu Leu Leu Leu Leu Pro Cys Glu
65                  70                  75                  80 gcc gag gcc gcg gcg gcg gcg gcg gcg gtg tcg ggc tca gcc gca gcc      288
```

```
                Ala Glu Ala Ala Ala Ala Ala Ala Val Ser Gly Ser Ala Ala Ala
                            85                  90                  95 gag gcc aag gaa tgt gac cgg ccc tgt gtc aac ggc ggt cgc tgc aac          336
Glu Ala Lys Glu Cys Asp Arg Pro Cys Val Asn Gly Gly Arg Cys Asn
                100                 105                 110 cct ggc acc ggc cag tgc gtc tgc ccc gcc ggc tgg gtg ggc gag caa          384
Pro Gly Thr Gly Gln Cys Val Cys Pro Ala Gly Trp Val Gly Glu Gln
            115                 120                 125 tgc cag cac tgc ggg ggc cgc ttc aga cta act gga tct tct ggg ttt          432
Cys Gln His Cys Gly Gly Arg Phe Arg Leu Thr Gly Ser Ser Gly Phe
        130                 135                 140 gtg aca gat gga cct gga aat tat aaa tac aaa acg aag tgc acg tgg          480
Val Thr Asp Gly Pro Gly Asn Tyr Lys Tyr Lys Thr Lys Cys Thr Trp
145                 150                 155                 160 ctc att gaa gga cag cca aat aga ata atg aga ctt cgt ttc aat cat          528
Leu Ile Glu Gly Gln Pro Asn Arg Ile Met Arg Leu Arg Phe Asn His
                165                 170                 175 ttt gct aca gag tgt agt tgg gac cat tta tat gtt tat gat ggg gac          576
Phe Ala Thr Glu Cys Ser Trp Asp His Leu Tyr Val Tyr Asp Gly Asp
                180                 185                 190 tca att tat gca ccg cta gtt gct gca ttt agt ggc ctc att gtt cct          624
Ser Ile Tyr Ala Pro Leu Val Ala Ala Phe Ser Gly Leu Ile Val Pro
            195                 200                 205 gag aga gat ggc aat gag act gtc cct gag gtt gtt gcc aca tca ggt          672
Glu Arg Asp Gly Asn Glu Thr Val Pro Glu Val Val Ala Thr Ser Gly
210                 215                 220 tat gcc ttg ctg cat ttt ttt agt gat gct gct tat aat ttg act gga          720
Tyr Ala Leu Leu His Phe Phe Ser Asp Ala Ala Tyr Asn Leu Thr Gly
225                 230                 235                 240 ttt aat att act tac agt ttt gat atg tgt cca aat aac tgc tca ggc          768
Phe Asn Ile Thr Tyr Ser Phe Asp Met Cys Pro Asn Asn Cys Ser Gly
                245                 250                 255 cga gga gag tgt aag atc agt aat agc agc gaa act gtt gaa tgt gaa          816
Arg Gly Glu Cys Lys Ile Ser Asn Ser Ser Glu Thr Val Glu Cys Glu
            260                 265                 270 tgt tct gaa aac tgg aaa ggt gaa gca tgt gac att cct cac tgt aca          864
Cys Ser Glu Asn Trp Lys Gly Glu Ala Cys Asp Ile Pro His Cys Thr
        275                 280                 285 gac aac tgt ggt ttt cct cat cga ggc atc tgc aat tca agt gat gtc          912
Asp Asn Cys Gly Phe Pro His Arg Gly Ile Cys Asn Ser Ser Asp Val
        290                 295                 300 aga gga tgc tcc tgc ttc tca gac tgg cag ggt cct gga tgt tca gtt          960
Arg Gly Cys Ser Cys Phe Ser Asp Trp Gln Gly Pro Gly Cys Ser Val
305                 310                 315                 320 cct gta cca gct aac cag tca ttt tgg act cga gag gaa tat tct aac         1008
Pro Val Pro Ala Asn Gln Ser Phe Trp Thr Arg Glu Glu Tyr Ser Asn
                325                 330                 335 tta aag ctc ccc aga gca tct cat aaa gct gtg gtc aat gga aac att         1056
Leu Lys Leu Pro Arg Ala Ser His Lys Ala Val Val Asn Gly Asn Ile
                340                 345                 350 atg tgg gtt gtt gga gga tat atg ttc aac cac tca gat tat aac atg         1104
Met Trp Val Val Gly Gly Tyr Met Phe Asn His Ser Asp Tyr Asn Met
            355                 360                 365 gtt cta gcg tat gac ctt gct tct agg gag tgg ctt cca cta aac cgt         1152
Val Leu Ala Tyr Asp Leu Ala Ser Arg Glu Trp Leu Pro Leu Asn Arg
        370                 375                 380 tct gtg aac aat gtg gtt gtt aga tat ggt cat tct ttg gca tta tac         1200
Ser Val Asn Asn Val Val Val Arg Tyr Gly His Ser Leu Ala Leu Tyr
385                 390                 395                 400
```

```
aag gat aaa att tac atg tat gga gga aaa att gat cca act ggg aat       1248
Lys Asp Lys Ile Tyr Met Tyr Gly Gly Lys Ile Asp Pro Thr Gly Asn
                405                 410                 415 gtg acc aat gag ttg aga gtt ttt cac att cat aat gag tca tgg gtg       1296
Val Thr Asn Glu Leu Arg Val Phe His Ile His Asn Glu Ser Trp Val
            420                 425                 430 ttg ttg acc cct aag gca aag gag cag tat gca gtg gtt ggg cac tct       1344
Leu Leu Thr Pro Lys Ala Lys Glu Gln Tyr Ala Val Val Gly His Ser
        435                 440                 445 gca cac att gtt aca ctg aag aat ggc cga gtg gtc atg ctg gtc atc       1392
Ala His Ile Val Thr Leu Lys Asn Gly Arg Val Val Met Leu Val Ile
    450                 455                 460 ttt ggt cac tgc cct ctc tat gga tat ata agc aat gtg cag gaa tat       1440
Phe Gly His Cys Pro Leu Tyr Gly Tyr Ile Ser Asn Val Gln Glu Tyr
465                 470                 475                 480 gat ttg gat aag aac aca tgg agt ata tta cac acc cag ggt gcc ctt       1488
Asp Leu Asp Lys Asn Thr Trp Ser Ile Leu His Thr Gln Gly Ala Leu
                485                 490                 495 gtg caa ggg ggt tac ggc cat agc agt gtt tac gac cat agg acc agg       1536
Val Gln Gly Gly Tyr Gly His Ser Ser Val Tyr Asp His Arg Thr Arg
            500                 505                 510 gcc cta tac gtt cat ggt ggc tac aag gct ttc agt gcc aat aag tac       1584
Ala Leu Tyr Val His Gly Gly Tyr Lys Ala Phe Ser Ala Asn Lys Tyr
        515                 520                 525 cgg ctt gca gat gat ctc tac cga tat gat gtg gat acc cag atg tgg       1632
Arg Leu Ala Asp Asp Leu Tyr Arg Tyr Asp Val Asp Thr Gln Met Trp
    530                 535                 540 acc att ctt aag gac agc cga ttt ttc cgt tac ttg cac aca gct gtg       1680
Thr Ile Leu Lys Asp Ser Arg Phe Phe Arg Tyr Leu His Thr Ala Val
545                 550                 555                 560 ata gtg agt gga acc atg ctg gtg ttt ggg gga aac aca cac aat gac       1728
Ile Val Ser Gly Thr Met Leu Val Phe Gly Gly Asn Thr His Asn Asp
                565                 570                 575 aca tct atg agc cat ggc gcc aaa tgc ttc tct tca gat ttc atg gcc       1776
Thr Ser Met Ser His Gly Ala Lys Cys Phe Ser Ser Asp Phe Met Ala
            580                 585                 590 tat gac att gcc tgt gac cgc tgg tca gtg ctt ccc aga cct gat ctc       1824
Tyr Asp Ile Ala Cys Asp Arg Trp Ser Val Leu Pro Arg Pro Asp Leu
        595                 600                 605 cac cat gat gtc aac aga ttt ggc cat tca gca gtc tta cac aac agc       1872
His His Asp Val Asn Arg Phe Gly His Ser Ala Val Leu His Asn Ser
    610                 615                 620 acc atg tat gtg ttc ggt ggt ttc aat agt ctc ctc ctc agc gac atc       1920
Thr Met Tyr Val Phe Gly Gly Phe Asn Ser Leu Leu Leu Ser Asp Ile
625                 630                 635                 640 ctg gta ttc acc tcg gaa cag tgt gat gcg cat cgg agt gaa gcc gct       1968
Leu Val Phe Thr Ser Glu Gln Cys Asp Ala His Arg Ser Glu Ala Ala
                645                 650                 655 tgt tta gca gca gga cct ggt att cgg tgt gtg tgg aac aca ggg tcg       2016
Cys Leu Ala Ala Gly Pro Gly Ile Arg Cys Val Trp Asn Thr Gly Ser
            660                 665                 670 tct cag tgt atc tcg tgg gcg ctg gca act gat gaa caa gaa gaa aag       2064
Ser Gln Cys Ile Ser Trp Ala Leu Ala Thr Asp Glu Gln Glu Glu Lys
        675                 680                 685 tta aaa tca gaa tgt ttt tcc aaa aga act ctt gac cat gac aga tgt       2112
Leu Lys Ser Glu Cys Phe Ser Lys Arg Thr Leu Asp His Asp Arg Cys
    690                 695                 700 gac cag cac aca gat tgt tac agc tgt aca gcc aac acc aat gac tgc       2160
Asp Gln His Thr Asp Cys Tyr Ser Cys Thr Ala Asn Thr Asn Asp Cys
705                 710                 715                 720
```

-continued

| | |
|---|---|
| cac tgg tgc aat gac cat tgt gtc ccc agg aac cac agc tgc tca gaa<br>His Trp Cys Asn Asp His Cys Val Pro Arg Asn His Ser Cys Ser Glu<br>                        725                              730                           735 | 2208 |
| ggc cag atc tcc att ttt agg tat gag aat tgc ccc aag gat aac ccc<br>Gly Gln Ile Ser Ile Phe Arg Tyr Glu Asn Cys Pro Lys Asp Asn Pro<br>                        740                              745                           750 | 2256 |
| atg tac tac tgt aac aag aag acc agc tgc agg agc tgt gcc ctg gac<br>Met Tyr Tyr Cys Asn Lys Lys Thr Ser Cys Arg Ser Cys Ala Leu Asp<br>                        755                              760                           765 | 2304 |
| cag aac tgc cag tgg gag ccc cgg aat cag gag tgc att gcc ctg ccc<br>Gln Asn Cys Gln Trp Glu Pro Arg Asn Gln Glu Cys Ile Ala Leu Pro<br>770                              775                              780 | 2352 |
| gaa aat atc tgt ggc att ggc tgg cat ttg gtt gga aac tca tgt ttg<br>Glu Asn Ile Cys Gly Ile Gly Trp His Leu Val Gly Asn Ser Cys Leu<br>785                              790                              795                           800 | 2400 |
| aaa att act act gcc aag gag aat tat gac aat gct aaa ttg ttc tgt<br>Lys Ile Thr Thr Ala Lys Glu Asn Tyr Asp Asn Ala Lys Leu Phe Cys<br>                        805                              810                           815 | 2448 |
| agg aac cac aat gcc ctt ttg gct tct ctt aca acc cag aag aag gta<br>Arg Asn His Asn Ala Leu Leu Ala Ser Leu Thr Thr Gln Lys Lys Val<br>                        820                              825                           830 | 2496 |
| gaa ttt gtc ctt aag cag ctg cga ata atg cag tca tct cag agc atg<br>Glu Phe Val Leu Lys Gln Leu Arg Ile Met Gln Ser Ser Gln Ser Met<br>                        835                              840                           845 | 2544 |
| tcc aag ctc acc tta acc cca tgg gtc ggc ctt cgg aag atc aat gtg<br>Ser Lys Leu Thr Leu Thr Pro Trp Val Gly Leu Arg Lys Ile Asn Val<br>850                              855                              860 | 2592 |
| tcc tac tgg tgc tgg gaa gat atg tcc cca ttt aca aat agt tta cta<br>Ser Tyr Trp Cys Trp Glu Asp Met Ser Pro Phe Thr Asn Ser Leu Leu<br>865                              870                              875                           880 | 2640 |
| cag tgg atg ccg tct gag ccc agt gat gct gga ttc tgt gga att tta<br>Gln Trp Met Pro Ser Glu Pro Ser Asp Ala Gly Phe Cys Gly Ile Leu<br>                        885                              890                           895 | 2688 |
| tca gaa ccc agt act cgg gga ctg aag gct gca acc tgc atc aac cca<br>Ser Glu Pro Ser Thr Arg Gly Leu Lys Ala Ala Thr Cys Ile Asn Pro<br>                        900                              905                           910 | 2736 |
| ctc aat ggt agt gtc tgt gaa agg cct gca aac cac agt gct aag cag<br>Leu Asn Gly Ser Val Cys Glu Arg Pro Ala Asn His Ser Ala Lys Gln<br>                        915                              920                           925 | 2784 |
| tgc cgg aca cca tgt gcc ttg agg aca gca tgt gga gat tgc acc agc<br>Cys Arg Thr Pro Cys Ala Leu Arg Thr Ala Cys Gly Asp Cys Thr Ser<br>930                              935                              940 | 2832 |
| ggc agc tct gag tgc atg tgg tgc agc aac atg aag cag tgt gtg gac<br>Gly Ser Ser Glu Cys Met Trp Cys Ser Asn Met Lys Gln Cys Val Asp<br>945                              950                              955                           960 | 2880 |
| tcc aat gcc tat gtg gcc tcc ttc cct ttt ggc cag tgt atg gaa tgg<br>Ser Asn Ala Tyr Val Ala Ser Phe Pro Phe Gly Gln Cys Met Glu Trp<br>                        965                              970                           975 | 2928 |
| tat acg atg agc acc tgc ccc cct gaa aat tgt tca ggc tac tgt acc<br>Tyr Thr Met Ser Thr Cys Pro Pro Glu Asn Cys Ser Gly Tyr Cys Thr<br>                        980                              985                           990 | 2976 |
| tgt agt cat tgc ttg gag caa cca ggc tgt ggc tgg tgt act gat ccc<br>Cys Ser His Cys Leu Glu Gln Pro Gly Cys Gly Trp Cys Thr Asp Pro<br>                        995                              1000                         1005 | 3024 |
| agc aat act ggc aaa ggg aaa tgc ata gag ggt tcc tat aaa gga cca<br>Ser Asn Thr Gly Lys Gly Lys Cys Ile Glu Gly Ser Tyr Lys Gly Pro<br>                        1010                           1015                         1020 | 3072 |
| gtg aag atg cct tcg caa gcc cct aca gga aat ttc tat cca cag ccc<br>Val Lys Met Pro Ser Gln Ala Pro Thr Gly Asn Phe Tyr Pro Gln Pro | 3120 |

-continued

```
         1025                1030                1035                1040
ctg ctc aat tcc agc atg tgt cta gag gac agc aga tac aac tgg tct     3168
Leu Leu Asn Ser Ser Met Cys Leu Glu Asp Ser Arg Tyr Asn Trp Ser
                1045                1050                1055 ttc att cac tgt cca gct tgc caa tgc aac ggc cac agt aaa tgc atc     3216
Phe Ile His Cys Pro Ala Cys Gln Cys Asn Gly His Ser Lys Cys Ile
            1060                1065                1070 aat cag agc atc tgt gag aag tgt gag aac ctg acc aca ggc aag cac     3264
Asn Gln Ser Ile Cys Glu Lys Cys Glu Asn Leu Thr Thr Gly Lys His
        1075                1080                1085 tgc gag acc tgc ata tct ggc ttc tac ggt gat ccc acc aat gga ggg     3312
Cys Glu Thr Cys Ile Ser Gly Phe Tyr Gly Asp Pro Thr Asn Gly Gly
    1090                1095                1100 aaa tgt cag cca tgc aag tgc aat ggg cac gcg tct ctg tgc aac acc     3360
Lys Cys Gln Pro Cys Lys Cys Asn Gly His Ala Ser Leu Cys Asn Thr
1105                1110                1115                1120 aac acg ggc aag tgc ttc tgc acc acc aag ggc gtc aag ggg gac gag     3408
Asn Thr Gly Lys Cys Phe Cys Thr Thr Lys Gly Val Lys Gly Asp Glu
                1125                1130                1135 tgc cag cta tgt gag gta gaa aat cga tac caa gga aac cct ctc aga     3456
Cys Gln Leu Cys Glu Val Glu Asn Arg Tyr Gln Gly Asn Pro Leu Arg
            1140                1145                1150 gga aca tgt tat tat act ctt ctt att gac tat cag ttc acc ttt agt     3504
Gly Thr Cys Tyr Tyr Thr Leu Leu Ile Asp Tyr Gln Phe Thr Phe Ser
        1155                1160                1165 cta tcc cag gaa gat gat cgc tat tac aca gct atc aat ttt gtg gct     3552
Leu Ser Gln Glu Asp Asp Arg Tyr Tyr Thr Ala Ile Asn Phe Val Ala
    1170                1175                1180 act cct gac gaa caa aac agg gat ttg gac atg ttc atc aat gcc tcc     3600
Thr Pro Asp Glu Gln Asn Arg Asp Leu Asp Met Phe Ile Asn Ala Ser
1185                1190                1195                1200 aag aat ttc aac ctc aac atc acc tgg gct gcc agt ttc tca gct gga     3648
Lys Asn Phe Asn Leu Asn Ile Thr Trp Ala Ala Ser Phe Ser Ala Gly
                1205                1210                1215 acc cag gct gga gaa gag atg cct gtt gtt tca aaa acc aac att aag     3696
Thr Gln Ala Gly Glu Glu Met Pro Val Val Ser Lys Thr Asn Ile Lys
            1220                1225                1230 gag tac aaa gat agt ttc tct aat gag aag ttt gat ttt cgc aac cac     3744
Glu Tyr Lys Asp Ser Phe Ser Asn Glu Lys Phe Asp Phe Arg Asn His
        1235                1240                1245 cca aat atc act ttc ttt gtt tat gtc agt aat ttc acc tgg ccc atc     3792
Pro Asn Ile Thr Phe Phe Val Tyr Val Ser Asn Phe Thr Trp Pro Ile
    1250                1255                1260 aaa att cag gtg caa act gaa caa tga                                 3819
Lys Ile Gln Val Gln Thr Glu Gln
1265                1270
```

<210> SEQ ID NO 20
<211> LENGTH: 17
<212> TYPE: PRT
<213> ORGANISM: Homo sapiens

<400> SEQUENCE: 20

Cys Glu Val Glu Asn Arg Tyr Gln Gly Asn Pro Leu Arg Gly Thr Cys
 1               5                   10                  15

Tyr

<210> SEQ ID NO 21
<211> LENGTH: 12
<212> TYPE: PRT

<213> ORGANISM: Homo sapiens

<400> SEQUENCE: 21

Ala Ala Leu Ala Gly Arg Ser Gly Gly Pro His Cys
 1               5                  10

<210> SEQ ID NO 22
<211> LENGTH: 5
<212> TYPE: PRT
<213> ORGANISM: Homo sapiens
<220> FEATURE:
<221> NAME/KEY: VARIANT
<222> LOCATION: (1)...(4)
<223> OTHER INFORMATION: Xaa = Any Amino Acid
<221> NAME/KEY: VARIANT
<222> LOCATION: (5)...(5)
<223> OTHER INFORMATION: Xaa = Gly, Ser, or Ala

<400> SEQUENCE: 22

Gly Xaa Ser Xaa Xaa
 1               5

<210> SEQ ID NO 23
<211> LENGTH: 30
<212> TYPE: PRT
<213> ORGANISM: Homo sapiens
<220> FEATURE:
<221> NAME/KEY: VARIANT
<222> LOCATION: (2)...(8)
<223> OTHER INFORMATION: Xaa = Any Amino Acid
<221> NAME/KEY: VARIANT
<222> LOCATION: (9)...(9)
<223> OTHER INFORMATION: Xaa = Leu, Ile, Val, Met, Phe, Tyr, or Trp
<221> NAME/KEY: VARIANT
<222> LOCATION: (10)...(29)
<223> OTHER INFORMATION: Xaa = Any Amino Acid
<221> NAME/KEY: VARIANT
<222> LOCATION: (30)...(30)
<223> OTHER INFORMATION: Xaa = Leu, Ile, Val, Met, Phe, Tyr, or Trp

<400> SEQUENCE: 23

Asp Xaa Xaa Xaa Ala Xaa Xaa Xaa Xaa Xaa Xaa Xaa Xaa Xaa Xaa
 1               5                  10                  15

Xaa Xaa Xaa Xaa Xaa Xaa Xaa Gly Xaa Ser Xaa Gly Gly Xaa
             20                  25                  30

<210> SEQ ID NO 24
<211> LENGTH: 11
<212> TYPE: PRT
<213> ORGANISM: Homo sapiens
<220> FEATURE:
<221> NAME/KEY: VARIANT
<222> LOCATION: (3)...(4)
<223> OTHER INFORMATION: Xaa = Any Amino Acid
<221> NAME/KEY: VARIANT
<222> LOCATION: (6)...(6)
<223> OTHER INFORMATION: Xaa = Asp or Glu
<221> NAME/KEY: VARIANT
<222> LOCATION: (9)...(9)
<223> OTHER INFORMATION: Xaa = Gly or Ser

<400> SEQUENCE: 24

Ala Ala Xaa Xaa Gly Xaa Ser Gly Xaa Pro His
 1               5                  10

<210> SEQ ID NO 25
<211> LENGTH: 10

-continued

```
<212> TYPE: DNA
<213> ORGANISM: Homo sapiens

<400> SEQUENCE: 25
gggaagatgg                                                              10
```

REGULATION OF IMMUNE RESPONSES BY ATTRACTIN

This application claims the benefit of Provisional application Ser. No. 60/100,137 filed Sep. 14, 1998.

BACKGROUND OF THE INVENTION

The present invention relates to agents that regulate immune responses.

Analysis of in vitro immune responses allows basic interactions between cells and soluble modulators to be studied, but interpretations may be difficult to extend to actual responses in vivo, where reactions occur in complex cellular environments with constant dynamic modification of the extracellular environment. An important role is played by the extracellular matrix which interacts with adhesion structures on the surface of immune cells, directing cell migration, localization and clustering and subsequently influences the activity of local cytokines and lymphokines [Shimizu et al. (1991) *FASEB J.* 5, 2292–2299; Gilat et al. (1996) *Immunol. Today* 17, 16–20]. The passage of activated leukocytes between endothelial cells and their migration through the extracellular matrix to sites of inflammation is facilitated by the upregulated surface expression of several adhesion molecules and proteases [Hauzenberger et al. (1995) *Crit. Rev. Immunol.* 15, 285–316].

On activated T cells, one of the most prominently expressed proteases is CD26, which is a marker of T lymphocytes capable of migrating across endothelial barriers [Masuyama et al. (1992) *J. Immunol.* 148, 1367–1374; Brezinschek et al. (1995) *J. Immunol.* 154, 3062–3077] and has a collagen-binding domain [Loster et al. (1995) *Biochem. Biosphys. Res. Commun.* 217, 341–348]. CD26 is now known to be identical to both dipeptidyl peptidase IV (DPPIV) and adenosine deaminase binding protein [Kameoka et al. (1993) *Science* 261, 466–469]. The understanding of the multifunctionality of CD26, which is the prototype for a family of related molecules which includes Fibroblast Activation Protein [Scanlan et al. (1994) *Proc. Natl. Acad. Sci. USA* 91, 5657–5661], DPPIV [Wada et al. (1992) *Proc. Natl, Acad. Sci. USA* 89, 197–201] and Seprase [Goldstein et al. (1997) *Biochim. Biophys. Acta* 1361, 11–19; Pineiro-Sanchez et al. (1997) *J. Biol. Chem.* 272, 7595–7601], has expanded to include T lymphocyte costimulatory activity, where it enhances immune responses channeled through the CD3/T cell receptor complex [Dang et al. (1990) J. Immunol. 144, 4092–4100].

A soluble serum form of DPPIV had previously been identified [Tanaka et al. (1994) *Proc. Natl. Acad. Sci. USA* 91, 3082–3086], and its circulating levels were determined to be related to the ability of peripheral blood mononuclear cells (PBMC) to react in vitro to recall antigens such as tetanus toxoid. Based on this activity, it was conjectured that the identified soluble serum protein was a soluble form of CD26. However, upon purification of the protein, its glycosylated form was found to have a molecular weight of 175 kDa, and therefore, it was distinct from the 105 kDa glycosylated form of DPPIV/CD26 [Duke-Cohan et al. (1995) *J. Biol. Chem.* 270, 14107–14114]. The soluble serum protein having DPPIV activity was designated DPPT-L. DPPT-L appeared to be related to CD26 in that it displayed some CD26 antigenic epitopes, it was rapidly expressed as a T lymphocyte activation antigen, after 48–72 hr it was released from the lymphocyte membrane, and it could upregulate recall antigen-specific T cell responses in a manner similar to that of CD26 [Duke-Cohan et al. (1996) *J. Immunol.* 156, 1714–1721].

SUMMARY OF THE INVENTION

The invention features four isolated forms of the human attractin polypeptide. These are soluble attractin-1 (previously named DPPT-L in the mistaken belief that it was related to, and even a soluble form of, DPPIV/CD26), membrane attractin-1, soluble attractin-2, and membrane attractin-2. Text that refers to attractin without specifying soluble versus membrane or attractin-1 versus attractin-2 is pertinent to all forms of attractin. Membrane attractin differs from soluble attractin in that it has a transmembrane domain and a cytoplasmic domain. Attractin-2 differs from attractin-1 in that it contains a 74-amino acid insert in the N-terminal part of the polypeptide. The attractin molecules serve to enhance immune response by promoting macrophage and monocyte spreading an the presence of T cells. The invention also includes nucleic acid molecules encoding attractin polypeptides, vectors containing the nucleic acid molecules, and cells transformed with the vectors. In addition, the invention includes methods of enhancing or inhibiting immune responses and methods of identifying compounds that enhance or inhibit immune responses.

Specifically, the invention features an isolated DNA including: (a) a nucleic acid sequence that encodes a polypeptide that enhances spreading of a macrophage or a monocyte and that hybridizes under stringent conditions to the complement of a sequence that encodes a polypeptide with an amino aced sequence selected from the group consisting of SEQ ID NO:2, SEQ ID NO:10, SEQ ID NO:12, and SEQ ID NO:18; or (b) a complement of this nucleic acid sequence. The nucleic acid sequence included in the isolated DNA will be at least 10 bp, 15 bp, 25 bp, 50 bp, 75 bp, 100 bp, 125 bp, 150 bp, 175 bp, 200 bp, 250 bp, 300 bp, 400 bp, 500 bp, 600 bp, 700 bp, 800 bp, 900 bp, 1000 bp, 1,500 bp, 2,000 bp, 3,000 bp, or 4,000 bp long. The nucleic acid sequence can encode a polypeptide that includes the amino sequence of SEQ ID NO:2, SEQ ID NO:10, SEQ ID NO:12, or SEQ ID NO:18. Examples include nucleotide sequences SEQ ID NO:1, SEQ ID NO:11, SEQ ID NO:13, and SEQ ID NO:19.

An isolated polypeptide within the invention can include the amino acid sequence of SEQ ID NO:2, SEQ ID NO:10, SEQ ID NO:12, or SEQ ID NO:18, or can differ from one of these sequences solely by one or more conservative amino acid substitutions. The polypeptides of the invention also embrace fusion proteins containing both (a) an amino acid sequence selected from the group consisting of SEQ ID NO:2, SEQ ID NO:10, SEQ ID NO:12, and SEQ ID NO:18, but lacking methionine at position 1 of said amino acid sequence; and (b) a heterologous leader peptide. Also included are isolated nucleic acid molecules encoding the fusion proteins.

The invention features methods of enhancing spreading of a macrophage or a monocyte in vitro. These methods include coculturing a monocyte or a macrophage and a T cell with one or more of the following agents: (a) an isolated attractin polypeptide with the amino acid sequence of SEQ ID NO:2, SEQ ID NO:10, SEQ ID NO:12, or SEQ ID NO:18; (b) a functional fragment of one or more of these attractin polypeptides; or (c) the polypeptide or the functional fragment, but with at least one conservative amino acid substitution.

The above polypeptides and nucleic acids can be used in a method of treating a mammal (e.g., a human) in need of an enhanced immune response. The method includes the step of delivering, to a tissue of a mammal where the tissue contains T cells and macrophages or monocytes, one of the above agents. The method can involve administration of the agent or a nucleic acid encoding the agent to the mammal. The human can be one suspected of being immunodeficient (e.g., one having common variable immunodeficiency) and/or of having cancer; and can be performed before, during, or after chemotherapy or radiation therapy.

The invention also embodies a method of inhibiting spreading of a macrophage or a monocyte in a mammal. The method includes administering to the mammal an isolated compound that binds to an attractin polypeptide, and interferes with its function. The product can be an antibody and the mammal can be a human, e.g., a human suspected of having an autoimmune disease or a transplant recipient.

The invention also features vectors including any of the isolated DNAs of the invention, e.g. a vector in which the nucleic acid sequence encoding the relevant polypeptide is operably linked to a regulatory element which allows expression of the coding sequence in a cell. Cultured cells including the above vectors can be used in methods of producing any of the polypeptides of the invention. These methods include culturing the appropriate cell and purifying the polypeptide from it.

The invention also features a method of identifying a compound that inhibits an immune response. The method includes: a) providing an isolated polypeptide containing an amino acid sequence selected from the group consisting of SEQ ID NO:2, SEQ ID NO:10, SEQ ID NO:12, and SEQ ID NO:18, or the same amino acid sequence but with one or more conservative amino acid substitutions; b) co-culturing a T cell and a macrophage or a monocyte with the isolated polypeptide and the test compound; c) determining whether the test compound inhibits spreading of the macrophage or the monocyte, as an indication that the test compound inhibits an immune response. Alternatively, the method can include: a) providing a test compound; b) combining the test compound, a T cell, a macrophage or a monocyte, and the isolated polypeptide; and c) determining whether the test compound enhances spreading of the macrophage or the monocyte, as an indication that the test compound inhibits an immune response.

Also within the invention is a method of identifying a compound that enhances an immune response. The method includes: a) providing a test compound; b) combining the test compound, a T cell, a macrophage or a monocyte, and an isolated polypeptide of the intention; and c) determining whether the test compound enhances spreading of the macrophage or the monocyte, as an indication that the test compound inhibits an immune response. Alternatively, the method can include: a) providing the isolated polypeptide; b) co-culturing a T cell and a macrophage or a monocyte with the isolated polypeptide and the test compound; c) determining whether the test compound inhibits spreading of the macrophage or the monocyte, as an indication that the test compound inhibits an immune response.

Also within the invention is an antibody (e.g., a scFv) that binds to a polypeptide with the amino acid sequence of SEQ ID NO:10, SEQ ID NO:12, or SEQ ID NO:18, but does not bind to CD26 or to a polypeptide with the sequence of SEQ ID NO:2.

The invention also features an ex vivo method of treating a mammal (e.g., a human patient) in need of an enhanced immune response. The method includes: a) providing a recombinant cell which is the progeny of a cell obtained from the mammal and has been transfected or transformed ex vivo with a nucleic acid encoding an "agent" or a functional fragment of the agent so that the cell expresses the agent or functional fragment; and b) administering the cell to the mammal. The "agent" is: (i) an attractin polypeptide that includes the amino acid sequence of SEQ ID NO:2, SEQ ID NO:10, SEQ ID NO:12, or SEQ ID NO:18; (ii) a functional fragment of the attractin polypeptide; or (iii) the polypeptide or the functional fragment, but with one or more conservative amino acid substitutions.

Another aspect of the invention is an isolated functional attractin fragment including at least amino acid residues 31–104 of SEQ ID NO:12 or SEQ ID NO:18, amino acid residues 1279–1301 of SEQ ID NO:12, amino acid residues 1219–1429 of SEQ ID NO:12, or amino acid residues 1302–1429 of SEQ ID NO:12.

"Polypeptide" and "protein" are used interchangeably and mean any peptide-linked chain of amino acids, regardless of length or post-translational modification. The invention also features attractin polypeptides with conservative substitutions. Conservative substitutions typically include substitutions within the following groups: glycine and alanine; valine, alanine, isoleucine, and leucine; aspartic acid and glutamic acid; asparagine, glutamine, serine and threonine; lysine, histidine and arginine; and phenylalanine and tyrosine.

The term "isolated" polypeptide or peptide fragment as used herein refers to a polypeptide or a peptide fragment which either has no naturally-occurring counterpart (e.g., a peptidomimetic), or has been substantially separated or purified from components which naturally accompany it, e.g., in tissues such as pancreas, liver, spleen, ovary, testis, muscle, joint tissue, neural tissue, gastrointestinal tissue, or body fluids such as blood, serum, or urine. Typically, the polypeptide or peptide fragment is considered "isolated" when it is at least 70%, by dry weight, free from the proteins and naturally-occurring organic molecules with which it is naturally associated. Preferably, a preparation of a polypeptide (or peptide fragment thereof) of the invention is at least 80%, more preferably at least 90%, and most preferably at least 99%, by dry weight, the polypeptide (or the peptide fragment thereof), respectively, of the invention. Thus, for example, a preparation of polypeptide x is at least 80%, more preferably at least 90%, and most, preferably at least 99%, by dry weight, polypeptide x. Since a polypeptide that is chemically synthesized is, by its nature, separated from the components that naturally accompany it, a synthetic polypeptide is by definition "isolated."

An isolated polypeptide (or peptide fragment) of the invention can be obtained, for example, by extraction from a natural source (e.g., from human tissues or bodily fluids); by expression of a recombinant nucleic acid encoding the peptide; or by chemical synthesis. A peptide that is produced in a cellular system different from the source from which it naturally originates is "isolated," because it will be separated from components which naturally accompany it. The extent of isolation or purity can be measured by any appropriate method, e.g., column chromatography, polyacrylamide gel electrophoresis, or HPLC analysis.

An "isolated DNA" means a DNA which either (a) has a non-naturally occurring sequence (e.g., a cDNA from a gene that naturally has introns), or (b) has a naturally occurring (i.e., genomic) sequence, but is free of the genes that flank the sequence in the genome of the organism in which the gene of interest naturally occurs. The term "isolated DNA" therefore includes a recombinant DNA incorporated into a vector, into an autonomously replicating plasmid or virus, or into the genomic DNA of a prokaryote or eukaryote at a site other than the site at which it occurs naturally. It also includes a separate molecule such as a cDNA; a genomic fragment; a fragment produced by polymerase chain reaction (PCR); a restriction fragment; a DNA encoding a non-naturally occurring mutein, fusion protein, or fragment of a given protein; or a nucleic acid which is a degenerate variant of a naturally occurring nucleic acid. In addition, it includes a recombinant nucleotide sequence that is part of a hybrid gene, i.e., a gene encoding a fusion protein.

"Spreading" of a macrophage or a monocyte, which occurs after exposure of the macrophage or monocyte to an attractin protein and a T cell, involves flattening of the macrophage or monocyte on a surface, expansion of the macrophage's or monocyte's margins, and an increase in the cell's surface area. The spread macrophage or monocytes may produce cellular processes visible microscopically. Macrophages and monocytes that have spread can be distinguished from, e.g., fibroblasts or T cells, by their expression of surface CD14.

As used herein, a "fragment" of an attractin polypeptide contains part but not all of the full-length polypeptide. Generally, fragments will be five or more amino acids in length. An antigenic fragment has the ability to be recognized and bound by an antibody.

As used herein, a "functional fragment" of an attractin polypeptide is a fragment of the polypeptide that has the ability to induce spreading of a macrophage or a monocyte in the presence of a T cell. Methods of establishing whether a fragment of an attractin molecule is functional are based upon those described herein for full-length polypeptides. For example, fragments of interest can be made by either recombinant, synthetic, or proteolytic digestive methods. Such fragments can then be isolated and tested for their ability to enhance spreading of macrophages or monocytes by procedures described herein.

As used herein, "operably linked" refers to an expression control sequence (e.g., a promoter, enhancer, or the like) linked co a coding sequence in a manner that permits the expression control sequence to control expression of the coding sequence.

As used herein, the term "antibody" refers not only to whole antibody molecules, but also to antigen-binding fragments, e.g., Fab, F(ab')$_2$, Fv, and single chain Fv fragments. Also included are chimeric antibodies.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention; e.g., enhancing immune responses in mammalian subjects, will be apparent from the following description, from the drawings and from the claims.

BRIEF DESCRIPTION OF THE DRAWINGS

FIG. 2 is a depiction of the amino acid sequence of soluble attractin-1 (SEQ ID NO:2). The sequences identified by N-terminal sequencing of tryptic and chymotryptic peptides are underlined.

FIGS. 3A–3B are photographs showing attractin mRNA expression in Northern blots of multiple tissue mRNA (FIG. 3A) and resting and PHA-activated PBMC total RNA (FIG. 3B). FIG. 3C is a photograph showing an ethidium bromide stained electrophoretic gel of 3.164 bp attractin DNA fragments obtained by PCR using three independent cDNA libraries as sources of templates.

FIGS. 4A–4C are diagrams showing the organization of soluble attractin-1 cDNA and peptide domains. FIG. 4A is a diagram of soluble attractin-1 cDNA. The bases shown in upper case at the origin represent bases satisfying the Kozak consensus. FIG. 4B shows a comparison of soluble attractin-1 protein domains and, motifs with those of C. elegans F33C8.1 protein. The horizontal bars depict the position of cysteines shared by both sequences. FIG. 4C shows a comparison of the putative catalytic serine motif of soluble attractin-1 with the catalytic serine motifs of other serine proteases. The shaded box indicates agreement with the consensus, '#' or exclusion from the shaded boxes indicates conflict, and 'X' indicates satisfaction by any amino acid. The parentheses enclose amino acids any of which would satisfy the consensus.

FIGS. 5A–5D are photomicrographs showing the intracellular localization of glycosylated soluble attractin-1 by immunogold electron microscopy using rabbit polyclonal antibody specific for soluble attractin-1; in resting T lymphocyte with no evidence of soluble attractin-1 expression (FIG. 5A); in T cells activated for 48 hr with PHA and in which, soluble attractin-1 is expressed in large vacuoles (FIG. 5B); in vesicles in which soluble attractin-1 localizes in an electron dense core (FIG. 5C); and in vesicles containing soluble attractin-1 breaking open at the cell surface, releasing soluble attractin-1 (FIG. 5D).

FIGS. 6A–6C are photographs showing expression of recombinant soluble attractin-1 and immunoprecipitation by antibody specific for natural soluble attractin-1. FIG. 6A shows a photograph of an SDS-PAGE gel of soluble attractin-1 transcribed and translated in vitro in the absence or presence of glycosyl transferases. FIG. 6B is a photograph of a Western blot (developed with antibody specific for myc) of lysates of 293T cells transiently-transfected with pSecTag2B-soluble attractin-1 or pSecTag2B vector control. FIG. 6C shows a photograph of an SDS-PAGE gel of soluble attractin-1 precipitated with pre-immune serum or polyclonal antibody specific for soluble attractin from lysates of CHO cells stably transfected with pSecTag2B-attractin.

FIGS. 7A–7D are photomicrographs showing that recombinant soluble attractin-1 mediates monocyte/macrophage spreading and T cell clustering. Resting PBMC were incubated for 48 hr without soluble attractin-1 (FIG. 7A) or with soluble attractin-1 at a concentration of 1 $\mu$g/ml (FIG. 7B), 2 $\mu$g/ml (FIG. 7C), or 5 $\mu$g/ml (FIG. 7D).

FIG. 8 is a depiction of the nucleotide sequence of soluble attractin-1 cDNA (SEQ ID NO:1).

FIG. 9 is a depiction of the amino acid sequence of membrane attractin-1 (SEQ ID NO:10).

FIG. 10 is a depiction of the nucleotide sequence of membrane attractin-1 encoding cDNA (SEQ ID NO:11).

FIG. 11 is a depiction of the amino acid sequence of soluble attractin-2 (SEQ ID NO:18).

FIG. 12 is a depiction of the nucleotide sequence of soluble attractin-2 encoding cDNA (SEQ ID NO:19).

FIG. 13 is a depiction of the amino acid sequence of membrane attractin-2 (SEQ TD NO:12).

FIG. 14 is a depiction of the nucleotide sequence of membrane attractin-2 encoding cDNA (SEQ ID NO:13).

DESCRIPTION OF THE INVENTION

The invention is based, in part, on the cloning of cDNA molecules encoding different overlapping regions of human soluble attractin-1, membrane attractin-1, soluble attractin-2, and membrane attractin-2. Contrary to initial indications when soluble attractin-1 was first studied, It was determined that there is no significant amino acid sequence homology between attractin and CD26, or any other characterized human protein. Both purified serum-derived and recombinant soluble attractin-1 induce the spreading of macrophages and monocytes that become the focus for the clustering of non-proliferating T lymphocytes. T lymphocytes use soluble attractin-1, at least, to marshall together the cells required to form a cluster of co-operating immune cells. Since membrane attractin-1 and the putative attractin-2 molecules contain all the functional domains of soluble attractin, it is likely that they have similar activity. Thus, attractin has an important role in the regulation of the immune response.

Figure 4A:
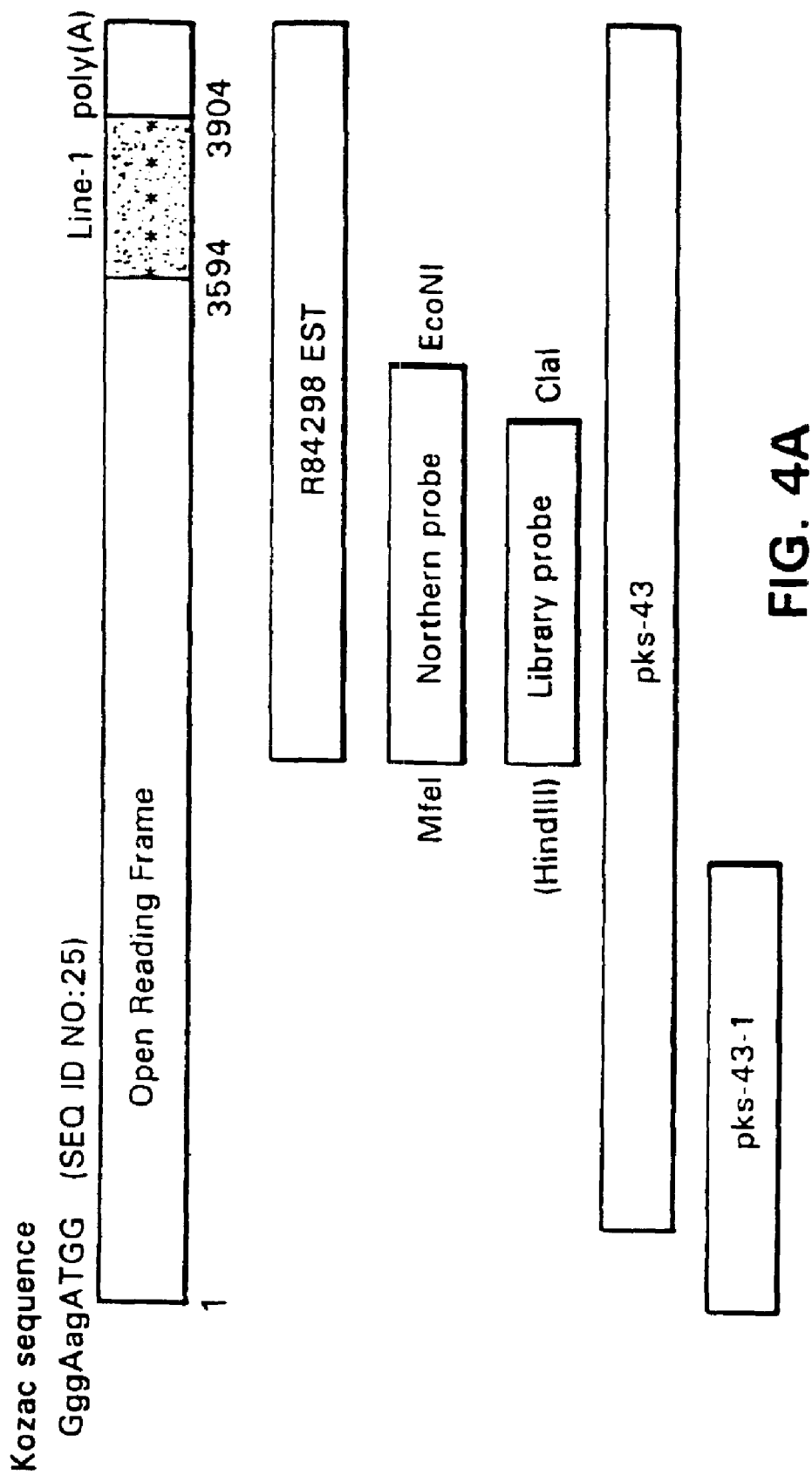

The various forms of attractin are encoded by alternatively spliced mRNA molecules transcribed from a single gene. The 134-kDa soluble attractin-1 protein includes a putative serine protease catalytic serine at amino acid residue 26, four EGF-like motifs, a CUB domain, a C-type lectin domain and a domain homologous with the ligand-binding region of the common cytokine receptor γ chain (FIG. 4C). Except for the latter two domains, the overall structure shares high homology with the C. elegans F33C8.1 protein, suggesting that attractin has evolved new domains and functions in parallel with the development of cell-mediated immunity. Membrane attractin-1 contains all these domains and, in addition, C-terminal transmembrane and cytoplasmic domains. Furthermore, attractin-2 has a 74 amino acid insertion, immediately after amino acid residue 30 of attractin-1. This insertion is likely to be important as a glycosylation targeting motif (e.g., a Golgi-targeting motif.

The experiments described in Examples 2, 5, and 10 below show that soluble attractin-1 mediates an interaction between T lymphocytes and monocytes, leading to adherence and spreading of the monocytes which become a focus for T lymphocyte clustering. No difference was observed in attractin mRNA expression between resting and activated PBMC, indicating that a regulatory step exists between transcription and glycosylation rather than in induction of de novo mRNA synthesis. Despite extensive N-glycosylation of the isolated serum (soluble) attractin, there are no consensus signal sequences encoded in the cDNA sequences encoding attractin. Another protein may chaperone attractin through the Golgi complex and endoplasmic reticulum. However, several proteins are known to be secreted without a signal peptide, including FGF-9 [Miyamoto et al. (1993) Mol. Cell. Biol. 13, 4251–4259], IL1-α and β [Rubartelli et al. (1990) EMBO J. 9, 1503–1510], FGF-1 [Tarantini et al. (1995) J. Biol. Chem. 270, 29039–29042], FGF-2 [Mignatti et al. (1992) J. Cell. Physiol. 151, 81–93], and platelet-derived endothelial cell growth factor [Mignatti et al. (1992) J. Cell. Physiol. 151, 81–93]. This has led to the proposal of alternative secretory pathways with slow exocytic release from large cytoplasmic pools [Rubartelli et al. (1997) In Unusual Secretory Pathways: from Bacteria to Man, eds. Kuchler et al. (R. G. Landes Co., Austin, Tex.), pp. 87–114]. The electron microscopy results described above confirm that the early activated T lymphocyte secretion of soluble attractin, at least, results from vesicular release at the plasma membrane.

Expression of attractin on the surface of activated T cells could involve any of the forms of the protein described herein. Thus, for example, surface could be the membrane form of attractin (-1 or -2) bound via its transmembrane domain to the T cell membrane. Alternatively, it could be soluble attractin (-1 or -2) that has been secreted into the milieu of the T cell and then binds via a cell-surface receptor, or via a non-specific hydrophobic interaction, to the T cell. In addition, attractin on the T cell could be soluble attractin (-1 or -2) that is in transit from the cytoplasm to the exterior of the T cell. The invention is not limited by any particular mechanism of T cell surface expression of attractin.

Proteins, such as attractin, containing EGF-like motifs are usually involved in extracellular signalling or cell guidance [Davis, C. G. (1990) New Biol. 2, 410–419]. Attractin also contains a motif representing the ligand-binding region of the cytokine receptor common γ chain [D'Andrea et al. (1990) Curr. Opin. Cell Biol. 2, 648–651]. In overall structure and organization of domains, attractin most closely resembles the CUB-containing protein BMP1 (bone morphogenic protein-1) which influences cell interactions during development [Li et al. (1996) Proc. Natl. Acad. Sci. USA 93, 5127–5130]. The acronym "CUB" derives from the names of the three prototypic proteins (complement component-1 r/s (Clr/s), U-EGF (epidermal growth factor), and BMP-1). The C-type lectin domain recognizes carbohydrate and is characteristic of the selectin family of proteins involved in adhesion of leukocytes to vascular endothelia. This domain is also characteristic of proteins involved in endocytosis for antigen processing in macrophages and dendritic cells [Weis et al. (1996) Ann. Rev. Biochem. 65, 441–473].

There is a high level of identity between attractin and the 143 kDa C. elegans F33C8.1 protein. The potential γ-chain ligand binding motif and C-type lectin domain present in attractin are missing in the C. elegans transcript, suggesting an evolutionary development in which the human form incorporated these new domains in parallel with the development of cell-mediated immunity.

Like CD26, soluble attractin-1 alone is unable to induce cell proliferation, but is able to enhance the proliferative response of PBL to recall antigens such as tetanus toxoid [Duke-Cohan et al. (1995) J. Biol. Chem. 270, 14107–14114; Duke-Cohan et al. (1996) J. Immunol. 156, 1714–1721]. Therefore, it appears that soluble attractin-1, and indeed the other attractin molecules described herein, modulate the interaction between T cells and macrophages and monocytes, permitting more rapid and/or more effective antigen presentation. It is likely that the minimal immunoregulatory unit consists of an antigen-presenting cell which acts as a focus for a cluster of T helper cells and effector cells [Stuhler et al. (1997) *Proc. Natl. Acad. Sci. USA* 94, 622–627]. The association of the three cell types is neither simultaneous nor random. Rather, the antigen-presenting cell clusters first with the helper T cells, and this cluster acts as a focus for recognition by effector cells [Ridge et al. (1998) *Nature* 393, 474–478]. In the absence of antigen, no proliferation occurs in soluble attractin-1-induced clusters of monocytes and T cells, but if a recall antigen such as tetanus toxoid is present, the clustering of cells maximizes the potential response to the antigen. Attractin may regulate local cytokine activity, either by influencing binding and presentation or by proteolytic modification. Soluble attractin-1 has recently been shown to cleave an N-terminal dipeptide which converts full-length RANTES 1–68 (consisting of amino acid residues 1–68), a potent monocyte chemoattractant, to RANTES 3–68 (consisting of residues 3–68), an equally potent inhibitor of monocyte chemotaxis [Proost et al. (1998) *J. Biol. Chem.* 273, 7222–7227]. Soluble attractin-1 has also been found to bind to macrophages and monocytes. It is possible that it is via this binding that attractin, in any of its forms, may regulate the activity of macrophages and monocytes. It could, for example, provide one of two or more requisite signals necessary for the induction of spreading and subsequent enhanced T-cell clustering. Alternatively, it could complement binding of another molecule to a receptor on macrophages/monocytes. Furthermore, it could form a bridge between T cells and macrophages/monocytes. Since membrane attractin (-1 and -2) has a cytoplasmic domain, it is likely that binding of a putative ligand to an extracellular region of membrane attractin results in signalling to the T cell. It should be understood, however, that the instant invention is not limited by a particular mechanism of action. The concatenation in attractin of domains related to regulation of cell interactions together with domains related to lymphokine/cytokine binding, the rapid upregulation of attractin cell surface expression by activated T cells, and the clear effect upon T cell-monocyte/macrophage association all suggest that attractin, either as a normal circulating serum protein or as a membrane bound protein, plays a significant role in the immune response in vivo.

Attractin Nucleic Acid Molecules

The attractin nucleic acid molecules of the invention can be cDNA, genomic DNA, synthetic DNA, or RNA, and can be double-stranded or single-stranded (i.e., either a sense or an antisense strand). Segments of these molecules are also considered within the scope of the invention, and can be produced, for example, by the polymerase chain reaction (PCR) or generated by treatment with one or more restriction endonucleases. A ribonucleic acid (RNA) molecule can be produced by in vitro transcription. Preferably, the nucleic acid molecules encode polypeptides that, regardless of length, are soluble under normal physiological conditions the membrane forms would not be soluble.

The nucleic acid molecules of the invention can contain naturally occurring sequences, or sequences that differ from those that occur naturally, but, due to the degeneracy of the genetic code, encode the same polypeptide (for example, the polypeptides with SEQ ID NOS:2, 10, 12, and 18). In addition, these nucleic acid molecules are not limited to coding sequences, e.g., they can include some or all of the non-coding sequences that lie upstream or downstream from a coding sequence.

The nucleic acid molecules of the invention can be synthesized (for example, by phosphoramidite-based synthesis) or obtained from a biological cell, such as the cell of a mammal. Thus, the nucleic acids can be those of a human, non-human primate (e.g., monkey) mouse, rat, guinea pig, cow, sheep, horse, pig, rabbit, dog, or cat.

In addition, the isolated nucleic acid molecules of the invention encompass segments that are not found as such in the natural state. Thus, the invention encompasses recombinant nucleic acid molecules, (for example, isolated nucleic acid molecules encoding any of the forms of attractin described herein) incorporated into a vector (for example, a plasmid or viral vector) or into the genome of a heterologous cell (or the genome of a homologous cell, at a position other than the natural chromosomal location). Recombinant nucleic acid molecules and uses therefor are discussed further below.

Certain nucleic acid molecules of the invention are antisense molecules or are transcribed into antisense molecules. These can be used, for example, to down-regulate translation of attractin mRNA within a cell.

Techniques associated with detection or regulation of genes are well known to skilled artisans and such techniques can be used to diagnose and/or treat disorders associated with aberrant attractin expression. Nucleic acid molecules of the invention are discussed further below in the context of their therapeutic utility.

An attractin family gene or protein can be identified based on its similarity to the relevant attractin gene or protein, respectively. For example, the identification can be based on sequence identity. The invention features isolated nucleic acid molecules which are at least 50% (or 55%, 65%, 75%, 85%, 95%, or 98%) identical to: (a) a nucleic acid molecule that encodes the polypeptide of SEQ ID NO:2, 10, 12, or 18; (b) the nucleotide sequence of SEQ ID NO:1, 11, 13, or 19; or (c) a nucleic acid molecule which includes a segment of at least: (i) 30 (e.g., at least 50, 60, 100, 125, 150, 175, 200, 250, 300, 325, 350, 375, 400, 425, 450, 500, 550, 600, 650, 700, 800, 900, 1000, 2000, 3000, or 3540) nucleotides of SEQ ID NO:1; (ii) 30 (e.g., at least 50, 60, 100, 125, 150, 175, 200, 250, 300, 325, 350, 375, 400, 425, 450, 500, 550, 600, 650, 700, 800, 900, 1000, 2000, 3000, 4000, or 4050) nucleotides of SEQ ID NO:11; (iii) 30 (e.g., at least 50, 60, 100, 125, 150, 175, 200, 250, 300, 325, 350, 375, 400, 425, 450, 500, 550, 600, 650, 700, 800, 900, 1000, 2000, 3000, 4000, or 4250) nucleotides of SEQ ID NO:13; or (iv) 30 (e.g., at least 50, 60, 100, 125, 150, 175, 200, 250, 300, 325, 350, 375, 400, 425, 450, 500, 550, 600, 650, 700, 800, 900, 1000, 2000, 3000, or 3800) nucleotides of SEQ ID NO:19. The invention also features nucleic acid molecules which include a nucleotide sequence encoding a polypeptide that is at least 65% (e.g., at least 70%, 75%, 25%, 95%, or 98%) identical to the amino acid sequence of SEQ ID NO:2, 10, 12, or 18.

The determination of percent identity between two sequences is accomplished using the mathematical algorithm of Karlin and Altschul, *Proc. Natl. Acad. Sci. USA* 90, 5873–5877, 1993. Such an algorithm is incorporated into the BLASTN and BLASTP programs of Altschul et al. (1990) *J. Mol. Biol.* 215, 403–410. BLAST nucleotide searches are performed with the BLASTN program, score=100, wordlength=12 to obtain nucleotide sequences homologous to attractin-encoding nucleic acids. BLAST protein searches are performed with the BLASTP program, score=50, wordlength=3 to obtain amino acid sequences homologous to attractin. To obtain gapped alignments for comparative purposes, Gapped BLAST is utilized as described in Altschul et al. (1997) *Nucleic Acids Res.* 25, 3389–3402. When utilizing BLAST and Gapped BLAST programs, the default parameters of the respective programs (e.g., XBLAST and NBLAST) are used (See http://www.ncbi.nlm.nih.gov).

Hybridization can also be used as a measure of homology between two nucleic acid sequences. An attractin-encoding nucleic acid sequence, or a portion thereof, can be used as hybridization probe according to standard hybridization techniques. The hybridization of an attractin probe to DNA from a test source (e.g., a mammalian cell) is an indication of the presence of attractin DNA in the test source. Hybridization conditions are known to those skilled in the art and can be found in Current Protocols in Molecular Biology, John Wiley & Sons, N.Y., 6.3.1–6.3.6, 1991. Moderate hybridization conditions are defined as equivalent to rod hybridization in 2× sodium chloride/sodium citrate (SSC) at 30° C., followed by one or more washes in 1× SSC, 0.1% SDS at 50–60° C. Highly stringent conditions are defined as equivalent to hybridization in 6× sodium chloride/sodium citrate (SSC) at 45° C., followed by one or more washes in 0.2× SSC, 0.1% SDS at 50–65° C.

The invention also encompasses: (a) vectors that contain any of the foregoing attractin-related coding sequences and/or their complements (that is, "antisense" sequence); (b) expression vectors that contain any of the foregoing attractin-related coding sequences operatively associated with any transcriptional/translational regulatory elements (examples of which are given below) necessary to direct expression of the coding sequences; (c) expression vectors containing, in addition to sequences encoding an attractin polypeptide, nucleic acid sequences that are unrelated to nucleic acid sequences encoding attractin, such as molecules encoding a reporter, marker, or a signal peptide, e.g., fused to attractin; and (d) genetically engineered host cells that contain any of the foregoing expression vectors and thereby express the nucleic acid molecules of the invention.

Recombinant nucleic acid molecules can contain a sequence encoding a soluble attractin membrane attractin, or attractin having an heterologous signal sequence. The full length attractin polypeptide, a domain of attractin, or a fragment thereof may be fused to additional polypeptides, as described below. Similarly, the nucleic acid molecules of the invention can encode the mature form of attractin or a form that includes an exogenous polypeptide which facilitates secretion.

The transcriptional/translational regulatory elements referred to above and which are further described below, include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase (neo$^r$, C418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, additional sequences that can serve the function of a marker or reporter. Generally, the hybrid polypeptide will include a first portion and a second portion; the first portion being an attractin polypeptide and the second portion being, for example, the reporter described above or an immunoglobulin constant region.

The expression systems that may be used for purposes of the invention include, but are not limited to, microorganisms such as bacteria (for example, *E. coli* and *B. subtilis*) transformed with recombinant bacteriophage DNA, plasmid DNA, or cosmid DNA expression vectors containing the nucleic acid molecules of the invention; yeast (for example, *Saccharomyces* and *Pichia*) transformed with recombinant yeast expression vectors containing the nucleic acid molecules of the invention (preferably containing the nucleic acid sequence encoding attractin (contained within SEQ ID NOS:2, 10, 12, or 18); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, T1 plasmid) containing attractin nucleotide sequences; or mammalian cell systems (for example, COS, CHO, BHK, 293, VERO, HeLa, MDCK, WI38, and NIP 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal, transfected with a plasmid vector or infected with a viral vector.

Polypeptides and Polypeptide Fragments

The polypeptides of the invention include soluble attractin-1 and -2, membrane attractin-1 and -2, and functional fragments of these polypeptides. The polypeptides embraced by the invention also include fusion proteins which contain either full-length attractin (any of the forms) or a functional fragment of it fused to unrelated amino acid sequence. The unrelated sequences can be additional functional domains or signal peptides. Signal peptides are described in greater detail and exemplified below.

The polypeptides can be purified from natural sources (e.g., blood, serum plasma, tissues or cells such as T cells or any cell that naturally produces attractin). Smaller peptides (less than 50 amino acids long) can also be conveniently synthesized by standard chemical means. In addition, both polypeptides and peptides can be produced by standard in vitro recombinant DNA techniques and in vivo recombination/genetic recombination (e.g., transgenesis), using the nucleotide sequences encoding the appropriate polypeptides or peptides. Methods well known to those skilled in the art can be used to construct expression vectors containing relevant coding sequences and appropriate transcriptional/translational control signals. See, for example, the techniques described in Sambrook et al., Molecular Cloning: A Laboratory Manual (2nd Ed.) [Cold Spring Harbor Laboratory, N.Y., 1989], and Ausubel et al., Current Protocols in Molecular Biology, [Green Publishing Associates and Wiley Interscience, N.Y., 1989].

Polypeptides and fragments of the invention also include those described above, but modified for in vivo use by the addition, the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Also of interest are peptidomimetic compounds that are designed based upon the amino acid sequences of the functional peptide fragments. Peptidomimetic compounds are synthetic compounds having a three-dimensional conformation (i.e., a "peptide motif") chat is substantially the same as the three-dimensional conformation of a selected peptide. The peptide motif provides the peptidomimetic compound with the ability to induce macrophage/monocyte spreading in a manner qualitatively identical to that of the attractin functional peptide fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Methods of Therapy

The methods of the invention involve combining a macrophage/monocyte, an attractin molecule of the invention, and a T cell, in order to induce spreading of macrophages/monocytes. The T cell can be a CD4+ T cell or a CD8+ T cell. The attractin molecule can be added to the solution containing the cells or it can be expressed on the surface of a T cell, e.g., the T cell that is added to the combined attractin and macrophages/monocytes. The methods can be performed in vitro, in viva, or ex vivo. In vitro application of attractin can be useful, for example, in basic scientific studies of immune mechanisms or for production of macrophages with increased ability to activate T cells for use in studies on macrophage/monocyte function. Furthermore, attractin could be added to in vitro assays (e.g., in T cell proliferation assays) designed to test for immunity to an antigen of interest in a subject from which the T cells were obtained. Addition of attractin to such assays would be expected to result in a more potent, and therefore more readily detectable, in vitro response. However, the methods of the invention will preferably be in vivo or ex vivo (see below).

The attractin proteins and variants thereof are generally useful as immune response-stimulating therapeutics, as described in International Application No. WO 96/38550 (published Dec. 5, 1996), which is incorporated by reference herein in its entirety. For example, the polypeptides of the invention can be used for treatment of disease conditions characterized by immunosuppression: e.g., cancer, AIDS or AIDS-related complex, other virally or environmentally-induced conditions, and certain congenital immune deficiencies. The compounds may also be employed to increase immune function that has been impaired by the use of radiotherapy of immunosuppressive drugs such as certain chemotherapeutic agents, and therefore are particularly useful when given in conjunction with such drugs or radiotherapy. These methods of the invention can be applied to a wide range of species, e.g., humans, non-human primates, horses, cattle, pigs, sheep, goats, dogs, cats, rabbits, quinea pigs, hamsters, rats, and mice.

In Vivo Approaches

In one in vivo approach, the attractin polypeptide (or a functional fragment thereof) itself is administered to the subject. Generally, the compounds of the invention will be suspended in a pharmaceutically-acceptable carrier (e.g., physiological saline) and administered orally or by intravenous infusion, or injected subcutaneously, intramuscularly, intraperitoneally, intrarectally, intravaginally, intranasally, intragastrically, intratracheally, or intrapulmonarily. They are preferably delivered directly to an appropriate lymphoid tissue (e.g. spleen, lymph node, or mucosal-associated lymphoid tissue (MALT)). The dosage required depends on the choice of the route of administration, the nature of the formulation, the nature of the patient's illness, the subject's size, weight, surface area, age, and sex, other drugs being administered, and the judgment of the attending physician. Suitable dosages are in the range of 0.01–100.0 µg/kg. Wide variations in the needed dosage are to be expected in view of the variety of polypeptides and fragments available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of the polypeptide in a suitable delivery vehicle (e.g., ????? polymeric microparticles or implantable devices) may increase the efficiency of delivery, particularly for oral delivery.

Alternatively, a polynucleotide containing a nucleic acid sequence encoding the attractin polypeptide or functional fragment can be delivered to an appropriate cell of the animal. Expression of the coding sequence will preferably be directed to lymphoid tissue of the subject by, for example, delivery of the polynucleotide to the lymphoid tissue. This can be achieved by, for example, the use of a polymeric, biodegradable macroparticle or microcapsule delivery vehicle, sized to optimize phagocytosis by phagocytic cells such as macrophages. For example, PLGA (poly-lacto-co-glycolide) microparticles approximately 1–10 µm in diameter can be used. The polynucleotide is encapsulated in these microparticles, which are taken up by macrophages and gradually biodegraded within the cell, thereby releasing the polynucleotide. Once released, the DNA is expressed within the cell. A second type of microparticle is intended not to be taken up directly by cells, but rather to serve primarily as a slow-release reservoir of nucleic acid that is taken up by cells only upon release from the micro-particle through biodegradation. These polymeric particles should therefore be large enough to preclude phagocytosis (i.e., larger than 5 μm and preferably larger than 20 μm). Microparticles useful for nucleic acid delivery, methods for making them, and methods of use are described in greater detail in U.S. Pat. No. 5,783,567, incorporated herein by reference in its entirety.

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al. (1995), *J. Mol. Med.* 73, 479]. Alternatively, lymphoid tissue specific targeting can be achieved by the use of lymphoid tissue-specific transcriptional regulatory elements (TRE) such as a B lymphocyte, T lymphocyte, or dendritic cell specific TRE. Lymphoid tissue specific TRE are known [Thompson et al. (1992), *Mol. Cell. Biol.* 12, 1043–1053; Todd et al. (1993), *J. Exp. Med.* 177, 1663–1674; Penix et al. (1993), *J. Exp. Med.* 178, 1483–1496]. Delivery of "naked DNA" (i.e., without a delivery vehicle) to an intramuscular, intradermal, or subcutaneous site, is another means to achieve in vivo expression.

In the relevant polynucleotides (e.g., expression vectors) the nucleic acid sequence encoding the attractin polypeptide or functional fragment of interest with an initiator methionine and optionally a targeting sequence is operatively linked to a promoter or enhancer-promoter combination.

Short amino acid sequences can act as signals to direct proteins to specific intracellular compartments. For example, hydrophobic signal peptides (e.g., MAISGVPV-LGFFIIAVLMSAQESWA (SEQ ID NO:14)) are found at the amino terminus of proteins destined for the ER. While the sequence KFERQ (SEQ ID NO:15) (and other closely related sequences) is known to target intracellular polypeptides to lysosomes, other sequences (e.g., MDDQRDLISN-NEQLP (SEQ ID NO:16) direct polypeptides to endosomes. In addition, the peptide sequence KDEL (SEQ ID NO:17) has been shown to act as a retention signal for the ER. Each of these signal peptides, or a combination thereof, can be used to traffic the attractin polypeptides or functional fragments of the invention as desired. DNAs encoding the attractin polypeptides or functional fragments containing targeting signals will be generated by PCR or other standard genetic engineering or synthetic techniques. Targeting sequences are described in greater detail in U.S. Pat. No. 5,827,516, incorporated herein by reference in its entirety.

A promoter is a TRE composed of a region of a DNA molecule, typically within 100 base pairs upstream of the point at which transcription starts. Enhancers provide expression specificity in terms of time, location, and level. Unlike a promoter, an enhancer can function when located at variable distances from the transcription site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles which are suitable for administration to a human, e.g., physiological saline. A therapeutically effective amount is an amount of the polynucleotide which is capable of producing a medically desirable result in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

Ex Vivo Approaches

Peripheral blood leukocytes can be withdrawn from the patient or a suitable donor and treated ex vivo with the attractin protein or polypeptide fragment (whether in soluble form or attached to a sold support by standard methodologies). The leukocytes containing newly-activated monocytes are then introduced into the same or a different patient.

An alternative ex vivo strategy can involve transfecting or transducing cells obtained from the subject with a polynucleotide encoding an attractin polypeptide or functional fragment-encoding nucleic acid sequences described above. The transfected or transduced cells are then returned to the subject. While such cells would preferably be lymphoid cells, they could also be any of a wide range of types including, without limitation, fibroblasts, bone marrow cells, macrophages, monocytes, dendritic cells, epithelial cells, endothelial cells, keratinocytes, or muscle cells in which they act as a source of the attractin polypeptide or functional fragment for as long as they survive in the subject. The use of lymphoid cells would be particular advantageous in that such cells would be expected to home to lymphoid tissue (e.g., lymph nodes or spleen) and thus the attractin polypeptide or functional fragment would be produced in high concentration at the site where they exert their effect, i.e., enhancement of an immune response. In addition, if T cells are used, the T cell expressing the exogenous attractin molecule can be the T cell that is required, together with attractin, to induce spreading and activation of macrophages or monocytes. The attractin can be secreted by the T cell or expressed on the surface of the T cell. The same genetic constructs and trafficking sequences described for the in vivo approach can be used for this ex vivo strategy.

The ex viva methods include the steps of harvesting cells from a subject, culturing the cells, transducing them with an expression vector, and maintaining the cells under conditions suitable for expression of the attractin polypeptide or functional fragment. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced are then selected, for example, for expression of the coding sequence or of a drug resistance gene. The cells may then be lethally irradiated (if desired) and injected or implanted into the patient.

Methods of Screening for Compounds that Inhibit or Enhance Immune Responses.

The invention provides methods for testing compounds (small molecules or macromolecules) that inhibit or enhance an immune response. Such a method could involve, e.g., culturing macrophages or monocytes with: (a) any of the attractin molecules of the invention, (b) T cells; and (c) a candidate compound. The attractin molecule can be in solution or membrane bound (e.g., expressed on the surface of the T cells) and it can be natural or recombinant. Furthermore, it can be a functional fragment of an attractin molecule. Compounds that inhibit macrophage or monocyte spreading will likely be compounds that inhibit an immune response while those that enhance macrophage and monocyte spreading will likely be compounds that enhance an immune response. Instead of testing for an effect of a compound on macrophage or monocyte spreading, the ability of the compound to inhibit or enhance induction of B7.1 or MHC class II molecule expression on the macrophage could also be measured.

The invention also relates to using attractin or functional fragments thereof to screen for immunomodulatory compounds that can interact with attractin. One of skill in the art would know how to use standard molecular modeling or other techniques to identify small molecules that would bind to the unique sites of attractin described herein. On such example is provided in Broughton (1997) Curr. Opin. Chem. Biol. 1, 392–398.

A candidate compound whose presence requires at least 1.5-fold (e.g., 2-fold, 4-fold, 6-fold, 10-fold, 150-fold, 1000-fold, 10,000-fold, or 100,000-fold) more attractin in order to achieve macrophage or monocyte spreading than in the absence of the compound can be useful for inhibiting an immune response. On the other hand, a candidate compound whose presence requires at least 1.5 fold (e.g., 2-fold, 4-fold, 6-fold, 10-fold, 100-fold, 1000-fold, 10,000 fold, or 100,000-fold) less attractin to achieve macrophage or monocyte spreading than in the absence of the compound can be useful for enhancing an immune response. Compounds capable of interfering with or modulating attractin function are good candidates for immunosuppressive immunoregulatory agents, e.g., to modulate an autoimmune response or suppress allogeneic or xenogeneic graft rejection.

Attractin Antibodies

The invention features antibodies that bind to any or all of the described attractin polypeptides or fragments of such polypeptides. Such antibodies can be polyclonal antibodies present in the serum or plasma of animals (e.g., mice, rabbits, rats, guinea pigs, sheep, horses, coats, cows, or pigs) which have been immunized with the relevant attractin polyeptide or peptide fragment using methods, and optionally adjuvants, known in the art. Such polyclonal antibodies can be isolated from serum or plasma by methods known in the art. Monoclonal antibodies that bind to the above polypeptides or fragments are also embodied by the invention. Methods of making and screening monoclonal antibodies are well known in the art.

Once the desired antibody-producing hybridoma has been selected and cloned, the resultant antibody can be produced in a number of methods known in the art. For example, the hybridoma can be cultured in vitro in a suitable medium for a suitable length of time, followed by the recovery of the desired antibody from the supernatant. The length of time and medium are known or can be readily determined.

Additionally, recombinant antibodies specific for attractin, such as chimeric and humanized monoclonal antibodies comprising both human and non-human portions, are within the scope of the invention. Such chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) *Science* 240, 1041–43; Liu et al. (1987) *J. Immunol.* 139, 3521–26; Sun et al. (1987) *PNAS* 84, 214–18; Nishimura et al. (1987) *Canc. Res.* 47, 999–1005; Wood et al. (1985) *Nature* 314, 446–49; Shaw et al. (1988) *J. Natl. Cancer Inst.* 80, 1553–59; Morrison, (1985) *Science* 229, 1202–07; Oi et al. (1986) *BioTechniques* 4, 214; Winter, U.S. Pat. No. 5,225,539; Jones et al. (1986) *Nature* 321, 552–25; Veroeyan et al. (1988) *Science* 239, 1534; and Beidler et al. (1988) *J. Immunol.* 141, 4053–60.

Also included within the scope of the present invention are antibody fragments and derivatives which contain at least the functional portion of the antigen binding domain of an antibody that binds specifically to attractin. Antibody fragments that contain the binding domain of the molecule can be generated by known techniques. For example, such fragments include, but are not limited to: $F(ab')_2$ fragments which can be produced by pepsin digestion of antibody molecules; Fab fragments at which can be generated by reducing the disulfide bridges of $F(ab')_2$ fragments; and Fab fragments which can be generated by treating antibody molecules with papain and a reducing agent. See, e.g., National Institutes of Health, 1 *Current Protocols In Immunology*, Coligan et al., ed. §§ 2.8, 2.10 (Wiley Interscience, 1991). Antibody fragments also include Fv (e.g., single chain Fv (scFv)) fragments, i.e., antibody products in which there are no constant region amino acid residues. Such fragments can be produced, for example, as described in U.S. Pat. No. 4,642,334.

The following examples are meant to illustrate, not limit, the invention.

EXAMPLE 1

Materials and Methods

Cell techniques: PBMC, erythrocyte resetting ($E^+$) T cells and erythrocyte non-resetting ($E^-$) monocytes/B cells were purified as described previously [Morimoto et al. (1985) *J. Immunol.* 134, 3762–3769]. CHO ($dhfr^-$) cells and the Jurkat T cell line were obtained from the American Type Culture Collection (ATCC, Manassas, Va.). 293T cells were obtained from Dr. B. Mayer (Children's Hospital, Boston, Mass.). All cell lines were maintained in RPMI 1640 containing 10% fetal bovine serum. For assessing the biological effects of soluble attractin-1, leukocytes were cultured in serum-free AIM V medium (Life Technologies Inc., Gaithersburg, Md.) in 48-well plates (Costar, Cambridge, M). For cell activation, $E^+$ lymphocytes ($10^6$/ml) supplemented with 0.1% $E^-$ cells were incubated in AIM V medium together with phytohemagglutinin (PHA, 1 μg/ml; Murex, Dartford, U.K.) for 48 hr. Cell proliferation was assessed using [$^3$H]-thymidine incorporation as described previously [Duke-Cohan et al. (1995) *J. Biol. Chem.* 270, 14107–14114].

RNA/DNA preparation and analysis: mRNA was isolated using the Poly(A)Pure kit (Ambion, Austin, Tex.). Northern blots were prepared using standard denaturing formaldehyde agarose electrophoresis techniques and transferred to Gene-Screen Plus (NEN-Dupont, Boston, Mass.). The EST clone R84298 was obtained from the I.M.A.G.E. consortium (Lennon et al. (1996) *Genomics* 33, 151–152) through the ATCC. Both fetal liver cDNA libraries (λgt11 and Marathon cDNA) were obtained from Clontech (Palo Alto, Calif.). The J5DC T cell library was prepared from 48 hr PHA-activated T lymphocyte mRNA using the Superscript Choice system (Life Technologies Inc.) and ligated into pcDNAI/Amp (Invitrogen, Carlsbad, Calif.). The GF activated T cell library was prepared and ligated into pCDM8 as described previously [Hall et al. (1996) Proc. Natl. Acad. Sci. USA 93, 11780–11785]. The expression vectors, pRc/CMV and pSecTag2B were obtained from Invitrogen. All labeling of DNA probes with $^{32}$P-dCTP was by random priming (Life Technologies Inc.).

Isolation of cDNA encoding soluble attractin-1: Tryptic/chymotryptic peptides were prepared and analyzed as described previously [Duke-Cohan et al. (1995) J. Biol. Chem. 270, 14107–14114]. A multiple human hematopoietic tissue Northern blot (Clontech) was screened using the 1.2 kb MfeI/EcoNI R84298 EST. The λgt11-fetal liver library was screened using the 1.3 kb ClaI/HindIII R84298 EST which yielded the pks-43 (4 kb) fragment. Hind III digestion of pks-43 released a 5' 982 pb fragment which was used to rescreen the fetal liver library and a further 5' sequence, including the putative start codon, was identified (pks-43-1). In order to produce full length recombinant soluble attractin-1, PCR-generated fragments encoding soluble attractin-1 were cloned into the expression vector, pRc/CMV. Using the pks-43-1 as template, a PCR (PCR1) was carried using the following primers: CCCAAGCTTGGGATGGGTGTCGGGCTCAGCCCGC-forward (SEQ ID NO:3) and, ATAAGAATGCG-GCGCTAAACTCATTGTTCAGT TTCGACCTG-reverse (SEQ ID NO:4). A second PCR(PCR2) using the pks-43 fragment as template was carried out using the following primers: CCCAAGCTTGGGATGGTGGCCGCAGCGGCGGC-forward, (SEQ ID NO:5) and CCAGGTCCATCTGTCACAAACCCAG-reverse (SEQ ID NO:6). The fragment obtained from PCR1 was digested with HindIII and NaeI and that from PCR2 was digested with NaeI and NotI. The two digested fragments were then cloned together into HindIII/Not-I-digested pRc/CMV. For production of recombinant soluble attractin-1 with disabled start and stop codons into pSecTag2B, a 3.5 kb fragment was amplified from pRc/CMV-attractin using the Advantage GC cDNA PCR system (Clontech) and the primers GTGCGT-GAAGCTTGTACCGGCAACTGAGGCAA GGCTGA-forward (SEQ ID NO:7) and GTAGTTTTAAGTC-CACGTTTGACTTCGCCGGCG GCGTG-reverse (SEQ ID NO:8), digested with Hind III/Not I, and ligated into pSecTag2B.

Expression of functional soluble attractin-1: The Quick TnT system together with canine microsomal membranes (Promega, Madison, Wis.) was used for in vitro transcription and translation. 293T cells were transfected transiently using pSecTag2B-soluble attractin complexed with Lipofectamine Plus (Life Technologies Inc.) and assayed for soluble attractin-1 expression at 48 hr. For Western blotting experiments, cells were lysed in boiling SDS-PAGE sample buffer (x2) and samples run on SDS-PAGE gels, transferred to nitrocellulose by electroblotting, and the membranes were blocked with Tris-buffered saline containing 0.1% Tween 20 and 1% BSA. Blots were incubated with murine antibody specific for myc (1:5000; Amersham, Arlington Heights, Ill.) or with a horseradish peroxidase (HRP) monoclonal antibody specific for myc (1:2000; Invitrogen) and detected using the Phototope chemiluminescent system (New England Biolabs). For immunoprecipitation experiments, the cells were solubilized in lysis buffer (1% Triton X-1000, 0.1% NP-40, 150 mM NaCl). Lysates were precleared with mIgG-agarose beads (Sigma) followed by incubation with Protein A-purified polyclonal rabbit antibody specific for soluble attractin or Protein A-purified normal preimmune IgG. Antibody complexes were isolated by incubation with agarose beads conjugated with antibody specific for rabbit IgG (Sigma) followed by boiling in 2x SDS-PAGE loading buffer, after which the procedure was identical with that described for Western transfers above.

For stable transfections, pSecTag2B-soluble attractin-1 was introduced into CHO cells by electroporation (250V, 1600 µF) using the Cell-Porator apparatus (Lite Technologies) and selection with zeocin (500 µg/ml; Invitrogen). To purify recombinant soluble attractin-1, cells were lysed and loaded onto a Talon Superflow metal affinity resin (Clontech) and eluted with 250 mM imidazole. DPPIV activity of the recombinant soluble attractin-1 was determined using gly-pro-pNA as substrate as described previously [Duke-Cohan et al. (1995) J. Biol. Chem. 270, 14107–14114].

Binding assays: PBMC were activated for 24 hr with PHA in AIM V medium as described above, washed in AIM V and $10^6$ cells/100 µl were incubated for 1 hr at 4° C. with doubling dilutions of $^{125}$I-labeled soluble attractin [Duke-Cohan et al. (1996) J. Immunol. 156, 1714–1721], starting at 2 µg/ml ($10^7$ dpm/µg). The cells were washed with cold PBS, and the pellet and first wash supernatant were counted by scintillation. Results were analyzed by Scatchard analysis.

Electron microscopy: Cells were prepared as described previously [Xu et al. (1994) J. Histochem. Cytochem. 42, 1365–1376] and were analyzed by transmission electron microscopy (model JEM 100 CX II; JEOL, Peabody, Mass.).

EXAMPLE 2

Figure 1A:
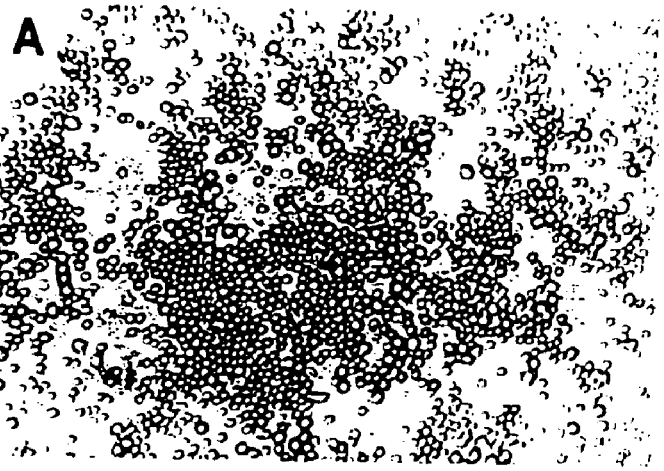
FIGS. 1A–1F are photomicrographs showing monocyte spreading and T cell clustering after a 48 hr incubation of peripheral blood mononuclear cells (PBMC) with various concentrations of purified, natural soluble attractin-1. PBMC were incubated with no soluble attractin-1 (FIG. 1A) or soluble attractin-1 at a concentration of 0.5 $\mu$g/ml (FIG. 1B), 1 $\mu$g/ml (FIG. 1C), 2 $\mu$g/ml (FIG. 1D), 5 $\mu$g/ml (FIG. 1E), or 10 $\mu$g/ml (FIG. 1F).
Figure 1B:
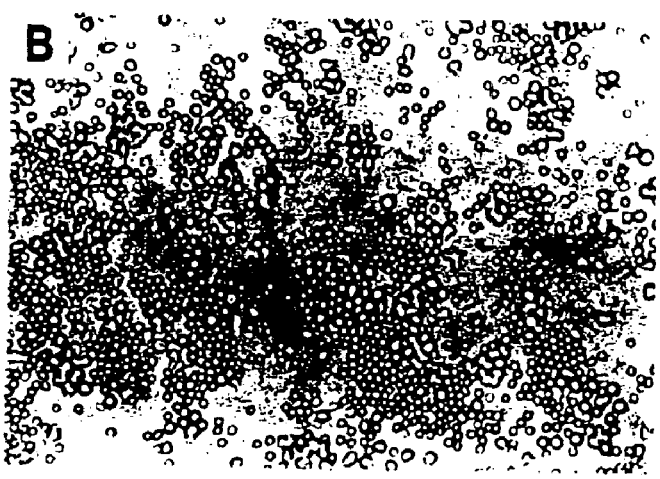
Figure 1C:
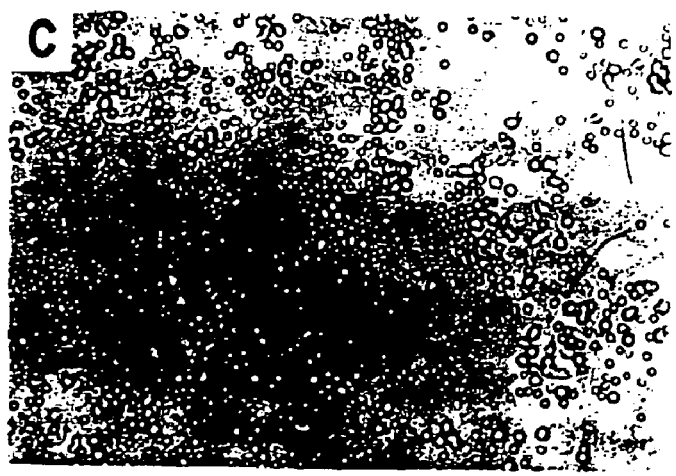
Figure 1D:
Figure 1E:
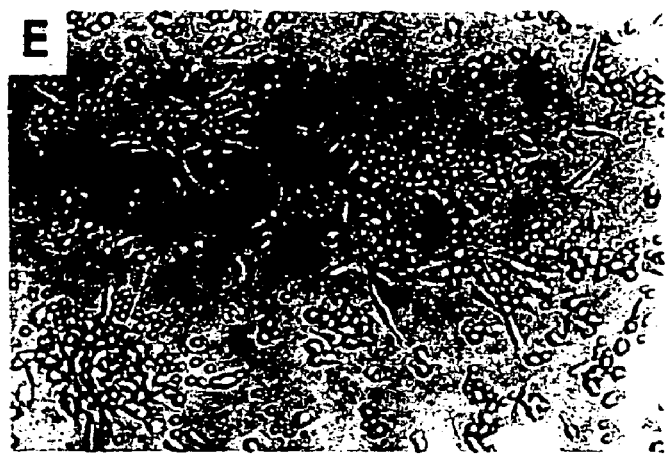
Figure 1F:
Figure 1G:
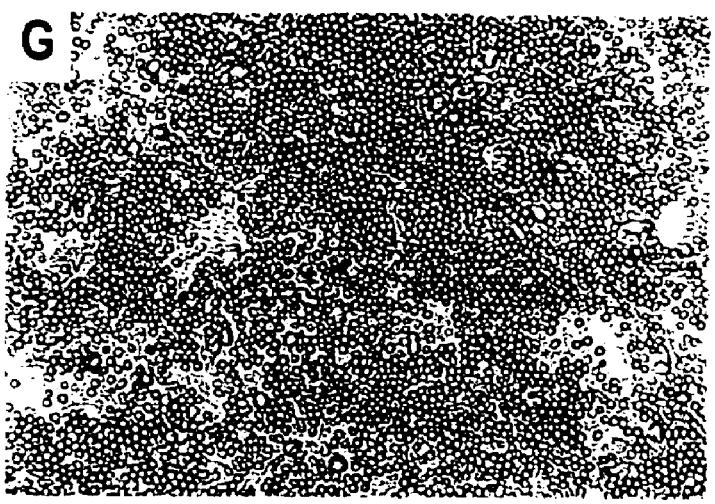
FIGS. 1G–1I, are photomicrographs of cells from cultures to which soluble attractin-1 (10 $\mu$g/ml) had been added. The cells in the cultures, which were incubated for 48 hours, were PBMC separated into E$^+$ T lymphocytes (FIG. 1G), E$^-$ monocytes/B cells (FIG. 1H), and E$^+$ T lymphocytes remixed with E$^-$ monocytes/B cells (FIG. 1I).
Figure 1H:
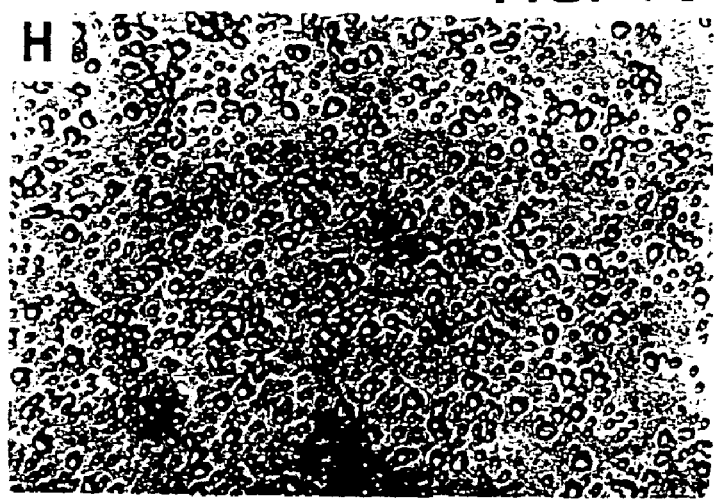
Figure 1I:
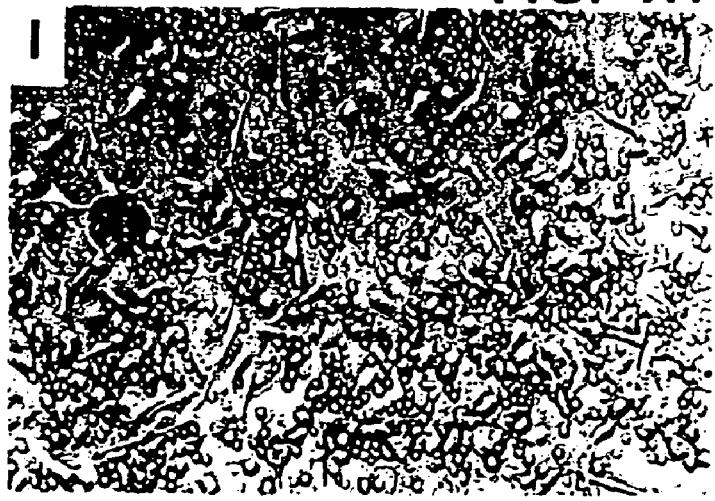

Soluble Attractin-1 Binds Strongly to T Cells and Induces Spreading of Monocytes Purified serum (soluble) attractin-1 had previously been found to enhance the proliferative responses of PBMC to recall antigens such as tetanus toxoid. In the absence of the antigen, the soluble attractin-1 had no effect. Scatchard analysis showed that about 1,000 molecules of soluble attractin-1 bound to the surface of a resting T cell, and about 2,000 molecules to a PHA-activated T cell, with a $K_d$ for both of between 5 and 50 pM which is indicative of a specific, high affinity interaction. To determine whether the binding of soluble attractin-1 had a functional effect upon cells, a population of PBMC was tested for morphological changes due to the presence or absence of soluble attractin-1. It was found that, within 48 hr of addition to PBMC in serum-free medium, soluble attractin-1 caused spreading of adherent macrophage-like cells, generating long processes to which lymphocytes attached. This process was dose-dependent, with the maximum effect occurring between 5 to 10 µg/ml soluble attractin-1 (FIGS. 1A–1F). Soluble attractin-1 had no effect on $E^+$ lymphocytes alone (FIG. 1G) or $E^-$ monocytes/B lymphocytes alone (FIG. 1H), but clustering occurred if the $E^+$ T and $E^-$ populations were combined (FIG. 1I). After non-adherent cells had been washed away, the adherent cells were released by incubation with EDTA in PBS. By using immunofluorescence analysis, it was found that the small adherent cells were exclusively $CD3^+$ T cells, while the aJ large adherent cells were predominantly $CD14^+$ monocytes/macrophages.

EXAMPLE 3

Cloning of cDNA Encoding Soluble Attractin-1 and Analysis of the Deduced Protein Structure Peptide sequences within the soluble attractin-1 polypeptide were identified with a view to cloning cDNA encoding it. Natural soluble attractin-1 was purified to homogeneity and the N-termini of 16 proteolytic peptides (underlined in FIG. 2) were sequenced. One of the sequences (17 amino acids) was 100% identical to part of the derived amino acid sequence of a translated 3' EST sequence (R84298) which codes for 1.9 kb sequence including the 3' end of soluble attractin. By using this sequence as a probe, two mRNA species of 4.4 kb and 8–9 kb were detected, both of which were heavily represented in fetal liver and spleen (FIG. 3A). The larger form was dominant in thymus while the smaller form was dominant in PBMC. No upregulation of attractin mRNA transcription was observed in activated T cells (FIG. 3B).

Based on mRNA expression, a fetal liver library was screened, and a 982 bp 5' fragment derived from the longest clone (pks43) was used to rescreen the library, leading to identification of a further clone containing additional 5' sequence (pks43-1). Sequencing of both overlapping clones yielded an open reading frame (ORF) of 3.594 kb that encoded all 16 peptides previously identified. PCR amplification of the main body of soluble attractin-1 cDNA from the two activated T cell libraries and from the fetal liver library produced PCR products of the same size, i.e., about 3 kb (FIG. 3C). The nucleotide sequence coding for soluble attractin-1 (SEQ ID NO:2) has been deposited in GenBank and given the accession number AF034957.

Figure 4B:
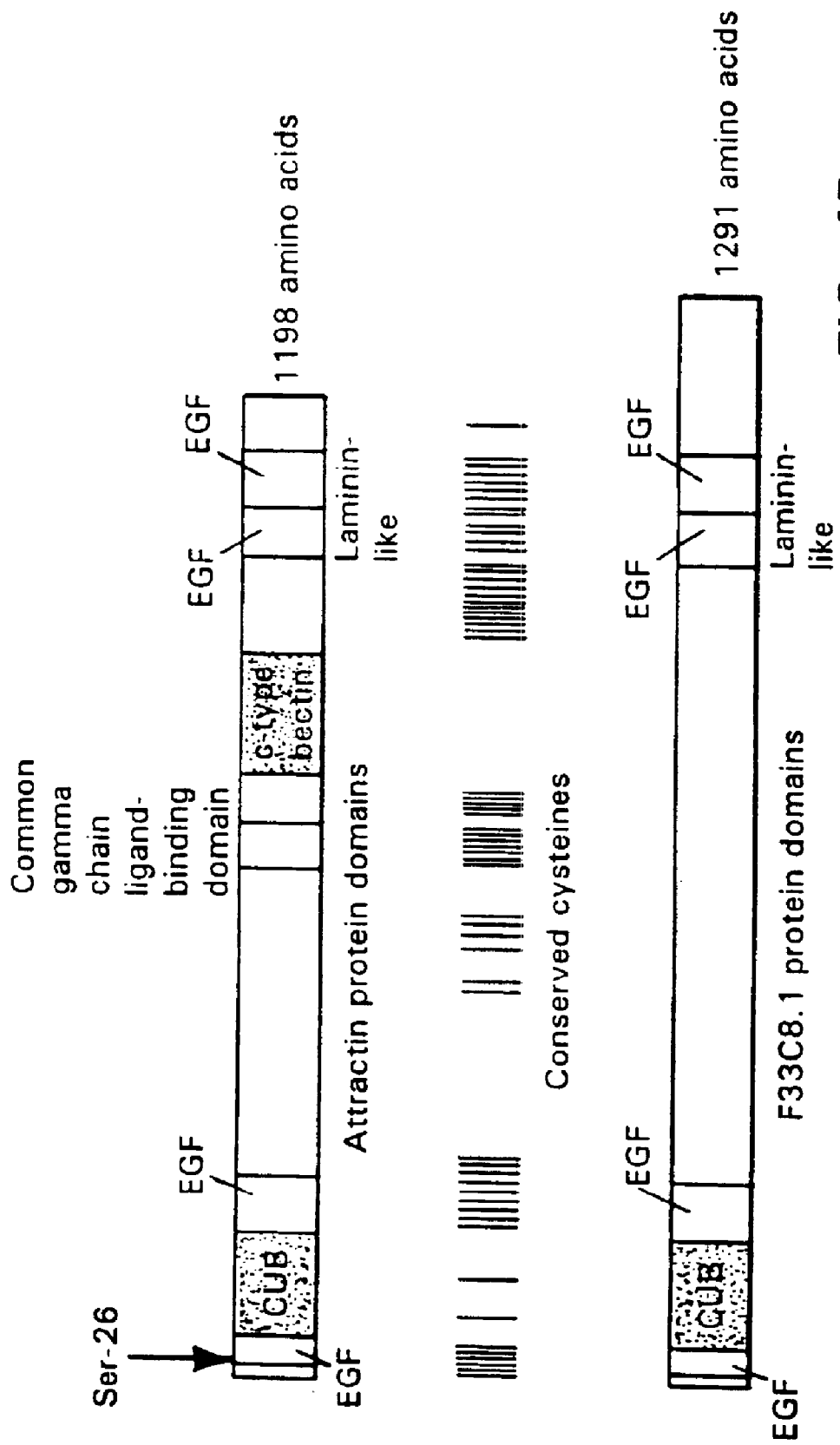

The codon encoding the first methionine of soluble attractin-1 is within a consensus Kozak sequence, and the subsequent ORF codes for a 134 kDa protein with 26 potential N-glycosylation sites. Although soluble attractin-1 is heavily glycosylated, no consensus leader sequence/signal peptides could be identified. Several distinct domains and motifs can be identified in the ORF, as depicted in FIG. 4B. These include a serine (Ser-26) within a hybrid of prolyl oligopeptidase and trypsin-like serine protease catalytic motifs (FIG. 4C), an EGF domain (Gly-24 to Gln-54), a CUB domain (His-57 to Phe-173), an EGF domain (Met-175 to Ala-207), the ligand-binding motif of the common γ cytokine chain (Cys-636 to Trp-648), a C-type lectin domain (Ile-713 to Cys-844), and 2 cysteine-rich regions incorporating the C-terminal laminin-like EGF domains (Ala-988 to Lys-1031 and Pro-1034 to Cys 1066). Fragments of soluble attractin-1 containing one or more of these domains are within the invention, as are nucleic acids encoding such fragments.

The only highly significant match at both the nucleotide and amino aced level (31% identity, 45% similarity across the complete 1198 amino acids) is with the nematode F33C8.1 perlecan-like protein, which has an identical organization of the CUB and EGF domains and conserved cysteine positioning suggestive of a similar secondary structure in the two proteins (FIG. 4B). In contrast to soluble attractin-1, F33C8.1 does not express the γ chain binding motif or the C-type lectin domain. Soluble attractin-1 appears to be a new member of the CUB domain family of proteins, initially consisting of the complement proteins Clr/Cls, Uegf and BMP-1 [Bork et al. (1993) *Mol. Biol.* 231, 539–545].

EXAMPLE 4

Subcellular Localization and Synthesis of the Soluble Attractin Molecule

To understand the secretory route followed by soluble attractin-1 in the absence of a signal peptide, we determined the subcellular localization of soluble attractin-1 in resting and activated $E^+$ T lymphocytes. No glycosylated soluble attractin-1 could be detected anywhere in resting T cells (FIG. 5A), whereas in T cells activated for 48 hr with PHA, soluble attractin-1 was clearly localized in large vesicular structures (FIG. 5B) that often contained an electron-dense core (FIG. 5C). Vesicles containing soluble attractin-1 were often clustered close to the plasma membrane where they released soluble attractin-1 into the extracellular space (FIG. 5D). Soluble attractin-1-encoding cDNA was cloned into the expression vector pRc/CMV which was transfected in CHO cells. Glycosylated soluble attractin-1 could not be detected in the transfected CHO cells. The post-translational glycosylation of soluble attractin-1 was "forced" by cloning soluble attractin-1 cDNA into the pSecTag2B expression vector which supplies a N-terminal leader sequence. In an in vitro transcription/translation system, pSecTag2B-soluble attractin-1 produced a protein of 134 kDa and in the presence of glycosyl transferases yielded a product of bout 180 kDa (FIG. 6A). The correctly sized product was also detected by Western blotting, with antibody specific or myc, of a whole cell lysate of 293T cells transiently transfected with pSecTag2B-soluble attractin-1 (FIG. 6B). The polyclonal antibody specific for soluble attractin immunoprecipitated recombinant soluble attractin-1 from CHO cells stably transfected with pSecTag2B-attractin, confirming that the overall structure of the recombinant protein was similar to that of the purified natural material (FIG. 6C).

EXAMPLE 5

Functional Activities of Recombinant Soluble Attractin-1

Soluble attractin-1 was isolated from lysates of stably transfected CHO cells. Even with a signal peptide, the recombinant attractin localized intracellularly and was not secreted. The DPPIV enzyme activity of the recombinant protein was 0.42 units/mg, in comparison with 0.79 units/mg for T cell-released soluble attractin-1, 1.78 units/mg for serum attractin, and 4.12 units/mg for recombinant CD26.

The PBMC interaction assays depicted in FIG. 1 were repeated using recombinant rather than natural serum-purified soluble attractin-1. This experiment showed that the spreading effect of recombinant soluble attractin-1 on monocytes/macrophages was, as in the experiments with natural serum-purified soluble attractin-1, dose-dependent (FIGS. 7A–7D). At a concentration of 5 μg/ml, the effect was similar to that of 5 μg/ml natural soluble attractin-1 and thus confirmed the results observed with purified natural soluble attractin-1. There was a greater tendency for clustering of T cells when the recombinant soluble attractin-1 was used. However, these clusters were not proliferating cells, as indicated by the fact that no increase in [$^1$H]-thymidine incorporation could be detected over background in cultures of PBMC containing recombinant soluble attractin-1.

EXAMPLE 6

Evidence for Involvement of Attractin in Human Immune Responses

Clinical studies were performed in order to investigate whether attractin plays a role in the human immune system in vivo. Common variable immunodeficiency (CVI) is a late-onset primary immunodeficiency affecting either humoral or cellular immunity. The mechanism underlying this disease is still unknown. In a normal immune response, the surface expression of attractin is upregulated during T cell activation. The early signaling events during T cell activation were studied in 11 patients (age range: 7–27 years) affected by CVI to determine if the expression pattern of attractin is different from that of normal individuals. Cell-surface activation markers, including attractin, were evaluated on resting or 24–48 hour CD3-activated T cells by dual color fluorescence. In cells from all patients but one, in contrast to those from normal control subjects, the T cell surface expression of attractin was not upregulated after CD3 crosslinking. The lack of attractin upregulation was selective in that an increase of the other activation markers was observed in the CVI patients.

EXAMPLE 7

Production of Single Chain Variable Region Fragment (scFv) Antibodies Specific for Attractin Initial efforts to produce murine monoclonal antibodies were unsuccessful, apparently as a direct consequence of the high degree of conservation between the mouse sequence identified to date and the human sequence for attractin. To overcome the problem of antigen conservation across species, techniques have been developed for cloning antigen-binding regions of $V^H$ and $V^L$ genes from the mRNA of non-immune spleen cells, connecting the variable regions with a flexible peptide linker to produce single chain variable region fragments (scFv). The scFv are then expressed as fusion proteins with phage coat protein [Sheets et al. (1998) Proc. Natl. Acad. Sci. USA. 95, 6157–6162] in phage particles. Using this technique, it is possible to generate repertoires of $10^7$ to $10^{10}$ scFv variants. The reagents for generating a library and subsequent enrichment of murine antigen-specific scFv are now available in kit form from Amersham Pharmacia Biotech.

Three separate libraries are simultaneously produced from murine spleen cells. The first library is produced from mRNA of non-immune spleen cells, the second from spleen cells of mice which have received prior immunization with glycosylated native attractin, and a third library from spleen cells of mice which have been immunized with deglycosylated attractin. Messenger RNA is extracted from the lysed spleen cell populations by hybridization to oligo dT cellulose and first strand cDNA is synthesized using M-MuLV reverse transcriptase. Using primers designed to anneal to the 5' and 3' ends of murine heavy chain and kappa light chain variable region sequence, the repertoire of expressed variable regions sequences is amplified by PCR. Lambda light chain sequences are not amplified as they represent only a small fraction of nature antibody-expressed light chain, and the flanking sequences are variable. The PCR products from the heavy chain amplification (≈400 bp) and the kappa light chain amplification (≈300 bp) are separated by agarose gel electrophoresis, gel plugs cut out, and the DNA extracted by freezing and thawing followed by membrane centrifugation.

A linker that hybridizes to the 3' end of the heavy chain and the 5' end of the light chain and encodes the peptide liner (e.g., $Gly_4Ser_3$) is then used to amplify out a full length scFv region of 750 bp. Through use of 5' and 3' primers which carry 5' tails encoding restriction endonuclease sites, Sfi I and Not I sites are added by PCR to the 5' and 3' termini, respectively, of the scFv. After digestion with Sci I followed by Not I, the phenol/chloroform-precipitated fragments are directionally ligated into the pCANTAB 5E phagemid and the construct encoding multiple scfv is used to transform E. coli TG1 cells. The transformed cells are then infected with M13K07 helper phage to rescue the phagemid which will result in expression of the recombinant scFv as a fusion protein based on the gene III phage protein, the fusion protein being displayed on the phage particles.

At this point, the scFv-expressing phages are panned on attractin-coated plates, unbound phages are washed away, bound phage eluted, the phage DNA isolated, and TG1 cells reinfected and allowed to express by superinfection with helper phage. The panning process is repeated up to 3 times in order to refine the specificity. Once antigen-reactive clones have been identified, they are tested for binding by adding the scFv-expressing phage to attractin-coated wells, washing away unbound phage, adding horseradish peroxidase conjugated antibody specific for M13 phage, washing away unbound conjugate and adding ABTS substrate. After confirmation of specific binding by ELISA, the recombinant phage is used to infect E. coli HB2151, which recognizes the amber stop codon encoded by pCANTAB 5E, allowing production of soluble scFv not in the context of the phage gene III protein. The soluble scFv can be isolated from E. coli periplasm using standard procedures and the sample can then be applied to an affinity column bearing antibody directed against a peptide region (-Gly-Ala-Pro-Val-Pro-Tyr-Pro-Asp-Pro-Leu-Glu-Pro-Arg-Ala-Ala-COOH (SEQ ID NO:9)) downstream from the kappa light chain and which generates a C-terminal common to all the scFv fragments. Binding occurs at neutral pH and, comparable to a normal antigen-antibody reaction, can be eluted at acidic pH. This peptide can be recognized by its specific antibody under native and denatured conditions. scFv produced in this way will provide a very specific handle for studying T lymphocyte intracellular expression and surface expression of attractin, for determining the kinetics of surface expression during clustering, for blocking functional clustering assays, and for determining both levels of attractin released from T cells during assays in vitro and levels in biological fluids.

In addition to maximizing selection of antibodies with the greatest affinity, panels of scFv directed against specific epitopes of attractin are developed. This is achieved by taking all isolated attractin-specific scFv and repeating the ELISA assays described above using the above-described forms of attractin and attractin deletion mutants as the target antigen. Selective binding of the scFv to one form of attractin but not to another or the deletion mutants will indicate that the scFv is specific for the relevant form of attractin or the deleted part of the polypeptide, respectively.

EXAMPLE 8

Identification of the Nucleotide and Amino Acid Sequence of Membrane Attractin-1

Initially, a 9 kb murine mRNA was shown to encode a molecule which was similar to human attractin-1. Sequence analysis of murine cDNA revealed that the nucleotide sequence diverged, extended the open reading frame, and coded for a transmembrane domain and a cytoplasmic domain. Given the 93% identity in the amino acid sequences of the regions shared by human soluble attractin-1 and murine attractin, it was hypothesized that an oligonucleotide probe based on the region coding for the murine cytoplasmic tail would also hybridize to a human mRNA that coded for an attractin with a cytoplasmic tail. This was found to be the case. Such a probe hybridized to the 9 kb human attractin mRNA but not to the 4.5 kb form, while a probe based on sequence coding for the common N-terminal sequence hybridized to both forms. This indicated that the 9 kb human mRNA coded for a long attractin similar to the murine molecule. Searching of the EST database then revealed a deposited human sequence (KIAA0548; GenBank AB011120) that coded for 451 amino acids at the C-terminal of a human membrane attractin. The identification of this sequence re-enforced the hypothesis that a natural mRNA for membrane attractin existed. Using KIAA0548 as a base, a human genomic clone that contained an apparent attractin exon corresponding to the sequence coding for the amino acid sequence CEVENRYQGNPLRGTCY (SEQ ID NO:20), close to the C-terminal of attractin, was identified. Complete sequencing of this genomic clone proved conclusively that the divergence between soluble attractin-1, and membrane attractin-1, was the result of alternate splicing.

The nucleotide sequence of cDNA encoding human membrane attractin-1 (SEQ ID NO:11) is shown in FIG. 10 and the amino acid sequence of the human membrane attractin-1 protein (SEQ ID NO:10) is shown in FIG. 9. Note that the C-terminal five amino acids of soluble attractin-1 (SEQ ID NO:2 in FIG. 2) differs from the equivalent five amino acids in membrane attractin-1 and it lacks an additional 156 C-terminal amino acid residue region containing a transmembrane domain (amino acid residues 1205–1225) domain and a cytoplasmic domain C-terminal to the transmembrane domain.

EXAMPLE 9

Deduction of the Attractin-2 cDNA and Protein Sequences

Multiple attractin cDNA species covering the 5' region have been identified which include or do not include a 222-bp insertion encoding a 74 amino acid region that defines attractin-2 proteins. Since there is no reason to suppose that this region can in any way influence 3' splicing events, it is likely that both membrane and soluble attractin mRNA species containing the 222-bp insertion are generated. Further evidence that such transcripts exist comes from experiments with mouse mRNA from which it is clear that there are multiple mouse attractin mRNA species of which the membrane form, at least, contains a 72 amino acid (216 bp) insertion corresponding to the 74 amino acid insertion of human attractin-2. Thus, the invention includes both soluble attractin-2 (SEQ ID NO:18) (FIG. 11), membrane attractin-2 (SEQ ID NO:12) (FIG. 13) and the cDNA sequences encoding soluble attractin-2 (SEQ ID NO:19) (FIG. 12) and membrane attractin-2 (SEQ ID NO:13) (FIG. 14). The transmembrane domain of membrane attractin-2 is predicted to include residues 1279–1301 of SEQ ID NO:12 and its cytoplasmic domain is predicted to include all residues C-terminal of the transmembrane domain.

EXAMPLE 10

Figure 15:
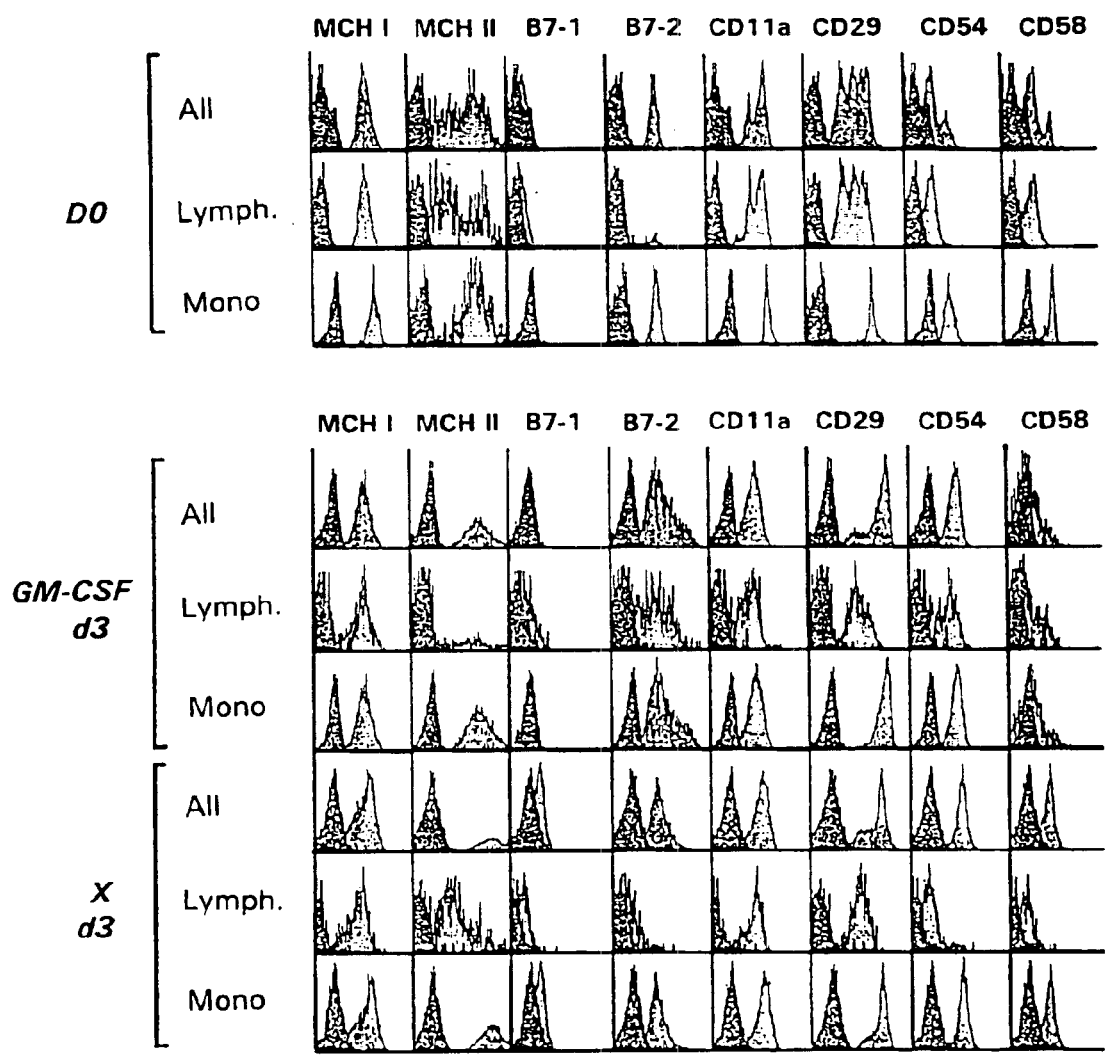
FIG. 15 is a series of fluorescence flow cytometric histograms showing the expression of MHC class I, MHC class II, B7.1, B7.2, CD11a, CD29, CD54, and CD58 molecules on the surface of total peripheral blood leukocytes ("All"), lymphocytes ("Lymph"), and monocytes ("Mono"), prior to culture ("D0"), and after a 72 hr incubation of peripheral blood leukocytes with either recombinant soluble attractin-1 ("X") or granulocyte macrophage colony-stimulating factor ("GM-CSF").

Recombinant Soluble Attractin-1 Increases Expression of MHC Class II and B7.1 Molecules on Monocytes Peripheral blood leukocytes were isolated (from blood donated by normal donors in the Blood Bank of the Dana Farber Cancer Institute) by centrifugation over Ficoll-Hypaque. The isolated cells were suspended in defined lymphocyte culture medium (AIM V; GIBCO-BRL) at a concentration of $2 \times 10^6$ per ml and incubated at 37° C. in an atmosphere of 7.5% $CO_2$ for 72 hr with soluble recombinant attractin-1 (at 5 ug/ml) or with GM-CSF (10 U/ml). Non-adherent cells were then discarded and adherent cells were recovered using PBS containing 5 mM EDTA and washed in AIM V medium. All cells were suspended at a concentration of $10^7$ per ml. 100 ul aliquots (corresponding to $10^6$ cells) were incubated with 0.25 to 1 ug of a panel of FITC- or phycoerythrin-labelled antibodies directed against a selection of known pan-leukocyte, T cell-specific, B cell-specific, monocyte-specific and NK-specific markers. Using the Coulter XL fluorescence analysis machine, fluorescence windows were gated on the total cell population, the lymphocyte population, and the monocyte population that is distinguished by size and light "scatter" (FIG. 15). The profiles with dark fill were obtained with control cells incubated with antibodies of irrelevant specificity conjugated with appropriate fluorophores, and those with light fill were obtained with cells incubated with antibodies with the indicated specificity. Also shown in FIG. 15 are similar data obtained with peripheral blood leukocytes prior to culture (DO).

Monocytes incubated with GM-CSF differentiated by losing CD14 (FIG. 15) and expressing CD1a (not shown), indicating a differentiation towards early dendritic cells. For monocytes incubated with soluble attractin-1 in the presence of CD3+ T lymphocytes, CD14 remains high, there is no induction of CD1a (not shown), B7-1 expression begins to increase, and MHC Class II expression increases off scale (FIG. 15). These findings indicate that attractin serves to enhance the antigen presenting function of monocytes.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. An isolated DNA comprising a nucleic acid sequence that encodes an amino acid sequence comprising SEQ ID NO:12.

2. An isolated DNA comprising a nucleic acid sequence consisting of SEQ ID NO:13.

3. An isolated nucleic acid comprising a nucleic acid sequence encoding a fusion protein, the fusion protein consisting of:
   (a) SEQ ID NO:12 or an antigenic fragment of SEQ ID NO:12, wherein the antigenic fragment is at least five amino acids long; and
   (b) a heterologous polypeptide.

4. A vector comprising the isolated DNA of claim 1.

5. The vector of claim 4, wherein the nucleic acid sequence is operably linked to a regulatory element that allows expression of said nucleic acid sequence in a cell.

6. An isolated cell comprising the vector of claim 5.

7. A method of producing a polypeptide, the method comprising culturing the cell of claim 6 and purifying the polypeptide from the cell.

8. A vector comprising the isolated nucleic acid of claim 3.

9. The vector of claim 8, wherein the nucleic acid is operably linked to a regulatory element that allows expression of said nucleic acid in a cell.

10. An isolated cell comprising the vector of claim 8.

11. A method of producing a fusion protein, the method comprising culturing the cell of claim 10 and purifying the fusion protein from the cell.

12. An isolated DNA comprising:
   (a) a nucleic acid sequence that (i) encodes a polypeptide that enhances spreading of a macrophage or a monocyte and (ii) hybridizes to the complement of SEQ ID NO:13 under the following conditions: hybridization in 6× SSC at 30° C., followed by one or more washes in 0.2× SSC and 0.1% sodium dodecyl sulfate (SDS) at 50° C. to 65° C., wherein the nucleic acid sequence consists of SEQ ID NO:1; or
   (b) the complement of the nucleic acid sequence.

13. An isolated DNA comprising:
   (a) a nucleic acid sequence that (i) encodes a polypeptide that enhances spreading of a macrophage or a monocyte and (ii) hybridizes to the complement of SEQ ID NO:13 under the following conditions: hybridization in 6× SSC at 30° C., followed by one or more washes in 0.2× SSC and 0.1% sodium dodecyl sulfate (SDS) at 50° C. to 65° C., wherein the nucleic acid sequence consists of SEQ ID NO:11; or
   (b) the complement of the nucleic acid sequence.

14. An isolated DNA comprising:
   (a) a nucleic acid sequence that (i) encodes a polypeptide that enhances spreading of a macrophage or a monocyte and (ii) hybridizes to the complement of SEQ ID NO:13 under the following conditions: hybridization in 6× SSC at 30° C., followed by one or more washes in 0.2× SSC and 0.1% sodium dodecyl sulfate (SDS) at 50° C. to 65° C., wherein the nucleic acid sequence consists of SEQ ID NQ: 9; or
   (b) the complement of the nucleic acid sequence.

15. The isolated nucleic acid of claim 3, wherein the heterologous polypeptide comprises a signal peptide, a reporter polypeptide, or an immunoglobulin constant region.

16. An isolated DNA consisting of a sequence encoding an antigenic fragment of SEQ ID NO:12, wherein the antigenic fragment is at least five amino acids long.

17. An isolated DNA comprising a nucleic acid sequence that encodes a polypeptide consisting of the following segments in contiguous order, starting from the N-terminus of the amino acid sequence:
   (a) amino acids 1–30 of SEQ ID NO:12;
   (b) amino acids 31–104 of SEQ ID NO:12;
   (c) amino acids 105–1267 of SEQ ID NO:12; and
   (d) amino acids 1268–1429 of SEQ ID NO:12 or amino acids 1194–1999 of SO ID NO:2,
   wherein the polypeptide enhances spreading of a macrophage or a monocyte.

18. The DNA of claim 17, wherein the polypeptide comprises amino acids 1194–1999 of SEQ ID NO:2.

19. The DNA of claim 17, wherein the polypeptide comprises amino acids 1268–1429 of SEQ ID NO:12.

20. A vector comprising the isolated DNA of claim 16.

21. The vector of claim 20, wherein the nucleic acid sequence is operably linked to a regulatory element that allows expression of the nucleic acid sequence in a cell.

22. An isolated cell comprising the vector of claim 21.

23. A method of producing a polypeptide, the method comprising culturing the cell of claim 22 and purifying the polypeptide from the cell.

24. A vector comprising the isolated DNA of claim 17.

25. The vector of claim 24, wherein the nucleic acid sequence is operably linked to a regulatory element that allows expression of the nucleic acid sequence in a cell.

26. An isolated cell comprising the vector of claim 25.

27. A method of producing a polypeptide, the method comprising culturing the cell of claim 26 and purifying the polypeptide from the cell.

28. The nucleic acid of claim 3, wherein a nucleotide sequence encoding the antigenic fragment is at least 50 nucleotides long.

29. The nucleic acid of claim 28, wherein the nucleotide sequence is at least 100 nucleotides long.

30. The nucleic acid of claim 28, wherein the nucleotide sequence is at least 300 nucleotides long.

31. The nucleic acid of claim 28, wherein the nucleotide sequence is at least 800 nucleotides long.

32. The nucleic acid of claim 28, wherein the nucleotide sequence is at least 1,500 nucleotides long.

33. The nucleic acid of claim 28, wherein the nucleotide sequence is at least 3,000 nucleotides long.

34. The nucleic acid of claim 28, wherein the nucleotide sequence is at least 4,000 nucleotides long.

35. The DNA of claim 16, wherein the a nucleotide sequence encoding the antigenic fragment is at least 50 nucleotides long.

36. The DNA of claim 35, wherein the nucleotide sequence is at least 100 nucleotides long.

37. The DNA of claim 35, wherein the nucleotide sequence is at least 300 nucleotides long.

38. The DNA of claim 35, wherein the nucleotide sequence is at least 800 nucleotides long.

39. The DNA of claim 35, wherein the nucleotide sequence is at least 1,500 nucleotides long.

40. The DNA of claim 35, wherein the nucleotide sequence is at least 3,000 nucleotides long.

41. The DNA of claim 35, wherein the nucleotide sequence is at least 4,000 nucleotides long.

42. An isolated DNA comprising a nucleic acid sequence that encodes a polypeptide consisting of the following segments in contiguous order, starting from the N-terminus of the amino acid sequence:

(a) amino acids 1–30 of SEQ ID NO:12;

(b) amino acids 105–1267 of SEQ ID NO:12; and (c) amino acids 1268–1429 of SEQ ID NO:12, or amino acids 1194-1999 of SEO ID NO: 2, wherein the polypeptide enhances spreading of a macrophage or a monocyte.

43. A vector comprising the isolated DNA of claim 42.

44. The vector of claim 43, wherein the nucleic acid sequence is operably linked to a regulatory element that allows expression of the nucleic acid sequence in a cell.

45. An isolated cell comprising the vector of claim 44.

46. A method of producing a polypeptide, the method comprising culturing the cell of claim 45 and purifying the polypeptide from the cell.

\* \* \* \* \*